United States Patent
Holton et al.

(10) Patent No.: US 6,727,369 B1
(45) Date of Patent: Apr. 27, 2004

(54) PROCESS FOR THE PREPARATION OF BACCATIN III ANALOGS BEARING NEW C2 AND C4 FUNCTIONAL GROUPS

(75) Inventors: Robert A. Holton, Tallahassee, FL (US); Seokchan Kim, Seoul (KR); Yukio Suzuki, Sendai (JP)

(73) Assignee: Florida State University, Tallahassee, FL (US)

( * ) Notice: Subject to any disclaimer, the term of this patent is extended or adjusted under 35 U.S.C. 154(b) by 1,826 days.

(21) Appl. No.: 08/374,520

(22) PCT Filed: Jan. 31, 1994

(86) PCT No.: PCT/US94/01099

§ 371 (c)(1),
(2), (4) Date: Apr. 14, 1995

(87) PCT Pub. No.: WO94/17051

PCT Pub. Date: Aug. 4, 1994

Related U.S. Application Data

(63) Continuation-in-part of application No. 08/010,798, filed on Jan. 29, 1993, now Pat. No. 5,399,726.

(51) Int. Cl.$^7$ ................ C07D 317/70; C07D 305/14
(52) U.S. Cl. .................. 549/229; 549/214; 549/228; 549/510; 549/511
(58) Field of Search ................ 549/229, 214, 549/228, 510, 511

(56) References Cited

U.S. PATENT DOCUMENTS

| | | | |
|---|---|---|---|
| 4,814,470 A | 3/1989 | Colin et al. | 514/449 |
| 4,876,399 A | 10/1989 | Holton et al. | 568/817 |
| 4,924,011 A | 5/1990 | Denis et al. | 549/510 |
| 4,924,012 A | 5/1990 | Colin et al. | 549/510 |
| 5,175,315 A | 12/1992 | Holton | 549/510 |
| 5,399,726 A * | 3/1995 | Holton et al. | 549/510 |
| 5,416,225 A | 5/1995 | Danishefsky et al. | 549/341 |
| 5,488,116 A | 1/1996 | Danishefsky et al. | 549/214 |
| 5,698,712 A | 12/1997 | Bombardelli et al. | |
| 5,763,477 A | 6/1998 | Duvvuri et al. | |

OTHER PUBLICATIONS

Borman, Stu, "New family of Taxol, Taxotere analogs developed," Chemical & Engineering News, Apr. 12, 1993, pp. 36–37, vol. 17, No. 15.

Kingston et al. "Progress in the Chemistry of Organic Natural Products" Springer–Verlag, New York (1993) pp. 26, 68, 176, 181, 183, 185, 189.

Holton et al. "A Synthesis of Taxusin" Journal of American Chemical Society, vol. 110 (1988) pp. 6558–6560.

Samaranayake et al. "Modified Taxols. 5.1 Reaction of Taxol with Electrophilic Reagents and Preparation of a Rearranged Taxol Derivative with Tublin Assembly Activity3." Journal of Organic Chemistry, vol. 56 (1991) pp. 5114–5119.

Denis et al. "A Highly Efficient, Practical Approach to Natural Taxol" Journal of American Chemical Society, vol. 110 (1988) pp. 5917–5919.

Farina et al. "The Chemistry of Taxanes: Unexpected Rearrangement of Baccatin III During Chemoselective Debenzoylation with Bu$_3$SnOMe/LiCl" Tetrahedron Letters, vol. 33, No. 28 (1992) pp. 3979–3982.

Chen et al. "Taxol Structure–Activity Relationships: Synthesis and Biological Evaluation of 2–Deoxytaxol" Tetrahedron Letters, vol. 34, No. 20 (1993) pp. 3205–3206.

Miller et al., "Antileukemic Alkaloids from Taxus Wallichiana Zucc." Journal of Organic Chemistry, vol. 46 (1981) pp. 1469–1474.

Klein "Syntehsis of 9–Dihydrotaxol: A Novel Bioactive Taxane" Tetrahedron Letters, vol. 34, No. 13 (1993) pp. 2047–2050.

* cited by examiner

*Primary Examiner*—Ba K. Trinh
(74) *Attorney, Agent, or Firm*—Senniger, Powers, Leavitt & Roedel

(57) ABSTRACT

Process for the preparation of a derivative or analog of baccatin III or 10-desacetyl baccatin III having a C2 substituent other than benzoate and/or a C4 substituent other than acetate in which the C2 benzoate substituent and/or the C4 acetate substituent of a derivative of baccatin III or 10-desacetyl baccatin III is/are selectively reduced to the corresponding hydroxy group(s) and converted to $R_7$COO— and/or $R_8$COO—, respectively, wherein $R_7$ and $R_8$ are independently H, $C_1$–$C_6$ alkyl, $C_2$–$C_6$ alkenyl, $C_2$–$C_8$ alkynyl, moncyclic aryl, or monocyclic heteroaryl.

56 Claims, No Drawings

PROCESS FOR THE PREPARATION OF BACCATIN III ANALOGS BEARING NEW C2 AND C4 FUNCTIONAL GROUPS

REFERENCE TO RELATED APPLICATIONS

This application is a continuation-in-part application of U.S. Ser. No. 08/010,798, filed Jan. 29, 1993, now U.S. Pat. No. 5,399,726, and a 371 application of PCT/US94/01099 filed Jan. 31, 1994.

This invention was made with Government support under NIH Grant #CA 42031 and NIH Grant #CA 55131 awarded by the National Institutes of Health. The Government has certain rights in the invention.

BACKGROUND OF THE INVENTION

The present invention relates to a process for the preparation of baccatin III and 10-desacetylbaccatin III analogs having new C2 and/or C4 functional groups.

Taxol is a natural product extracted from the bark of yew trees. It has been shown to have excellent antitumor activity in in vivo animal models, and recent studies have elucidated its unique mode of action, which involves abnormal polymerization of tubulin and disruption of mitosis. It is currently undergoing clinical trials against ovarian, breast and other types of cancer in the United States and France and preliminary results have confirmed it as a most promising chemotherapeutic agent. The structure of taxol and the numbering system conventionally used is shown below; this numbering system is also applicable to compounds used in the process of the present invention.

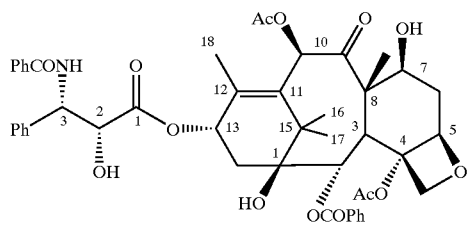

In Colin U.S. Pat. No. 4,814,470, it was reported that a taxol derivative, commonly referred to as taxotere, has an activity significantly greater than taxol. Taxotere has the following structure:

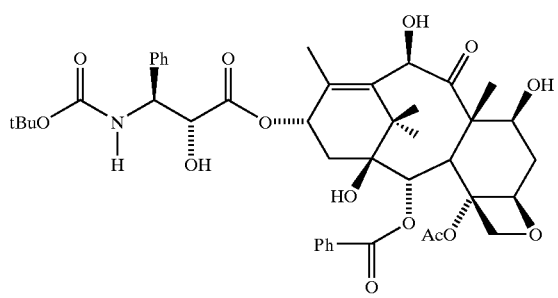

Taxol, taxotere and other biologically active tetracyclic taxanes may be prepared semisynthetically from baccatin III and 10-desacetyl baccatin III as set forth in U.S. Pat. Nos. 4,924,011 and 4,924,012 or by the reaction of a β-lactam and a suitably protected baccatin III or 10-desacetylbaccatin III ("10-DAB") derivative as set forth in U.S. Pat. No. 5,175, 315 or copending U.S. patent application Ser. No. 07/949, 107 (which is incorporated herein by reference). Baccatin III 1 and 10-DAB 2 can be separated from mixtures extracted from natural sources such as the needles, stems, bark or heartwood of numerous Taxus species and have the following structures.

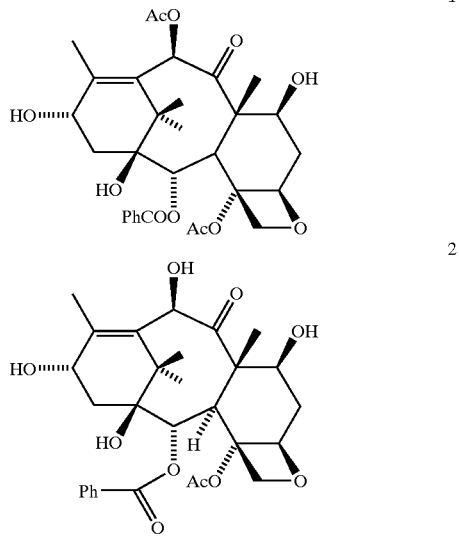

The tetracyclic core of taxol and taxotere bear six singly bonded oxygen substituents. Two of these (three in the case of taxotere) are present as hydroxyl groups, and the others are esters of three different carboxylic acids. Selective manipulation of these groups presents a formidable problem which must be overcome before a series of taxol analogs can be prepared by a rational synthetic sequence. Hydrolytic and solvolytic methods have previously encountered complications. For example, it has been reported by that hydrolysis of taxol under mildly basic conditions yields a complex mixture of products. Miller et al., *J. Org. Chem.* 1981, 46, 1469. Recently it has been found that solvolysis of baccatin (III) derivatives leads to rearrangement of the tetracyclic core. Farina, et al., Tetrahedron Lett. 1992, 33, 3979.

SUMMARY OF THE INVENTION

Among the objects of the present invention, therefore, is the provision of a process for selectively attaching different functional groups to the C2 and/or C4 oxygens of baccatin III and analogs or derivatives thereof; the provision of such a process which is relatively straightforward; the provision of such a process in which the C2 benzoate substituent of baccatin III and analogs or derivatives thereof may be selectively reduced or hydrolyzed and the provision of such a process in which the C4 acetate substituent may be selectively reduced.

Briefly, therefore, the present invention is directed to a process for the preparation of analogs or derivatives of baccatin III or 10-desacetyl baccatin III in which the C2 substituent and/or the C4 acetate substituent of baccatin III or 10-desacetoxy baccatin III or an analog thereof is selectively converted to the corresponding hydroxy group(s).

The present invention is additionally directed to a derivative of baccatin III or 10-desacetyl baccatin III having the formula

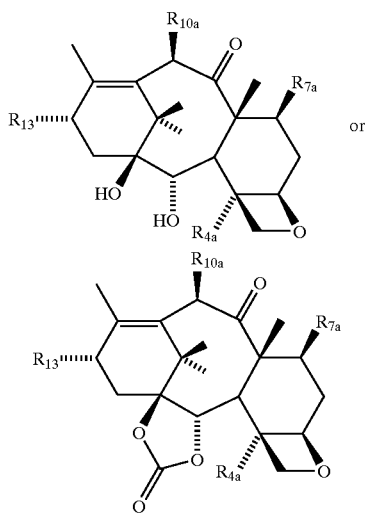

wherein $R_{4a}$, $R_{7a}$, $R_{10a}$, and $R_{13a}$ are as defined elsewhere herein.

Other objects and features of this invention will be in part apparent and in part pointed out hereinafter.

DETAILED DESCRIPTION OF THE INVENTION

As used herein "Ar" means aryl; "Ph" means phenyl; "Me" means methyl; "Et" means ethyl; "iPr" means isopropyl; "tBu" and "t-Bu" means tert-butyl; "R" means lower alkyl unless otherwise defined; "Ac" means acetyl; "py" means pyridine; "TES" means triethylsilyl; "TMS" means trimethyl-silyl; "TBS" means $Me_2t\text{-}BuSi$—; "Tf" means —$SO_2CF_3$; "BMDA" means $BrMgNiPr_2$; "Swern" means $(COCl)_2$, $Et_3N$; "LTMP" means lithium tetramethylpiperidide; "MOP" means 2-methoxy-2-propyl; "BOM" means benzyloxymethyl; "LDA" means lithium diisopropylamide; "LAH" means lithium aluminum hydride; "Red-Al" means sodium bis(2-methoxyethoxy) aluminum hydride; "Ms" means $CH_3SO_2$—; "TASF" means tris(diethylamino) sulfoniumdifluorotrimethylsilicate; "Ts" means toluenesulfonyl; "TBAF" means tetrabutyl ammonium hydride; "TPAP" means tetrapropyl-ammonium perruthenate; "DBU" means diazabicycloundecane; "DMAP" means p-dimethylamino pyridine; "LHMDS" means lithium hexamethyldisilazide; "DMF" means dimethylformamide; "AIBN" means azo-(bis)isobutyronitrile; "10-DAB" means 10-desacetylbaccatin III; "FAR" means 2-chloro-1,1,2-trifluorotriethylamine; "mCPBA" means metachloroperbenzoic acid; "DDQ" means dicyanodichloroquinone; "sulfhydryl protecting group" includes, but is not limited to, hemithioacetals such as 1-ethoxyethyl and methoxymethyl, thioesters, or thiocarbonates; "amine protecting group" includes, but is not limited to, carbamates, for example, 2,2,2-trichloroethylcarbamate or tertbutylcarbamate; "protected hydroxy" means —OP wherein P is a hydroxy protecting group; and "hydroxy protecting group" includes, but is not limited to, acetals having two to ten carbons, ketals having two to ten carbons, ethers such as methyl, t-butyl, benzyl, p-methoxybenzyl, p-nitrobenzyl, allyl, trityl, methoxymethyl, methoxyethoxymethyl, ethoxyethyl, tetrahydropyranyl, tetrahydrothiopyranyl, and trialkylsilyl ethers such as trimethylsilyl ether, triethylsilyl ether, dimethylarylsilyl ether, triisopropylsilyl ether and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates including but not limited to alkyl carbonates having from one to six carbon atoms such as methyl, ethyl, n-propyl, isopropyl, n-butyl, t-butyl; isobutyl, and n-pentyl; alkyl carbonates having from one to six carbon atoms and substituted with one or more halogen atoms such as 2,2,2-trichloroethoxymethyl and 2,2,2-tri-chloroethyl; alkenyl carbonates having from two to six carbon atoms such as vinyl and allyl; cycloalkyl carbonates having from three to six carbon atoms such as cyclopropyl, cyclobutyl, cyclopentyl and cyclohexyl; and phenyl or benzyl carbonates optionally substituted on the ring with one or more $C_{1-6}$ alkoxy, or nitro. Other hydroxyl, sulfhydryl and amine protecting groups may be found in "Protective Groups in Organic Synthesis" by T. W. Greene, John Wiley and Sons, 1981.

The alkyl groups described herein are preferably lower alkyl containing from one to six carbon atoms in the principal chain and up to 15 carbon atoms. They may be straight or branched chain and include methyl, ethyl, propyl, isopropyl, butyl, hexyl and the like. They maybe heterosubstituted with the various substituents defined herein, including alkaryl.

The alkenyl groups described herein are preferably lower alkenyl containing from two to six carbon atoms in the principal chain and up to 15 carbon atoms. They may be straight or branched chain and include ethenyl, propenyl, isopropenyl, butenyl, isobutenyl, hexenyl, and the like. They may be heterosubstituted with the various substituents defined herein, including alkenaryl.

The alkynyl groups described herein are preferably lower alkynyl containing from two to six carbon atoms in the principal chain and up to 15 carbon atoms. They may be straight or branched chain and include ethynyl, propynyl, butynyl, isobutynyl, hexynyl, and the like. They may be heterosubstituted with the various substituents defined herein, including alkynaryl.

The aryl moieties described herein contain from 6 to 15 carbon atoms and include phenyl. They may be hydrocarbon or heterosubstituted with the various substituents defined hereinbelow. Phenyl is the more preferred aryl.

The heteroaryl moieties described herein contain from 5 to 15 atoms and include, furyl, thienyl, pyridyl and the like. They may be hydrocarbon or heterosubstituted with the various substituents defined hereinbelow.

The acyl moieties described herein contain alkyl, alkenyl, alkynyl, aryl or heteroaryl groups.

The alkoxycarbonyloxy moieties described herein comprise lower alkyl, alkenyl, alkynyl or aryl groups.

The hydrocarbon substituents described herein may be alkyl, alkenyl, alkynyl, or aryl, and the heterosubstituents of the heterosubstituted alkyl, alkenyl, alkynyl, aryl, and heteroaryl moieties described herein contain nitrogen, oxygen, sulfur, halogens and/or one to six carbons, and include lower alkoxy such as methoxy, ethoxy, butoxy, halogen such as chloro or fluoro, and nitro, heteroaryl such as furyl or thienyl, alkanoxy, hydroxy, protected hydroxy, acyl, acyloxy, nitro, amino, and amido.

Surprisingly, it has been discovered that the C2 ester of a suitably protected derivative of baccatin III or 10-DAB having the formula

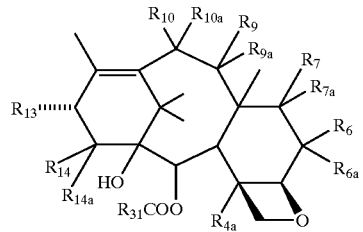

may be selectively reduced to form a 1,2 diol having the formula

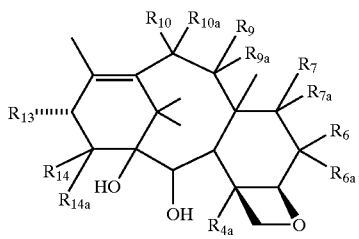

which, in turn, may be converted to a 1,2 carbonate intermediate which permits the selective formation of a variety of C2 esters through reaction with alkyl, alkenyl, alkynyl or aryl lithium reagents or Grignard reagents. The 1,2 carbonate intermediate has the formula

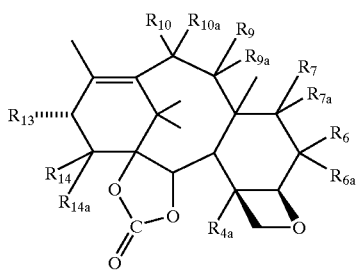

wherein $R_{4a}$ is hydrogen, alkyl, alkenyl, alkynyl, aryl, heteroaryl, cyano, hydroxy, or —$OCR_{30}$;

$R_6$ is hydrogen, alkyl, alkenyl, alkynyl, aryl, or heteroaryl, hydroxy, protected hydroxy or together with $R_{6a}$ forms an oxo;

$R_{6a}$ is hydrogen, alkyl, alkenyl, alkynyl, aryl, or heteroaryl, hydroxy, protected hydroxy or together with $R_6$ forms an oxo;

$R_7$ is hydrogen or together with $R_{7a}$ forms an oxo, $R_{7a}$ is hydrogen, halogen, protected hydroxy, —$OR_{28}$, or together with $R_7$ forms an oxo;

$R_9$ is hydrogen or together with $R_{9a}$ forms an oxo, $R_{9a}$ is hydrogen, hydroxy, protected hydroxy, or together with $R_9$ forms an oxo;

$R_{10}$ is hydrogen or together with $R_{10a}$ forms an oxo, $R_{10a}$ is hydrogen, hydroxy, protected hydroxy, or together with $R_{10}$ forms an oxo;

$R_{13}$ is hydroxy or protected hydroxy;

$R_{14}$ is hydrogen, alkyl, alkenyl, alkynyl, aryl, or heteroaryl;

$R_{14a}$ is hydrogen, alkyl, alkenyl, alkynyl, aryl, or heteroaryl, hydroxy, protected hydroxy or together with $R_1$ forms a carbonate;

$R_{28}$ is hydrogen, hydroxy protecting group or a functional group which increases the solubility of the taxane derivative; and $R_{30}$ and $R_{31}$ are independently hydrogen, alkyl, alkenyl, alkynyl, monocyclic aryl or monocyclic heteroaryl.

Any agent which selectively removes the C2 and/or C4 acyl groups and thereby converts the ester(s) to the corresponding alcohol(s) may be used. The agent may be a reducing agent, preferably a hydride of aluminum or boron, more preferably an alkyl substituted aluminum hydride or an alkyl substituted borohydride, and most preferably lithium aluminum hydride ("LAH"), sodium bis(2-methoxyethoxy) aluminum hydride ("Red-Al") or lithiumtriethylborohydride. Alternatively, the agent may be a base, preferably a tetraalkylammonium base and most preferably, tetrabutylammoniumhydroxide. The conversion of the ester to the corresponding alcohol is carried out in a single phase, non-aqueous system such as methylene chloride.

After the C2 and/or C4 esters are reduced to the corresponding alcohol(s), standard acylating agents such as anhydrides and acid chlorides in combination with an amine such as pyridine, triethylamine, DMAP, or diisopropyl ethyl amine can be used to form new esters at C2 and/or C4. Alternatively, the C2 and/or C4 alcohols may be converted to new C2 and/or C4 esters through formation of the corresponding alkoxide by treatment of the alcohol with a suitable base such as LDA followed by an acylating agent such as an acid chloride.

As will be discussed in greater detail below, baccatin III and 10-DAB derivatives having new C2 and/or C4 esters can be produced by several reaction schemes. To simplify the description, 10-DAB is used as the starting material in Reaction Schemes 1–6. Baccatin III derivatives or analogs, however, may be produced using the same reactions (except for the protection of the C10 hydroxy group with TES) by simply replacing 10-DAB with baccatin III as the starting material.

Scheme 1

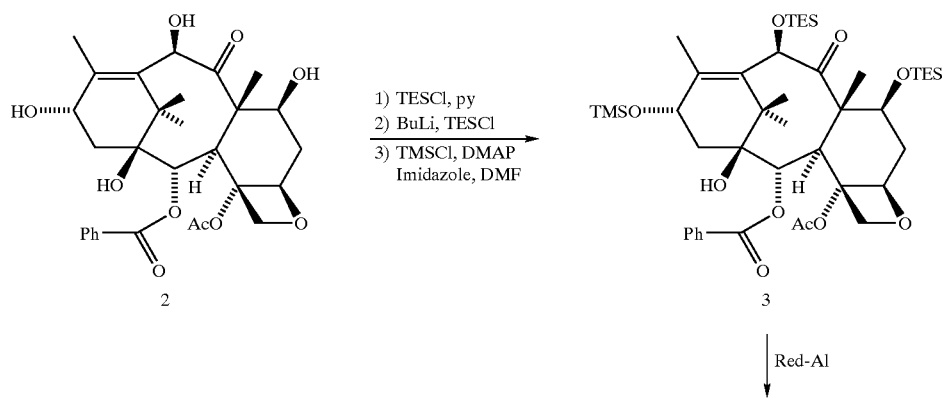

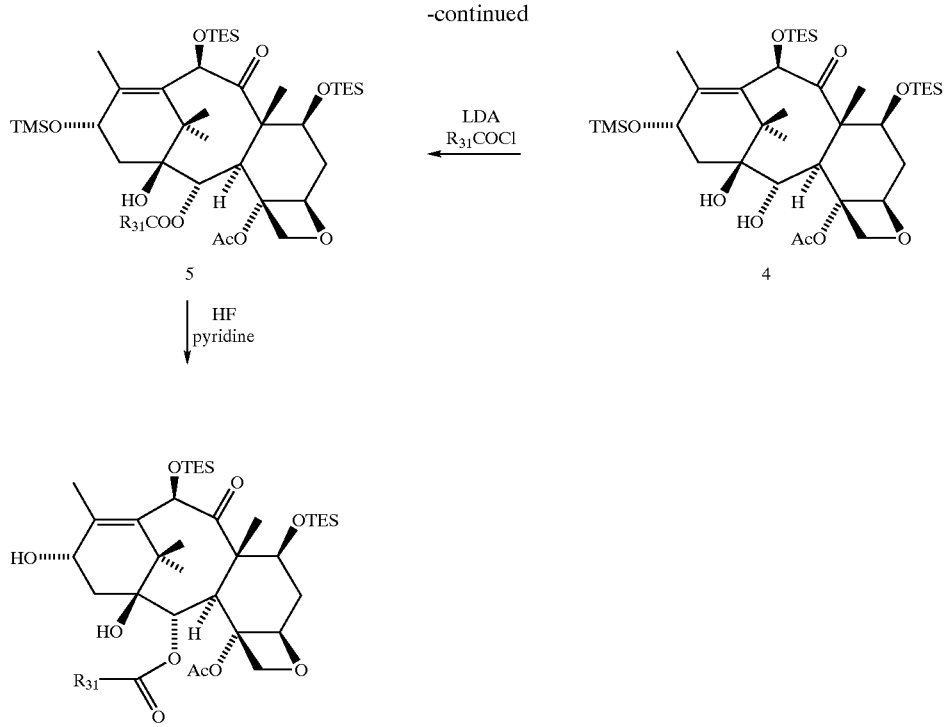

In Reaction Scheme 1, the C7 hydroxyl group of 10-deacetyl baccatin (III) was selectively protected as its triethylsilyl (TES) ether as described by Green, et al., JACS 110, 5917 (1988). The C10 hydroxyl group was then protected as the TES ether through the use of n-butyllithium and triethylsilyl chloride. The C13 hydroxyl group was subsequently protected as the trimethylsilyl (TMS) ether, which could be selectively removed at a later stage. The fully protected 13-O-trimethylsilyl-7,10-bis-O-triethylsilyl10-deacetyl baccatin (III) 3 underwent selective reduction with Red-Al to give the 2 hydroxy derivative 4. 2 hydroxy derivative 4 may alternatively be obtained by selectively reducing the fully protected baccatin III 3 with tetrabutylammonium borohydride in either or by hydrolyzing the C4 ester of fully protected baccatin III with tetrabutylammoniumhydroxide. Deprotonation of 4 with ether n-butyllithium or a bulky amide base such as LDA was followed by the addition of an appropriate acid chloride to provide the C2 ester derivative 5. The C13 TMS group may then be removed using HF.

As shown in Reaction Scheme 2, 1,2 diol 4 can be readily converted to the 1,2 carbonate 6 which can be transformed to the C2 formate 5 ($R_{31}$=H) by treatment with Red-Al under mild conditions. In addition, carbonate 6 reacts selectively with nucleophilic agents (e.g., Grignard reagents or alkyllithium reagents) to provide the C2 ester derivative 5. Again, the C13 TMS group may then be removed using HF.

Scheme 2

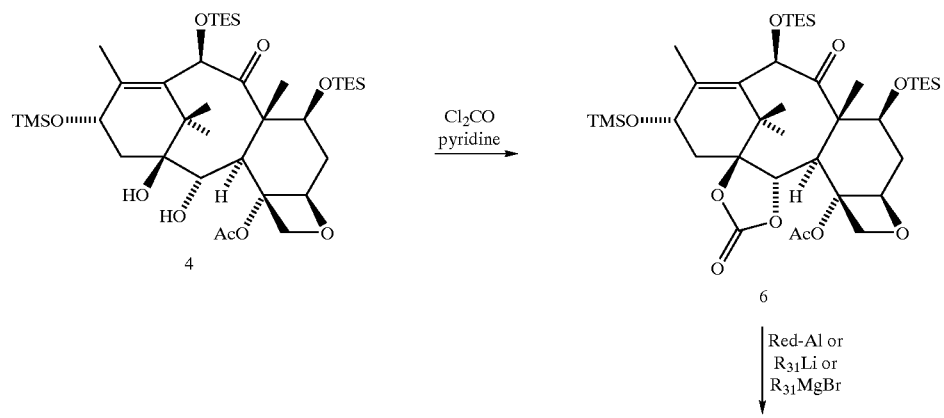

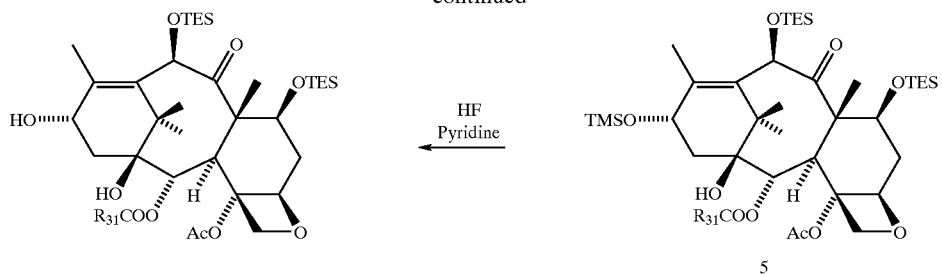

10-DAB analogs having different substituents only at C4, or at both C2 and C4 can be prepared as set forth in Reaction Schemes 3–6.

In Reaction Scheme 3, protected 10-DAB 3 is converted to the triol 7 with lithium aluminum hydride. Triol 7 is then converted to the corresponding C2 ester using $Cl_2CO$ in pyridine followed by a nucleophilic agent (e.g., Grignard reagents or alkyllithium reagents).

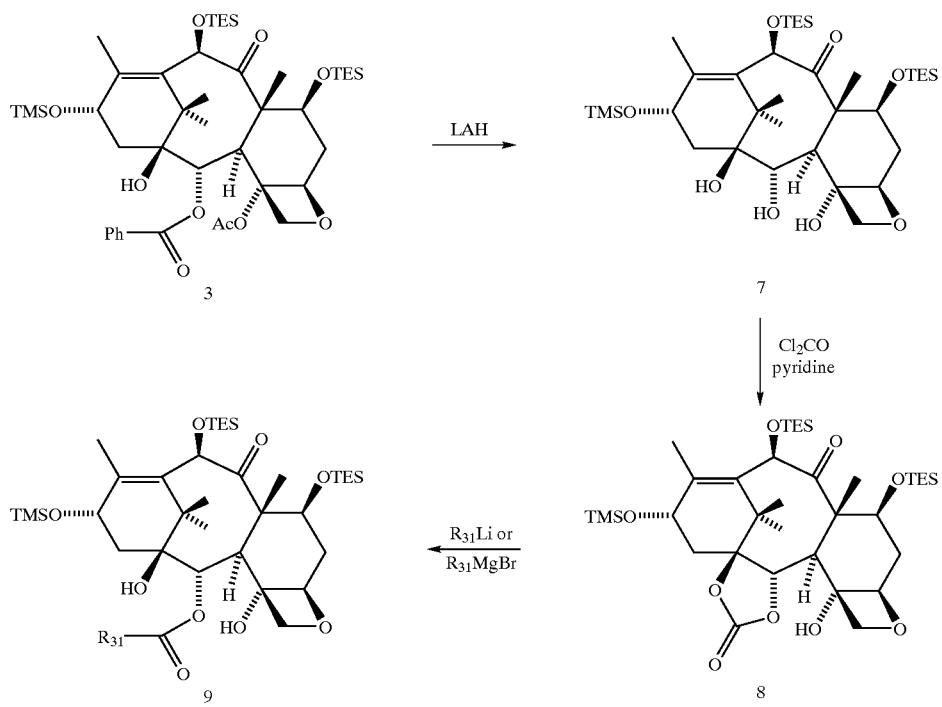

Alternatively, protected 10-DAB 3 may be converted directly to the C2 ester by treating 10-DAB 3 with lithiumtriethylborohydride which selectively cleaves the C4 acetyl group. Also, deprotonation of triol 7 with LDA followed by introduction of an acid chloride selectively gives the C4 ester. For example, when acetyl chloride was used, triol 7 was converted to 1,2 diol 4 as set forth in Reaction Scheme 4.

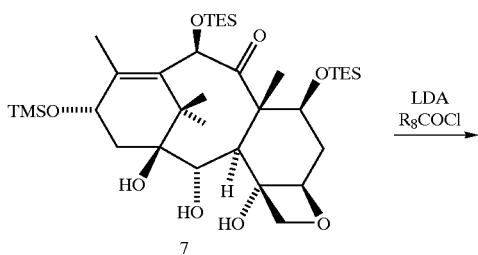

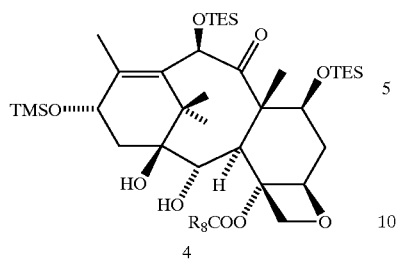

5

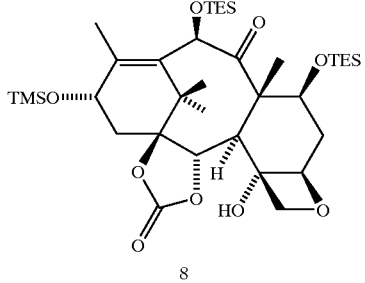

Triol 7 can also readily be converted to the 1,2 carbonate 8. Acetylation of carbonate 8 under vigorous standard conditions provides carbonate 6 as described in Reaction Scheme 5; addition of alkyllithiums or Grignard reagents to carbonate 6 provides the C2 ester having a free hydroxyl group at C4 as set forth in Reaction Scheme 2. As set forth in Reaction Scheme 6, other C4 substituents can be provided by reacting carbonate 8 with an acid chloride and a tertiary amine to yield carbonate 10 which is then reacted with alkyllithiums or Grignard reagents to provide 10-DAB derivatives having new substituents at C2 as set forth in Reaction Scheme 6.

Scheme 5

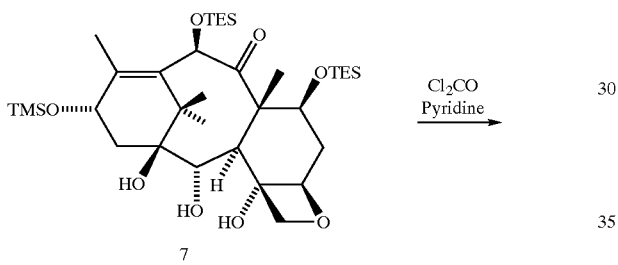

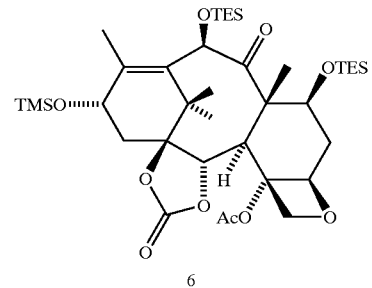

Scheme 6

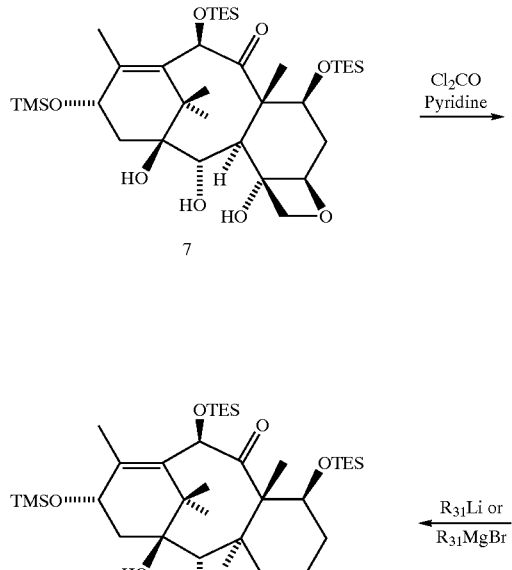

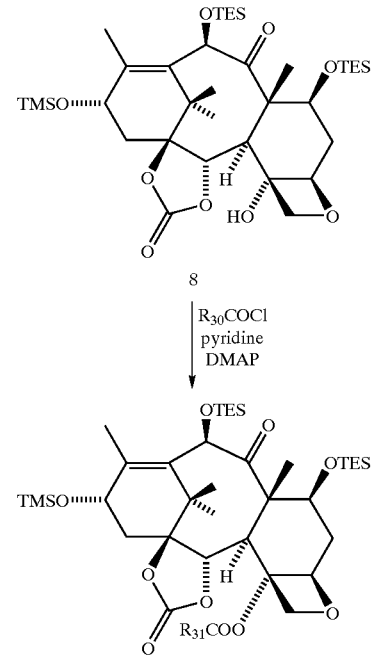

Taxanes having alternative acyloxy C2 and C10 substituents may be prepared as set forth in Reaction Scheme 7, using, for example, baccatin III as a starting material. After being protected at C7 and C13, baccatin III is reduced with LAH to produce 1,2,4,10 tetraol 12. Tetraol 12 is converted to carbonate 13 using $Cl_2CO$ and pyridine, and carbonate 13 is acylated at C10 with an acid chloride and pyridine to produce carbonate 14 (as shown) or with acetic anhydride and pyridine (not shown). Acetylation of carbonate 14 under vigorous standard conditions provides carbonate 15 which is then reacted with alkyl lithiums to provide the baccatin III derivatives having new substituents at C2 and C10.

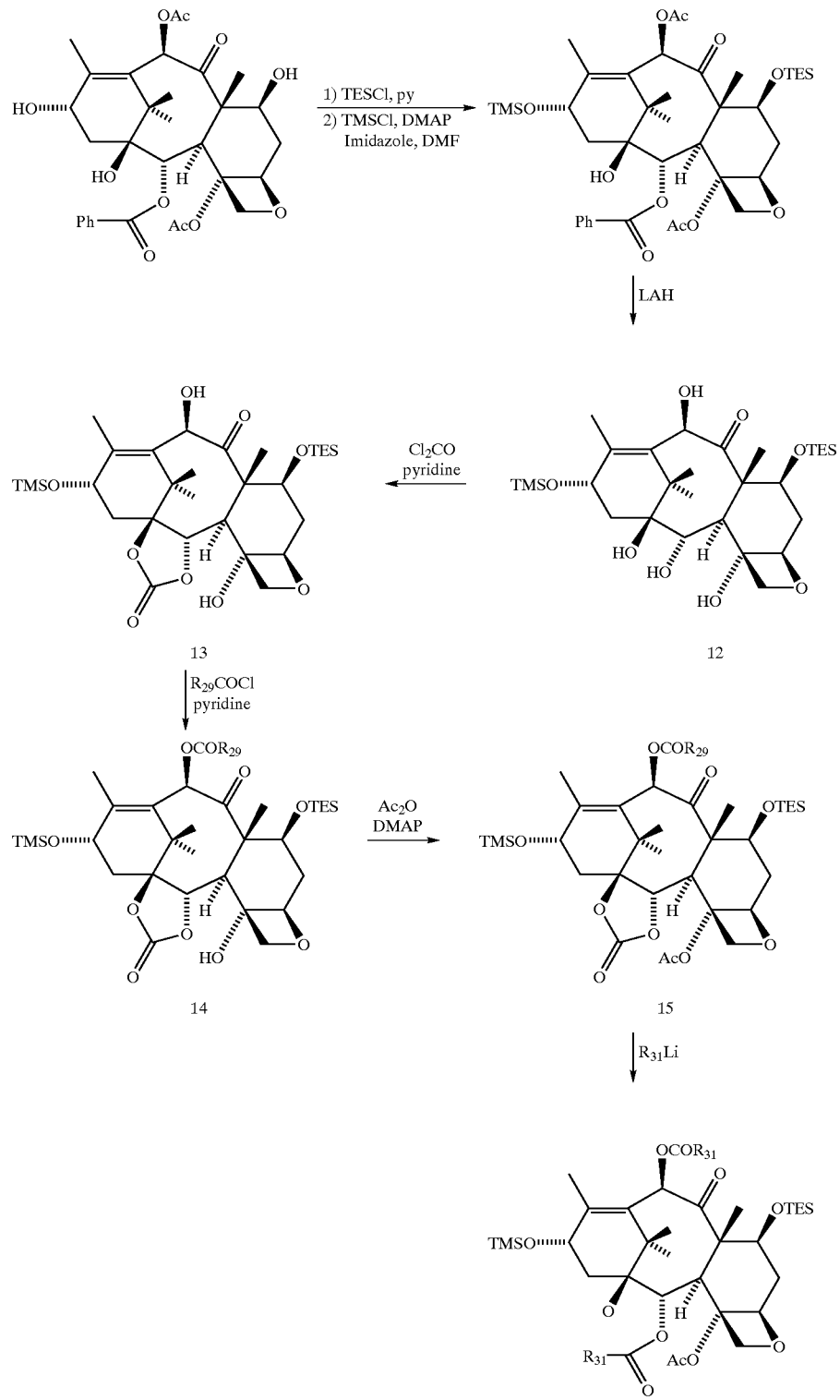

Scheme 7

10-desacetoxy derivatives of baccatin III and 10-desoxy derivatives of 10-DAB having alternative C2 and C4 substituents may be produced using the same reactions (except for the protection of the C10 hydroxy group with TES) by simply replacing 10-DAB with 10-desacetoxy baccatin III as the starting material in Reaction Schemes 1–6. Baccatin III and 10-DAB may be selectively and nearly quantitatively converted to the corresponding 10-desacetoxy or 10-desoxytaxane when they are reacted with samarium diiodide. Alternatively, the 10-DAB derivatives having alternative C2 and C4 substituents may themselves be reacted with samarium diiodide to yield the corresponding 10-deacetoxy compound.

As illustrated in Reaction Scheme 8, the reaction of baccatin III with $Bu_4NBH_4$ in methylene chloride yields 9-desoxo-9β-hydroxybaccatin III 5. After the C7 hydroxy group is protected with the triethylsilyl protecting group, for example 7-protected-9β-hydroxy derivative 6 may be used as a starting material in Reaction Schemes 1–7.

REACTION SCHEME 8

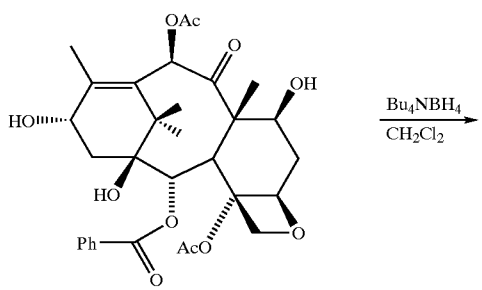

-continued

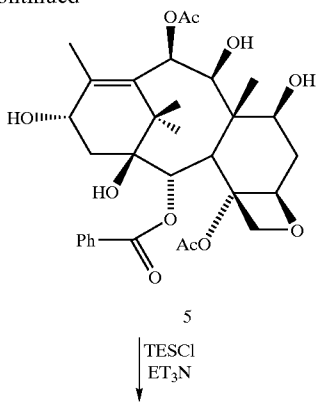

5

|TESCl
|ET$_3$N

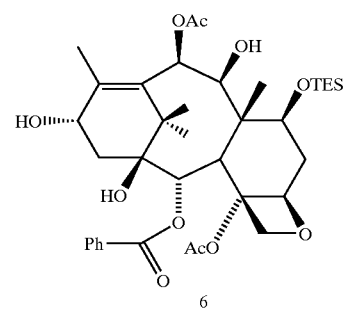

6

Alternatively, the C13 hydroxy group of 7-protected-9β-hydroxy derivative 6 may be protected with trimethylsilyl or other protecting group which can be selectively removed relative to the C7 hydroxy protecting group as illustrated in Reaction Scheme 9, to enable further selective manipulation of the various substituents of the taxane. For example, reaction of 7,13-protected-9β-hydroxy derivative 7 with KH causes the acetate group to migrate from C10 to C9 and the hydroxy group to migrate from C9 to C10, thereby yielding 10-desacetyl derivative 8. Protection of the C10 hydroxy group of 10-desacetyl derivative 8 with triethylsilyl yields derivative 9. Selective removal of the C13 hydroxy protecting group from derivative 9 yields derivative 10 which may be used as a starting material in Reaction Schemes 1–7.

REACTION SCHEME 9

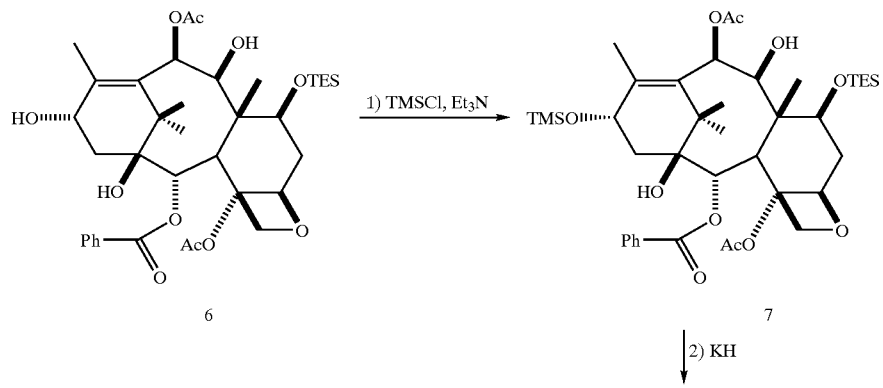

2) KH

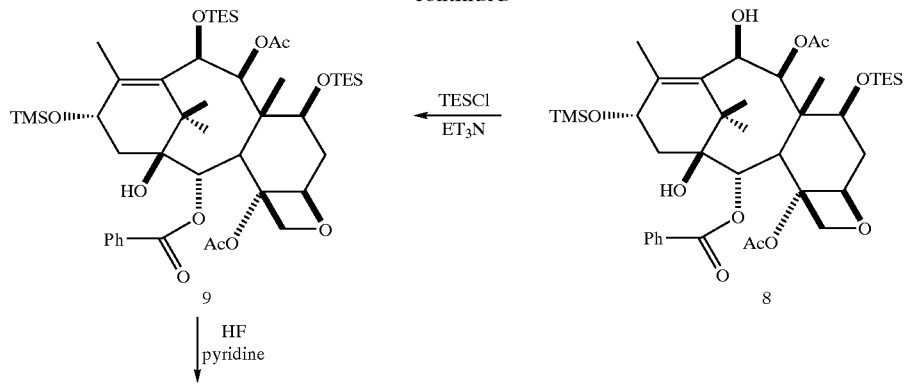

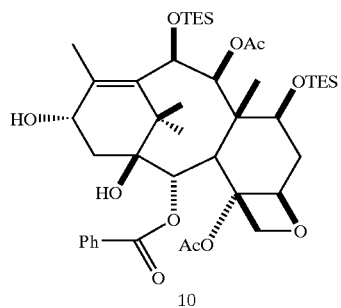

As shown in Reaction Scheme 10, 10-oxo derivative 11 can be provided by oxidation of 10-desacetyl derivative 8. Thereafter, the C13 hydroxy protecting group can be selectively removed followed by attachment of a side chain as described above to yield 9-acetoxy-10-oxo-taxol or other 9-acetoxy-10-oxotetracylic taxanes having a C13 side chain. Alternatively, the C9 acetate group can be selectively removed by reduction of 10-oxo derivative 11 with a reducing agent such as samarium diiodide to yield 9-desoxo-10-oxo derivative 12 which can be used as a starting material for Reaction Schemes 1–7.

REACTION SCHEME 10

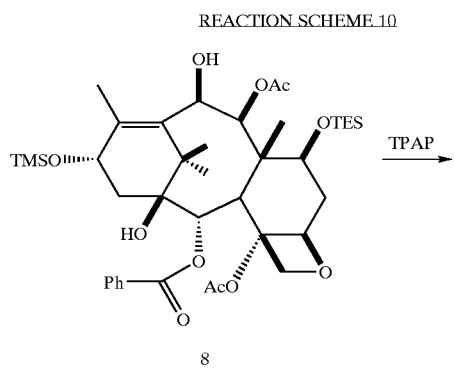

-continued

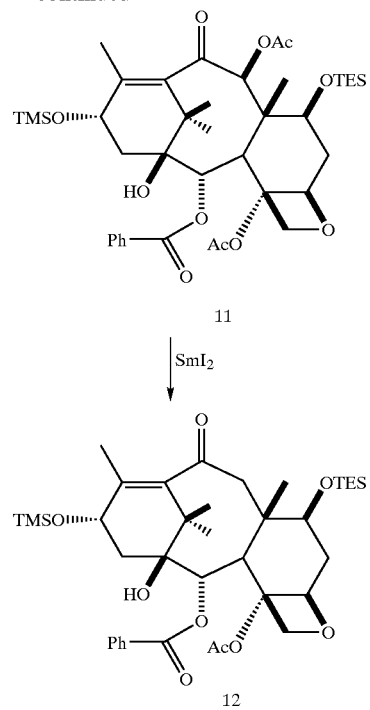

Reaction Scheme 11 illustrates a reaction in which 10-DAB is reduced to yield pentaol 13. The C7 and C10 hydroxyl groups of pentaol 13 can then be selectively protected with the triethylsilyl or another protecting group to produce triol 14 which a can be used as a starting material for Reaction Schemes 1–7 above.

REACTION SCHEME 11

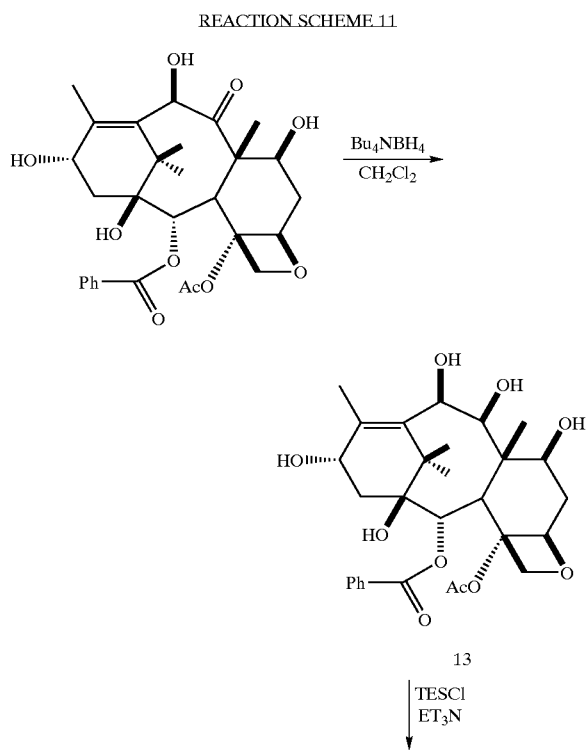
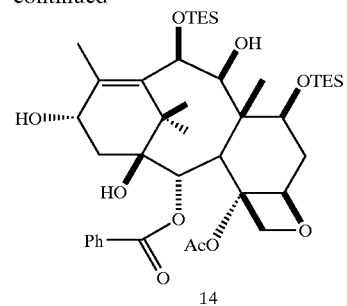

Taxanes having C9 and/or C10 ayloxy substituents other than acetate can be prepared using 10-DAB as a starting material as illustrated in Reaction Scheme 12. Reaction of 10-DAB with triethylsilyl chloride in pyridine yields 7-protected 10-DAB 15. The C10 hydroxy substituent of 7-protected 10-DAB 15 may then be readily acylated with any standard acylating agent to yield derivative 16 having a new C10 acyloxy substituent. Selective reduction of the C9 keto substituent of derivative 16 yields 9B-hydroxy derivative 17 to which a C13 side chain may be attached. Alternatively, the C10 and C9 groups can be caused to migrate as set forth in Reaction Scheme 9, above.

REACTION SCHEME 12

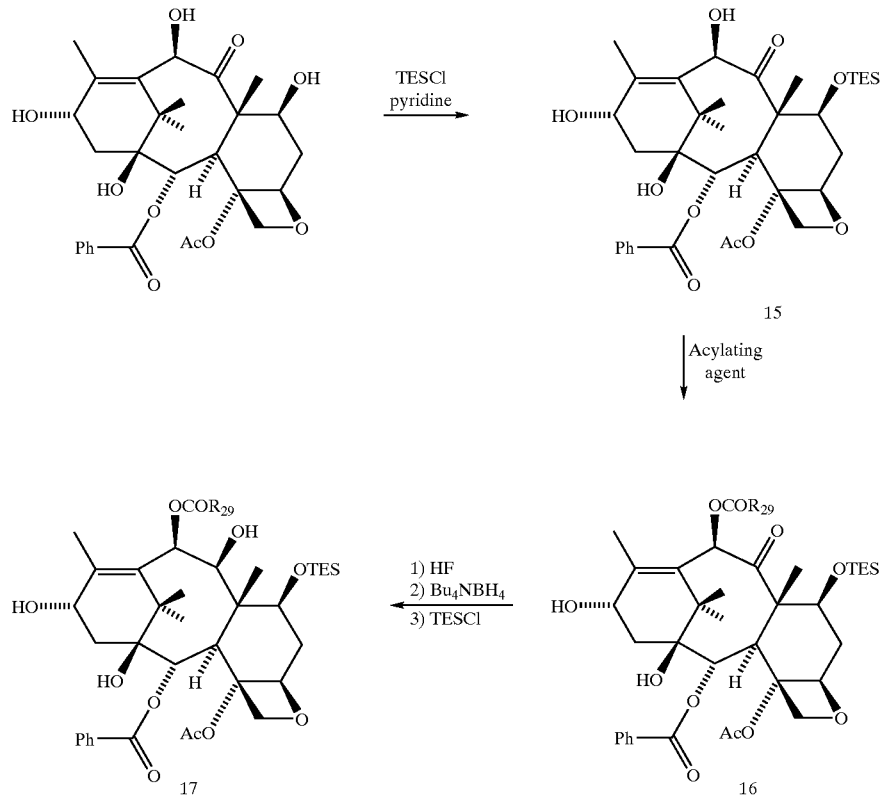

10-desacetoxy derivatives of baccatin III and 10-desoxy derivatives of 10-DAB may be prepared by reacting baccatin III or 10-DAB (or their derivatives) with samarium diiodide. Reaction between the tetracyclic taxane having a C10 leaving group and samarium diiodide may be carried out at 0° C. in a solvent such as tetrahydrofuran. Advantageously, the samarium diiodide selectively abstracts the C10 leaving group; C13 side chains and other substituents on the tetracyclic nucleus remain undisturbed. Thereafter, the C9 keto substituent may be reduced to provide the corresponding 9-desoxo-9β-hydroxy-10-desacetyoxy or 10-desoxy derivatives as otherwise described herein.

C7 dihydro and other C7 substituted taxanes can be prepared as set forth in Reaction Schemes 13, 14 and 14a.

REACTION SCHEME 14

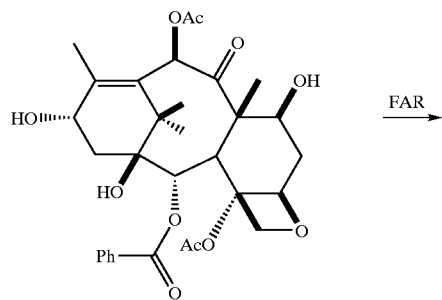

REACTION SCHEME 13

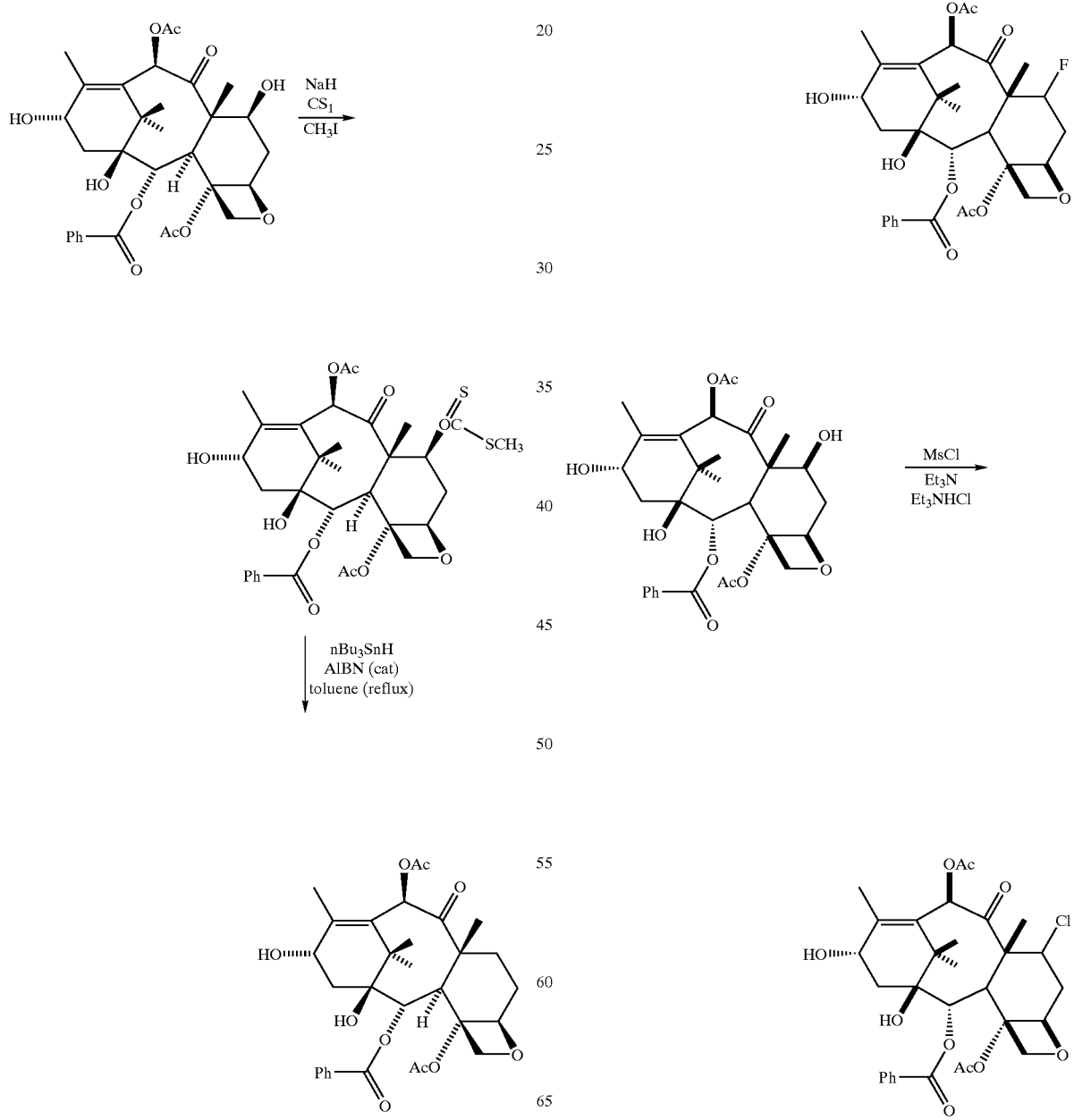

REACTION SCHEME 14a

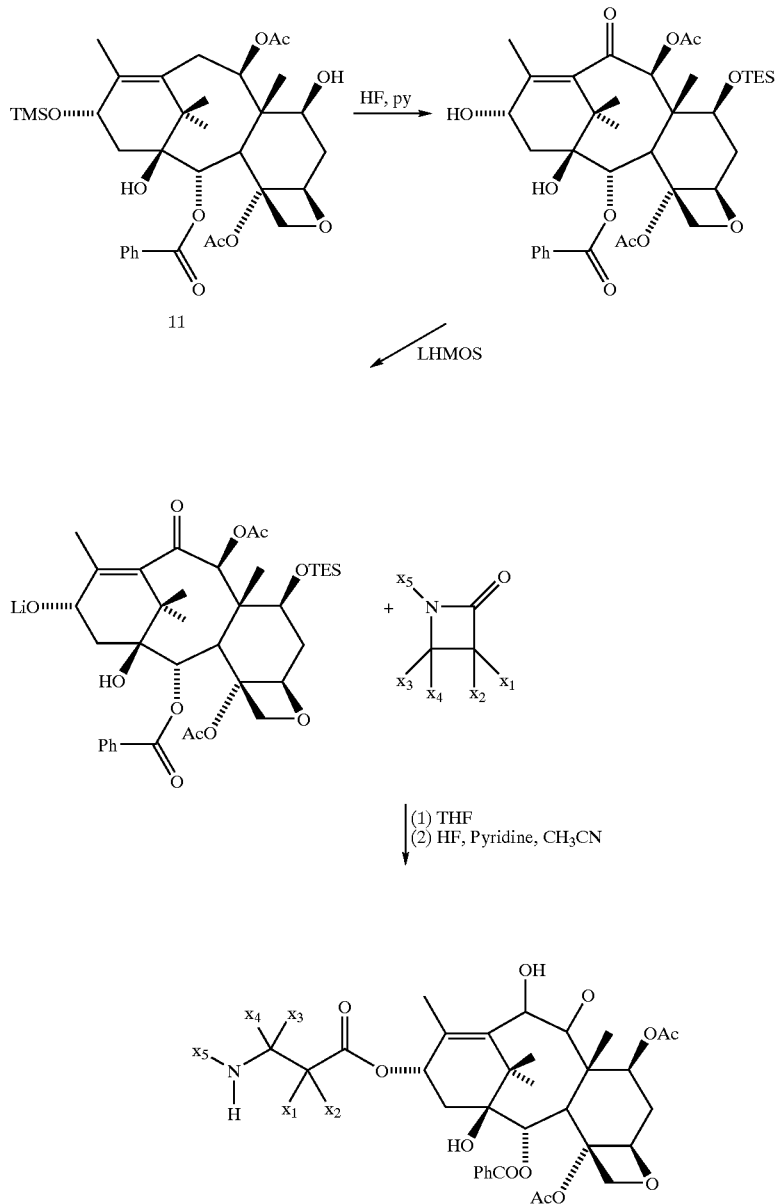

As shown in Reaction Scheme 14, Baccatin III may be converted into 7-fluoro baccatin III by treatment with FAR at room temperature in THF solution. Other baccatin derivatives with a free C7 hydroxyl group behave similarly. Alternatively, 7-chloro baccatin III can be prepared by treatment of baccatin III with methane sulfonyl chloride and triethylamine in methylene chloride solution containing an excess of triethylamine hydrochloride.

Taxanes having C7 acyloxy substituents can be prepared as set forth in Reaction Scheme 14a, 7,13-protected 10-oxo-derivative 11 is converted to its corresponding C13 alkoxide by selectively removing the C13 protecting group and replacing it with a metal such as lithium. The alkoxide is then reacted with a β-lactam or other side chain precursor. Subsequent hydrolysis of the C7 protecting groups causes a migration of the C7 hydroxy substituent to C10, migration of the C10 oxo substituent to C9, and migration of the C9 acyloxy substituent to C7.

A wide variety of tricyclic taxanes are naturally occurring, and through manipulations analogous to those described herein, an appropriate side chain can be attached to the C13 oxygen of these substances. Alternatively, as shown in Reaction Scheme 15, 7-O-triethylsilyl baccatin III can be converted to a tricyclic taxane through the action of trimethyloxonium tetrafluoroborate in methylene chloride solution. The product diol then reacts with lead tetraacetate to provide the corresponding C4 ketone.

REACTION SCHEME 15

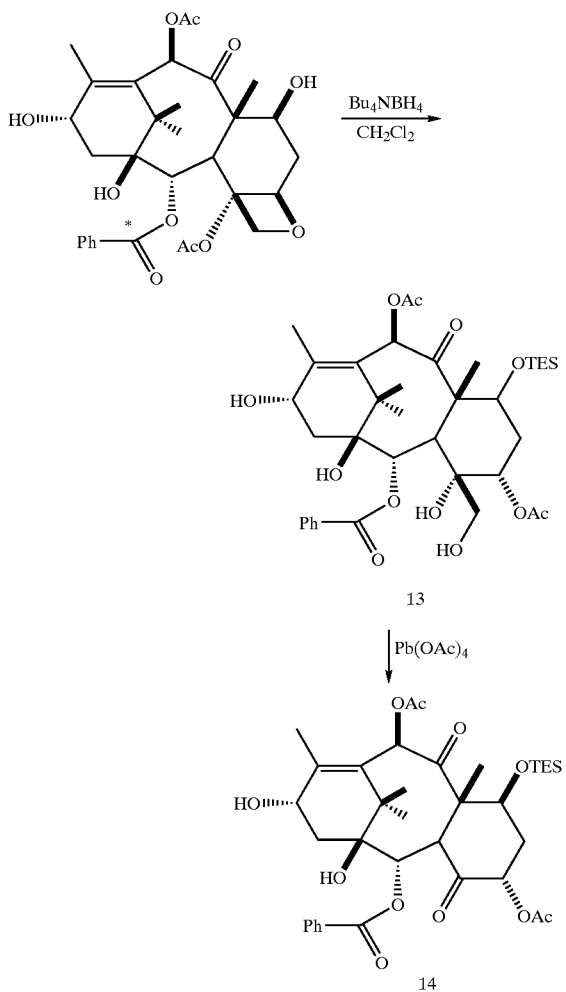

Recently a hydroxylated taxane (14-hydroxy-10-deacetylbaccatin III) has been discovered in an extract of yew needles (C&EN, p 36–37, Apr. 12, 1993). Derivatives of this hydroxylated taxane having the various C2, C4, etc. functional groups described above may also be prepared by using this hydroxylated taxane. In addition, the C14 hydroxy group together with the C1 hydroxy group of 10-DAB can be converted to a 1,2-carbonate as described in C&EN or it may be converted to a variety of esters or other functional groups as otherwise described herein in connection with the C2, C4, C7, C9, C10 and C13 substituents.

Synthesis of tetracyclic taxanes having a C13 side-chain and different substituents at C2 and/or C4 can readily be prepared from baccatin III and 10-DAB derivatives having different substituents at C2 and/or C4 using presently known methods. For instance, a suitable side chain may be attached to a baccatin III or 10-DAB derivative as set forth in U.S. Pat. Nos. 4,924,011 and 4,924,012 or by the reaction of a β-lactam and a suitably protected baccatin III or 10-desacetylbaccatin III derivative as illustrated in Reaction Scheme 14a wherein $X_1$–$X_5$ are as follows:

$X_1$ is —$OX_6$, —$SX_7$, or —$NX_8X_9$;

$X_2$ is hydrogen, alkyl, alkenyl, alkynyl, aryl, or heteroaryl;

$X_3$ and $X_4$ are independently hydrogen, alkyl, alkenyl, alkynyl, aryl, or heteroaryl;

$X_5$ is —$COX_{10}$, —$COOX_{10}$, —$COSX_{10}$, —$CONX_8X_{10}$, or —$SO_2X_{11}$;

$X_6$ is hydrogen, alkyl, alkenyl, alkynyl, aryl, heteroaryl, hydroxy protecting group, or a functional group which increases the water solubility of the taxane derivative;

$X_7$ is alkyl, alkenyl, alkynyl, aryl, heteroaryl, or sulfhydryl protecting group;

$X_8$ is hydrogen, alkyl, alkenyl, alkynyl, aryl, heteroaryl, or heterosubstituted alkyl, alkenyl, alkynyl, aryl or heteroaryl;

$X_9$ is an amino protecting group;

$X_{10}$ is alkyl, alkenyl, alkynyl, aryl, heteroaryl, or heterosubstituted alkyl, alkenyl alkynyl, aryl or heteroaryl;

$X_{11}$ is alkyl, alkenyl, alkynyl, aryl, heteroaryl, —$OX_{10}$, or —$NX_8X_{14}$; and $X_{14}$ is hydrogen, alkyl, alkenyl, alkynyl, aryl, or heteroaryl.

The following examples are provided to more fully illustrate the invention.

EXAMPLE 1

(64-4)

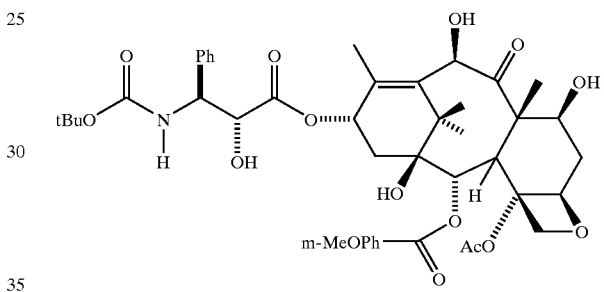

Preparation of 2-Desbenzoyl-2-(3-methoxybenzoyl)-10-deacetyl-N-desbenzoyl-N-(t-butoxycarbonyl) Taxol To a solution of 2-desbenzoyl-2-(3-methoxybenzoyl)-10-deacetyl-7,10-bis(triethylsilyl) baccatin III (48.2 mg, 0.060 mmol) in 0.5 mL of THF at −45° C. was added dropwise 0.066 mL of a 1.00 M solution of LiN(SiMe₃)₂ in hexane. After 0.5 h at −45° C., a solution of cis-1-(t-butoxycarbonyl)-3-triethylsilyloxy-4-phenylazetidin-2-one (90 mg, 0.240 mmol) in 0.5 mL of THF was added dropwise to the mixture. The solution was warmed to 0° C. and kept at that temperature for 1 h before 0.5 mL of a 10% solution of AcOH in THF was added. The mixture was partitioned between saturated aqueous NaHCO₃ and 60/40 ethyl acetate/hexane. Evaporation of the organic layer gave a residue which was purified by filtration through silica gel to give 70.8 mg of a mixture containing (2'R,3'S)-2',7,10-tris (triethylsilyl)-2-desbenzoyl-2-(3-methoxybenzoyl)-10-deacetyl-N-debenzoyl-N-(t-butoxycarbonyl) taxol and a very small amount of the (2'S,3'R) isomer.

To a solution of 70.8 mg of the mixture obtained from the previous reaction in 4 mL of acetonitrile and 0.19 mL of pyridine at 0° C. was added 0.52 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 50.3 mg of material which was purified by recrystallization to give 43.1 mg (86%) of 2-desbenzoyl-2-(3-methoxybenzoyl)-10-deacetyl-N-debenzoyl-N-(t-butoxycarbonyl) taxol.

m.p. 162–164° C.; $[\alpha]^{25}_{Na}$ −61.6° (c 0.790, CHCl$_3$). $^1$H NMR (CDCl$_3$, 300 MHz) δ 7.67 (m, 2H, methoxybenzoate, ortho), 7.36 (m, 6H, aromatic), 7.15 (m, 1H, methoxybenzoate), 6.19 (m, 1H, H13), 5.65 (d, J=6.9 Hz, 1H, H2β), 5.50 (m, 1H, NH), 5.21 (m, 2H, H3', H10), 4.95 (dd, J=7.8, 1.8 Hz, 1H, H5), 4.60 (m, 1H, H2'), 4.33 (d, J=8.7 Hz, 1H, H20α), 4.23 (m, 1H, H7), 4.17 (d, J=8.7 Hz, 1H, H20β), 3.89 (d, J=6.9 Hz, 1H, H3), 3.86 (s, 3H, methoxy), 3.56 (m, 1H, 2'OH), 2.55 (m, 1H, H6α), 2.34 (s, 3H, 4Ac), 2.23 (m, 2H, H14), 1.83 (s, 3H, Me18), 1.79 (m, 1H, H6β), 1.73 (s, 3H, Me19), 1.32 (s, 9H, t-butyl), 1.22 (s, 3H, Me17), 1.11 (s, 3H, Me16).

EXAMPLE 2

(65-1)

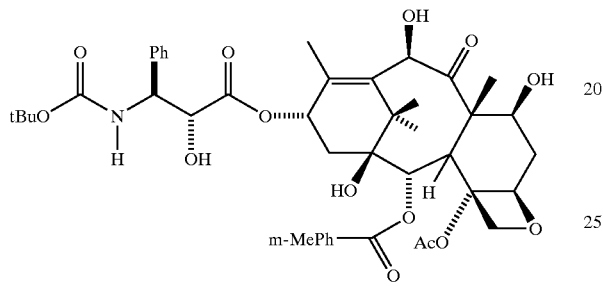

Preparation of 2-Desbenzoyl-2-(3-methylbenzoyl)-10-deacetyl-N-desbenzoyl-N-(t-butoxycarbonyl) Taxol To a solution of 2-desbenzoyl-2-(3-methylbenzoyl)-10-deacetyl-7,10-bis(triethylsilyl) baccatin III (47.2 mg, 0.060 mmol) in 0.5 mL of THF at −45° C. was added dropwise 0.066 mL of a 1.00 M solution of LiN(SiMe$_3$)$_2$ in hexane. After 0.5 h at −45° C., a solution of cis-1-(t-butoxycarbonyl)-3-triethylsilyloxy-4-phenylazetidin-2-one (90 mg, 0.240 mmol) in 0.5 mL of THF was added dropwise to the mixture. The solution was warmed to 0° C. and kept at that temperature for 1 h before 0.5 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 70.0 mg of a mixture containing (2'R,3'S)-2',7,10-tris(triethylsilyl)-2-desbenzoyl-2-(3-methyl-benzoyl)-10-deacetyl-N-desbenzoyl-N-(t-butoxycarbonyl) taxol and a very small amount of the (2'S,3'R) isomer.

To a solution of 70.0 mg of the mixture obtained from the previous reaction in 4 mL of acetonitrile and 0.19 mL of pyridine at 0° C. was added 0.52 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 49.3 mg of material which was purified by recrystallization to give 41.9 mg (85%) of 2-desbenzoyl-2-(3-methylbenzoyl)-10-deacetyl-N-desbenzoyl-N-(t-butoxycarbonyl) taxol.

m.p. 169–171° C.; $[\alpha]^{25}_{Na}$ −60.4° (c 0.510, CHCl$_3$). $^1$H NMR (CDCl$_3$, 300 MHz) δ 7.91 (m, 2H, benzoate), 7.38 (m, 7H, aromatic), 6.21 (m, 1H, H13), 5.65 (d, J=7.2 Hz, 1H, H2β), 5.42 (m, 1H, NH), 5.26 (m, 1H, H3'), 5.20 (d, J=1.2 Hz, 1H, H10), 4.94 (m, 1H, H5), 4.61 (m, 1H, H2'), 4.31 (d, J=8.7 Hz, 1H, H20α), 4.24 (m, 1H, H7), 4.17 (d, J=8.7 Hz, 1H, H20β), 3.91 (d, J=7.2 Hz, 1H, H3), 3.37 (m, 1H, 2'OH), 2.57 (m, 1H, H6α), 2.43 (s, 3H, 4Ac), 2.26 (m, 2H, H14), 2.17 (s, 3H, methylbenzoate), 1.84 (s, 3H, Me18), 1.79 (m, 1H, H6β), 1.74 (s, 3H, Me19), 1.33 (s, 9H, t-butyl), 1.22 (s, 3H, Me17), 1.12 (s, 3H, Me16).

EXAMPLE 3

(65-2)

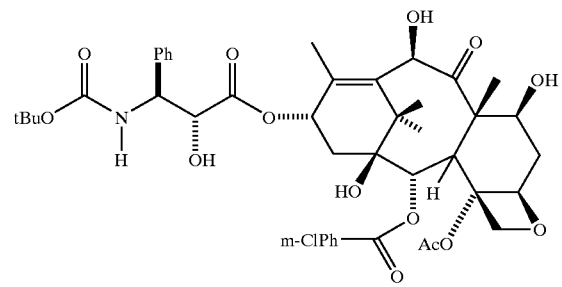

Preparation of 2-Desbenzoyl-2-(3-chlorobenzoyl)-10-deacetyl-N-desbenzoyl-N-(t-butoxycarbonyl) Taxol To a solution of 2-desbenzoyl-2-(3-chlorobenzoyl)-10-deacetyl-7,10-bis(triethylsilyl) baccatin III (48.4 mg, 0.060 mmol) in 0.5 mL of THF at −45° C. was added dropwise 0.066 mL of a 1.00 M solution of LiN(SiMe$_3$)$_2$ in hexane. After 0.5 h at −45° C., a solution of cis-1-(t-butoxycarbonyl)-3-triethylsilyloxy-4-phenylazetidin-2-one (90 mg, 0.240 mmol) in 0.5 mL of THF was added dropwise to the mixture. The solution was warmed to 0° C. and kept at that temperature for 1 h before 0.5 mL of a 10% solution of ACOH in THF was added. The mixture was partitioned between saturated aqueous NaHCO$_3$ and 60/40 ethyl acetate/hexane. Evaporation of the organic layer gave a residue which was purified by filtration through silica gel to give 71 mg of a mixture containing (2'R,3'S)-2',7,10-tris(triethylsilyl)-2-desbenzoyl-2-(3-chlorobenzoyl)-10-deacetyl-N-desbenzoyl-N-(t-butoxycarbonyl) taxol and a very small amount of the (2'S,3'R) isomer.

To a solution of 71 mg of the mixture obtained from the previous reaction in 4 mL of acetonitrile and 0.19 mL of pyridine at 0° C. was added 0.52 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 50.5 mg of material which was purified by recrystallization to give 40.4 mg (80%) of 2-desbenzoyl-2-(3-chlorobenzoyl)-10-deacetyl-N-desbenzoyl-N-(t-butoxycarbonyl) taxol.

m.p. 149–150° C.; $[\alpha]^{25}_{Na}$ −53.3° (c 0.510, CHCl$_3$). $^1$H NMR (CDCl$_3$, 300 MHz) δ 8.11 (br s, 1H, chlorobenzoate ortho), 7.98 (d, J=7.5 Hz, 1H, chlorobenzoate ortho), 7.59 (m, 1H, chlorobenzoate), 7.45 (t, J=7.5 Hz, 1H, chlorobenzoate), 7.38 (m, 5H, aromatic), 6.18 (m, 1H, H13), 5.62 (d, J=7.2 Hz, 1H, H2β), 5.41 (m, 1H, H3'), 5.24 (m, 1H, NH), 5.20 (d, J=1.0 Hz, 1H, H10), 4.95 (dd, J=9.3, 1.2 Hz, 1H, H5), 4.59 (m, 1H, H2'), 4.30 (d, J=8.4 Hz, 1H, H20α), 4.23 (m, 1H, H7), 4.15 (d, J=8.4 Hz, 1H, H20β), 3.91 (d, J=7.2 Hz, 1H, H3), 3.35 (m, 1H, 2'OH), 2.58 (m, 1H, H6α), 2.36 (s, 3H, 4Ac), 2.24 (m, 2H, H14), 1.84 (s, 3H, Me18), 1.79 (m, 1H, H6β), 1.75 (s, 3H, Me19), 1.34 (s, 9H, t-butyl), 1.23 (s, 3H, Me17), 1.12 (s, 3H, Me16).

EXAMPLE 4

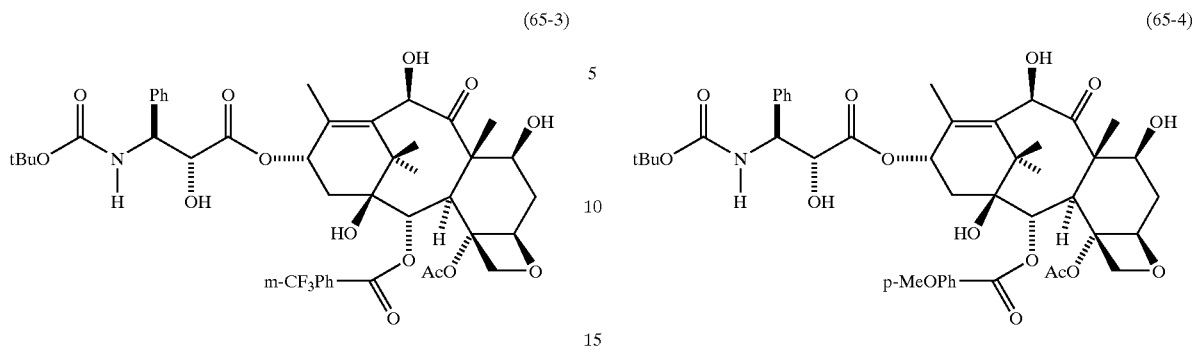

Preparation of 2-Desbenzoyl-2-(3-trifluoromethylbenzoyl)-10-deacetyl-N-desbenzoyl-N-(t-butoxycarbonyl) Taxol To a solution of 2-desbenzoyl-2-(3-trifluoromethylbenzoyl)-10-deacetyl-7,10-bis(triethylsilyl) baccatin III (50.4 mg, 0.060 mmol) in 0.5 mL of THF at −45° C. was added dropwise 0.066 mL of a 1.00 M solution of LiN(SiMe$_3$)$_2$ in hexane. After 0.5 h at −45° C., a solution of cis-1-(t-butoxycarbonyl)-3-triethylsilyloxy-4-phenylazetidin-2-one (90 mg, 0.240 mmol) in 0.5 mL of THF was added dropwise to the mixture. The solution was warmed to 0° C. and kept at that temperature for 1 h before 0.5 mL of a 10% solution of ACOH in THF was added. The mixture was partitioned between saturated aqueous NaHCO$_3$ and 60/40 ethyl acetate/hexane. Evaporation of the organic layer gave a residue which was purified by filtration through silica gel to give 73.0 mg of a mixture containing (2'R,3'S)-2',7,10-tris(triethylsilyl)-2-desbenzoyl-2-(3-trifluoromethylbenzoyl)-10-deacetyl-N-desbenzoyl-N-(t-butoxycarbonyl) taxol and a very small amount of the (2'S,3'R) isomer.

To a solution of 73.0 mg of the mixture obtained from the previous reaction in 4 mL of acetonitrile and 0.19 mL of pyridine at 0° C. was added 0.52 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 52.6 mg of material which was purified by recrystallization to give 41.0 mg (78%) of 2-desbenzoyl-2-(3-trifluoromethylbenzoyl)-10-deacetyl-N-desbenzoyl-N-(t-butoxycarbonyl) taxol.

m.p. 140–142° C.; $[\alpha]^{25}_{Na}$ −50.4° (c 1.055, CHCl$_3$). $^1$H NMR (CDCl$_3$, 300 MHz) δ 8.43 (s, 1H, benzoate, ortho), 8.29 (d, J=7.8 Hz, 1H, benzoate ortho), 7.88 (d, J=7.8 Hz, 1H, benzoate), 7.66 (t, J=7.8 Hz, 1H, benzoate), 7,38 (m, 5H, aromatic), 6.17 (m, 1H, H13), 5.65 (d, J=7.2 Hz, 1H, H2β), 5.38 (m, 1H, NH), 5.23 (m, 1H, H3'), 5.21 (d, J=1.8 Hz, 1H, H10), 4.95 (m, 1H, H5), 4.58 (m, 1H, H2'), 4.27 (d, J=8.7 Hz, 1H, H20α), 4.21 (m, 1H, H7), 4.15 (d, J=8.7 Hz, 1H, H20β), 3.93 (d, J=7.2 Hz, 1H, H3), 3.35 (m, 1H, 2'OH), 2.59 (m, 1H, H6α), 2.33 (s, 3H, 4Ac), 2.23 (m, 2H, H14), 1.85 (s, 3H, Me18), 1.79 (m, 1H, H6β), 1.76 (s, 3H, Me19), 1.32 (s, 9H, t-butyl), 1.22 (s, 3H, Me17), 1.11 (s, 3H, Me16).

EXAMPLE 5

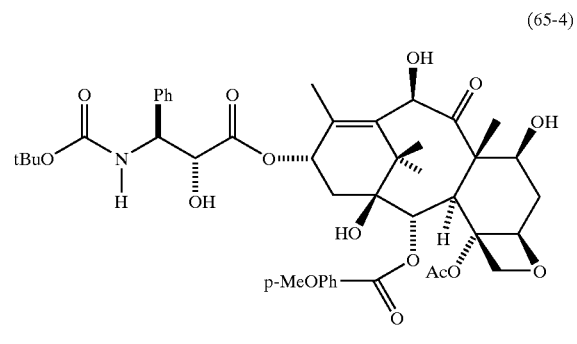

Preparation of 2-Desbenzoyl-2-(4-methoxybenzoyl)-10-deacetyl-N-desbenzoyl-N-(t-butoxycarbonyl) Taxol To a solution of 2-desbenzoyl-2-(4-methoxy-benzoyl)-10-deacetyl-7,10-bis(triethylsilyl) baccatin III (48.2 mg, 0.060 mmol) in 0.5 mL of THF at −45° C. was added dropwise 0.066 mL of a 1.00 M solution of LiN(SiMe$_3$)$_2$ in hexane. After 0.5 h at −45° C., a solution of cis-1-(t-butoxycarbonyl)-3-triethylsilyloxy-4-phenylazetidin-2-one (90 mg, 0.240 mmol) in 0.5 mL of THF was added dropwise to the mixture. The solution was warmed to 0° C. and kept at that temperature for 1 h before 0.5 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 71 mg of a mixture containing (2'R,3'S)-2',7,10-tris(triethylsilyl)-2-desbenzoyl-2-(4-methoxybenzoyl)-10-deacetyl-N-desbenzoyl-N-(t-butoxycarbonyl) taxol and a very small amount of the (2'S,3'R) isomer.

To a solution of 71 mg of the mixture obtained from the previous reaction in 4 mL of acetonitrile and 0.19 mL of pyridine at 0° C. was added 0.52 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 50.3 mg of material which was purified by recrystallization to give 45.2 mg (90%) of 2-desbenzoyl-2-(4-methoxybenzoyl)-10-deacetyl-N-desbenzoyl-N-(t-butoxycarbonyl) taxol.

m.p. 160–162° C.; $[\alpha]^{25}_{Na}$ −47.6° (c 0.290, CHCl$_3$). $^1$H NMR (CDCl$_3$, 300 MHz) δ 8.05 (dd, J=9.0, 2H, methoxybenzoate, ortho), 7,38 (m, 5H, aromatic), 6.96 (dd, J=9.0, 2H, methoxybenzoate, meta), 6.23 (m, 1H, H13), 5.64 (d, J=7.2 Hz, 1H, H2β), 5.42 (m, 1H, H3'), 5.27 (m, 1H, NH), 5.19 (d, J=1.2 Hz, 1H, H10), 4.93 (dd, J=7.8, 1.8 Hz, 1H, H5), 4.62 (m, 1H, H2'), 4.31 (d, J=9.0 Hz, 1H, H20α), 4.24 (m, 1H, H7), 4.19 (d, J=9.0 Hz, 1H, H20β), 3.89 (d, J=7.2 Hz, 1H, H3), 3.65 (s, 3H, methoxy), 3.32 (m, 1H, 2'OH), 2.58 (m, 1H, H6α), 2.37 (s, 3H, 4Ac), 2.26 (m, 2H, H14), 1.85 (s, 3H, Me18), 1.78 (m, 1H, H6β), 1.75 (s, 3H, Me19), 1.34 (s, 9H, t-butyl), 1.23 (s, 3H, Me17), 1.12 (s, 3H, Me16).

EXAMPLE 6

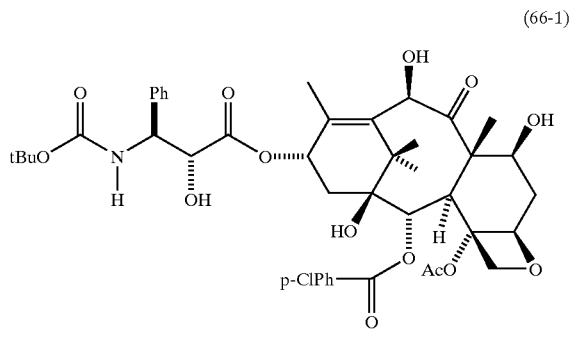

(66-1)

Preparation of 2-Desbenzoyl-2-(4-chlorobenzoyl)-10-deacetyl-N-desbenzoyl-N-(t-butoxycarbonyl) Taxol To a solution of 2-desbenzoyl-2-(4-chlorobenzoyl)-10-deacetyl-7,10-bis(triethylsilyl) baccatin III (48.4 mg, 0.060 mmol) in 0.5 mL of THF at −45° C. was added dropwise 0.066 mL of a 1.00 M solution of LiN(SiMe$_3$)$_2$ in hexane. After 0.5 h at −45° C., a solution of cis-1-(t-butoxycarbonyl)-3-triethylsilyloxy-4-phenylazetidin-2-one (90 mg, 0.240 mmol) in 0.5 mL of THF was added dropwise to the mixture. The solution was warmed to 0° C. and kept at that temperature for 1 h before 0.5 mL of a 10% solution of ACOH in THF was added. The mixture was partitioned between saturated aqueous NaHCO$_3$ and 60/40 ethyl acetate/hexane. Evaporation of the organic layer gave a residue which was purified by filtration through silica gel to give 71 mg of a mixture containing (2'R,3'S)-2',7,10-tris(triethylsilyl)-2-desbenzoyl-2-(4-chlorobenzoyl)-10-deacetyl-N-desbenzoyl-N-(t-butoxycarbonyl) taxol and a very small amount of the (2'S,3'R) isomer.

To a solution of 71 mg of the mixture obtained from the previous reaction in 4 mL of acetonitrile and 0.19 mL of pyridine at 0° C. was added 0.52 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 51 mg of material which was purified by recrystallization to give 37.9 mg (75%) of 2-desbenzoyl-2-(4-chlorobenzoyl)-10-deacetyl-N-desbenzoyl-N-(t-butoxycarbonyl) taxol.

m.p. 160–161° C.; $[\alpha]^{25}_{Na}$ −46.0° (c 0.104, CHCl$_3$). $^1$H NMR (CDCl$_3$, 300 MHz) δ 8.03 (d, J=8.7 Hz, 2H, chlorobenzoate ortho), 7.48 (d, J=8.7 Hz, 2H, chlorobenzoate meta), 7.38 (m, 5H, aromatic), 6.23 (m, 1H, H13), 5.64 (d, J=7.2 Hz, 1H, H2β), 5.45 (m, 1H, H3'), 5.26 (m, 1H, NH), 5.20 (d, J=1.2 Hz, 1H, H10), 4.93 (d, J=7.8 Hz, 1H, H5), 4.63 (m, 1H, H2'), 4.28 (d, J=8.2 Hz, 1H, H20α), 4.22 (m, 1H, H7), 4.15 (d, J=8.2 Hz, 1H, H20β), 3.90 (d, J=7.2 Hz, 1H, H3), 3.36 (m, 1H, 2'OH), 2.58 (m, 1H, H6α), 2.37 (s, 3H, 4Ac), 2.25 (m, 2H, H14), 1.85 (s, 3H, Me18), 1.80 (m, 1H, H6β), 1.75 (s, 3H, Me19), 1.32 (s, 9H, t-butyl), 1.23 (s, 3H, Me17), 1.11 (s, 3H, Me16).

EXAMPLE 7

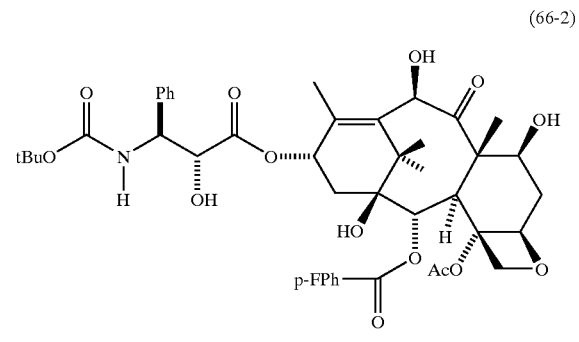

(66-2)

Preparation of 2-Desbenzoyl-2-(4-fluorobenzoyl)-10-deacetyl-N-desbenzoyl-N-(t-butoxycarbonyl) Taxol To a solution of 2-desbenzoyl-2-(4-fluorobenzoyl)-10-deacetyl-7,10-bis(triethylsilyl) baccatin III (47.5 mg, 0.060 mmol) in 0.5 mL of THF at −45° C. was added dropwise 0.066 mL of a 1.00 M solution of LiN(SiMe$_3$)$_2$ in hexane. After 0.5 h at −45 C, a solution of cis-1-(t-butoxycarbonyl)-3-triethylsilyloxy-4-phenylazetidin-2-one (90 mg, 0.240 mmol) in 0.5 mL of THF was added dropwise to the mixture. The solution was warmed to 0° C. and kept at that temperature for 1 h before 0.5 mL of a 10% solution of ACOH in THF was added. The mixture was partitioned between saturated aqueous NaHCO$_3$ and 60/40 ethyl acetate/hexane. Evaporation of the organic layer gave a residue which was purified by filtration through silica gel to give 70 mg of a mixture containing (2'R,3'S)-2',7,10-tris(triethylsilyl)-2-desbenzoyl-2-(4-fluorobenzoyl)-10-deacetyl-N-desbenzoyl-N-(t-butoxycarbonyl) taxol and a very small amount of the (2'S,3'R) isomer.

To a solution of 70 mg of the mixture obtained from the previous reaction in 4 mL of acetonitrile and 0.19 mL of pyridine at 0° C. was added 0.52 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 49.5 mg of material which was purified by recrystallization to give 42.0 mg (85%) of 2-desbenzoyl-2-(4-fluorobenzoyl)-10-deacetyl-N-desbenzoyl-N-(t-butoxycarbonyl) taxol.

m.p. 158–160° C.; $[\alpha]^{25}_{Na}$ −47.6° (c 0.290, CHCl$_3$). $^1$H NMR (CDCl$_3$, 300 MHz) δ 8.13 (m, 2H, fluorobenzoate ortho), 7.38 (m, 5H, aromatic), 7.17 (m, 2H, fluorobenzoate), 6.23 (m, 1H, H13), 5.64 (d, J=7.2 Hz, 1H, H2β), 5.41 (d, J=9.9 Hz, 1H, H3'), 5.26 (m, 1H, NH), 5.20 (d, J=1.2 Hz, 1H, H10), 4.93 (dd, J=9.9, 2.1 Hz, 1H, H5), 4.63 (m, 1H, H2'), 4.28 (d, J=8.2 Hz, 1H, H20α), 4.24 (m, 1H, H7), 4.17 (d, J=8.2 Hz, 1H, H20β), 3.91 (d, J=7.2 Hz, 1H, H3), 3.32 (m, 1H, 2'OH), 2.58 (m, 1H, H6α), 2.37 (s, 3H, 4Ac), 2.25 (m, 2H, H14), 1.85 (s, 3H, Me18), 1.80 (m, 1H, H6β), 1.75 (s, 3H, Me19), 1.33 (s, 9H, t-butyl), 1.25 (s, 3H, Me17), 1.12 (s, 3H, Me16).

EXAMPLE 8

(68-1)

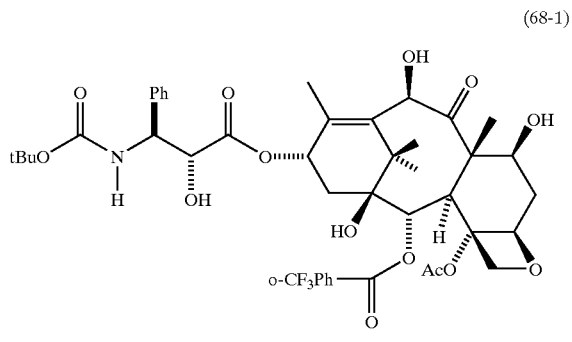

Preparation of N-Desbenzoyl-N-(t-butoxycarbonyl)-2-desbenzoyl-2-(2-trifluoromethylbenzoyl)-10-desacetyl Taxol To a solution of 2-desbenzoyl-2-(2-trifluoromethylbenzoyl)-10-deacetyl-7,10-(bis)-O-triethylsilyl baccatin III (50.4 mg, 0.060 mmol) in 0.5 mL of THF at −45° C. was added dropwise 0.066 mL of a 1.00 M solution of LiN(SiMe$_3$)$_2$ in hexane. After 0.5 h at −45C., a solution of cis-1-(t-butoxycarbonyl)-3-triethylsilyloxy-4-phenylazetidin-2-one (90 mg, 0.240 mmol) in 0.5 mL of THF was added dropwise to the mixture. The solution was warmed to 0° C. and kept at that temperature for 1 h before 0.5 mL of a 10% solution of ACOH in THF was added. The mixture was partitioned between saturated aqueous NaHCO$_3$ and 60/40 ethyl acetate/hexane. Evaporation of the organic layer gave a residue which was purified by filtration through silica gel to give 73.0 mg of a mixture containing (2'R,3'S)-2',7,10-(tris)-O-triethylsilyl-N-desbenzoyl-N-(t-butoxycarbonyl)-2-desbenzoyl-2-(2-trifluoromethylbenzoyl)-10-desacetyl taxol and a very small amount of the (2'S,3'R) isomer.

To a solution of 73.0 mg of the mixture obtained from the previous reaction in 4 mL of acetonitrile and 0.19 mL of pyridine at 0° C. was added 0.52 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 52.6 mg of material which was purified by recrystallization to give 39.4 mg (75%) of N-desbenzoyl-N-(t-butoxycarbonyl)-2-desbenzoyl-2-(2-trifluoromethylbenzoyl)-10-desacetyl taxol.

m.p. 121–123° C.; [α]$^{25}_{Na}$ −34.2° (c 0.760, CHCl$_3$). $^1$H NMR (CDCl$_3$, 300 MHz) δ 8.10 (m, 1H, benzoate, ortho), 7.82 (d, J=7.5 Hz, 1H, benzoate), 7.70 (m, 2H, benzoate), 7.35 (m, 5H, aromatic), 6.24 (m, 1H, H13), 5.64 (d, J=7.2 Hz, 1H, H2β), 5.46 (m, 1H, NH), 5.28 (m, 1H, H3'), 5.19 (d, J=1.8 Hz, 1H, H10), 4.89 (dd, J=8.7, 1.2 Hz, 1H, H5), 4.63 (m, 1H, H2'), 4.26 (d, J=8.1 Hz, 1H, H20α), 4.17 (m, 2H, H7, H20β), 3.90 (d, J=7.2 Hz, 1H, H3), 3.35 (m, 1H, 2'OH), 2.56 (m, 1H, H6α), 2.39 (m, 2H, H14), 2.24 (s, 3H, 4Ac), 1.87 (s, 3H, Me18), 1.84 (m, 1H, H6β), 1.76 (s, 3H, Me19), 1.38 (s, 9H, t-butyl), 1.24 (s, 3H, Me17), 1.11 (s, 3H, Me16).

EXAMPLE 9

(68-2)

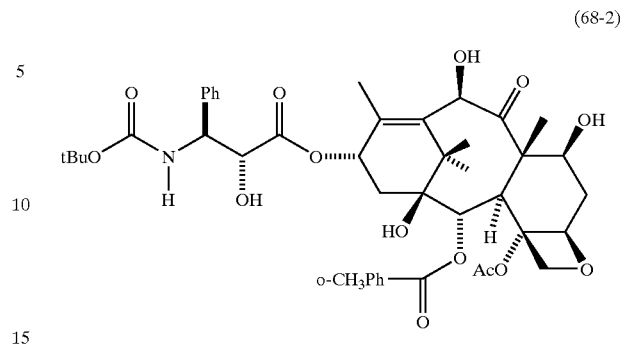

Preparation of N-Desbenzoyl-N-(t-butoxycarbonyl)-2-desbenzoyl-2-(2-methylbenzoyl)-10-desacetyl Taxol To a solution of 2-desbenzoyl-2-(2-methylbenzoyl)-10-desacetyl-7,10-(bis)-O-triethylsilyl baccatin III (47.2 mg, 0.060 mmol) in 0.5 mL of THF at −45° C. was added dropwise 0.066 mL of a 1.00 M solution of LiN(SiMe$_3$)$_2$ in hexane. After 0.5 h at −45° C., a solution of cis-1-(t-butoxycarbonyl)-3-triethylsilyloxy-4-phenylazetidin-2-one (90 mg, 0.240 mmol) in 0.5 mL of THF was added dropwise to the mixture. The solution was warmed to 0° C. and kept at that temperature for 1 h before 0.5 mL of a 10% solution of ACOH in THF was added. The mixture was partitioned between saturated aqueous NaHCO$_3$ and 60/40 ethyl acetate/hexane. Evaporation of the organic layer gave a residue which was purified by filtration through silica gel to give 70.0 mg of a mixture containing (2'R,3'S)-2',7,10-(tris)-O-triethylsilyl-N-desbenzoyl-N-(t-butoxycarbonyl)-2-desbenzoyl-2-(2-methylbenzoyl)-10-desacetyl taxol and a very small amount of the (2'S,3'R) isomer.

To a solution of 70.0 mg of the mixture obtained from the previous reaction in 4 mL of acetonitrile and 0.19 mL of pyridine at 0° C. was added 0.52 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 49.3 mg of material which was purified by recrystallization to give 44.4 mg (90%) of 2-desbenzoyl-2-(2-methylbenzoyl)-10-deacetyl-N-desbenzoyl-N-(t-butoxycarbonyl) taxol.

m.p. 129–131 9C; [α]$^{25}_{Na}$ −50.8° (c 0.750, CHCl$_3$). $^1$H NMR (CDCl$_3$, 300 MHz) δ 8.05 (m, 1H, benzoate), 7,38 (m, 8H, aromatic), 6.21 (m, 1H, H13), 5.65 (d, J=6.6 Hz, 1H, H2β), 5.46 (m, 1H, NH), 5.24 (m, 1H, H3'), 5.20 (d, J=0.9 Hz, 1H, H10), 4.91 (dd, J=9.3, 1.5 Hz, 1H, H5), 4.60 (br s, 1H, H2'), 4.25 (d, J=8.1 Hz, 1H, H20α), 4.24 (m, 1H, H7), 4.17 (d, J=8.1 Hz, 1H, H20β), 3.88 (d, J=6.6 Hz, 1H, H3), 3.37 (m, 1H, 2'OH), 2.63 (s, 3H, methylbenzoate), 2.57 (m, 1H, H6α), 2.30 (s, 3H, 4Ac), 2.58. (m, 2H, H14), 1.83 (s, 3H, Me18), 1.79 (m, 1H, H6β), 1.75 (s, 3H, Me19), 1.37 (s, 9H, t-butyl), 1.24 (s, 3H, Me17), 1.13 (s, 3H, Me16).

EXAMPLE 10

(73-4)

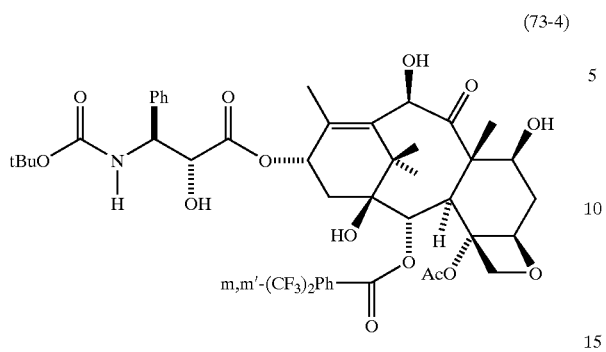

Preparation of N-Desbenzoyl-N-(t-butoxycarbonyl)-2-desbenzoyl-2-(3,5-bis(trifluoromethyl)benzoyl)-10-desacetyl Taxol To a solution of 2-desbenzoyl-2-(3,5-bis(trifluoromethyl) benzoyl)-7,10-(bis)-O-triethylsilyl-10-desacetyl baccatin III (51.3 mg, 0.060 mmol) in 0.5 mL of THF at −45° C. was added dropwise 0.066 mL of a 1.00 M solution of LiN (SiMe$_3$)$_2$ in hexane. After 0.5 h at −45° C., a solution of cis-1-(t-butoxycarbonyl)-3-triethylsilyloxy-4-phenylazetidin-2-one (90 mg, 0.240 mmol) in 0.5 mL of THF was added dropwise to the mixture. The solution was warmed to 0° C. and kept at that temperature for 1 h before 0.5 mL of a 10% solution of ACOH in THF was added. The mixture was partitioned between saturated aqueous NaHCO$_3$ and 60/40 ethyl acetate/hexane. Evaporation of the organic layer gave a residue which was purified by filtration through silica gel to give' 73.9 mg of a mixture containing (2'R,3'S)-2',7,10-(tris)-O-triethylsilyl-N-desbenzoyl-N-(t-butoxycarbonyl)-2-desbenzoyl-2-(3,5-bis(trifluoromethyl) benzoyl)-10-desacetyl taxol and a very small amount of the (2'S,3'R) isomer.

To a solution of 73.9 mg of the mixture obtained from the previous reaction in 4 mL of acetonitrile and 0.19 mL of pyridine at 0° C. was added 0.52 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 53.4 mg of material which was purified by recrystallization to give 49.1 mg (92%) of N-desbenzoyl-N-(t-butoxycarbonyl)-2-desbenzoyl-2-(3,5-bis(trifluoromethyl)-benzoyl)-10-desacetyl taxol.

m.p. 141–143° C.; $[\alpha]^{25}_{Na}$ −43.6° (c 0.730, CHCl$_3$). $^1$H NMR (CDCl$_3$, 300 MHz) δ 8.59 (s, 2H, benzoate, ortho), 8.12 (s, 1H, benzoate para), 7.37 (m, 5H, aromatic), 6.14 (m, 1H, H13), 5.64 (d, J=7.2 Hz, 1H, H2β), 5.36 (m, 1H, NH), 5.21 (d, J=1.2 Hz, 1H, H10), 5.18 (m, 1H, H3'), 4.97 (dd, J=9.6, 2.1 Hz, 1H, H5), 4.58 (m, 1H, H2'), 4.19 (m, 3H, H20, H7), 3.95 (d, J=7.2 Hz, 1H, H3), 3.39 (m, 1H, 2'OH), 2.59 (m, 1H, H6α), 2.30 (s, 3H, 4Ac), 2.25 (m, 2H, H14), 1.85 (s, 3H, Me18), 1.79 (m, 1H, H6β), 1.75 (s, 3H, Me19), 1.32 (s, 9H, t-butyl), 1.22 (s, 3H, Me17), 1.13 (s, 3H, Me16).

EXAMPLE 11

(74-1)

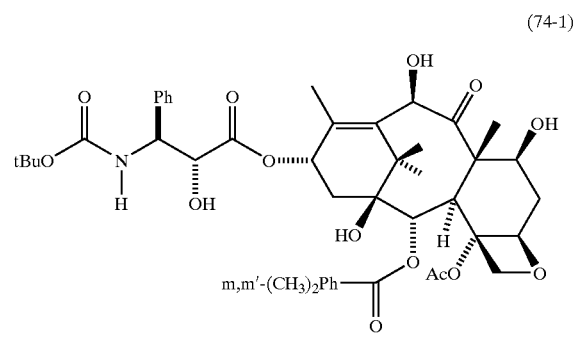

Preparation of N-Desbenzoyl-N-(t-butoxycarbonyl)-2-desbenzoyl-2-(3,5-dimethylbenzoyl)-10-desacetoxy Taxol To a solution of 2-desbenzoyl-2-(3,5-dimethylbenzoyl)-7,10-(bis)-O-triethylsilyl-10-desacetyl baccatin III (48.1 mg, 0.060 mmol) in 0.5 mL of THF at −45° C. was added dropwise 0.066 mL of a 1.00 M solution of LiN(SiMe$_3$)$_2$ in hexane. After 0.5 h at −45° C., a solution of cis-1-(t-butoxycarbonyl)-3-triethylsilyloxy-4-phenylazetidin-2-one (90 mg, 0.240 mmol) 0.5 mL of THF was added dropwise to the mixture. The solution was warmed to 0° C. and kept at that temperature for 1 h before 0.5 mL of a 10% solution of ACOH in THF was added. The mixture was partitioned between saturated aqueous NaHCO$_3$ and 60/40 ethyl acetate/hexane. Evaporation of the organic layer gave a residue which was purified by filtration through silica gel to give 70.1 mg of a mixture containing (2'R,3'S)-2',7,10-(tris)-O-triethylsilyl-N-desbenzoyl-N-(t-butoxycarbonyl)-2-desbenzoyl-2-(3,5-dimethylbenzoyl)-10-desacetoxy taxol and a very small amount of the is (2'S,3'R) isomer.

To a solution of 70.1 mg of the mixture obtained from the previous reaction in 4 mL of acetonitrile and 0.19 mL of pyridine at 0° C. was added 0.52 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 50.2 mg of material which was purified by recrystallization to give 45.1 mg (90%) of N-desbenzoyl-N-(t-butoxycarbonyl)-2-desbenzoyl-2-(3,5-dimethylbenzoyl)-10-desacetoxy taxol.

m.p. 198–200° C.; $[\alpha]^{25}_{Na}$ −49.0° (c 0.965, CHCl$_3$). $^1$H NMR (CDCl$_3$, 300 MHz) δ 7.72 (s, 2H, benzoate, ortho), 7.37 (m, 5H, aromatic), 7.23 (s, 1H, benzoate, para), 6.21 (m, 1H, H13), 5.64 (d, J=7.2 Hz, 1H, H2β), 5.45 (m, 1H, NH), 5.25 (m, 1H, H3'), 5.20 (d, J=1.8 Hz, 1H, H10), 4.94 (dd, J=9.3, 1.2 Hz, 1H, H5), 4.61 (m, 1H, H2'), 4.32 (d, J=8.1 Hz, 1H, H20α), 4.21 (m, 1H, H7), 4.16 (d, J=8.7 Hz, 1H, H20β), 3.89 (d, J=7.2 Hz, 1H, H3), 3.39 (m, 1H, 2'OH), 2.58 (m, 1H, H6α), 2.38 (s, 6H, dimethylbenzoate), 2.36 (s, 3H, 4Ac), 2.27 (m, 2H, H14), 1.88 (m, 1H, H6β), 1.83 (s, 3H, Me18), 1.74 (s, 3H, Me19), 1.33 (s, 9H, t-butyl), 1.22 (s, 3H, Me17), 1.12 (s, 3H, Me16).

EXAMPLE 12

(74-2)

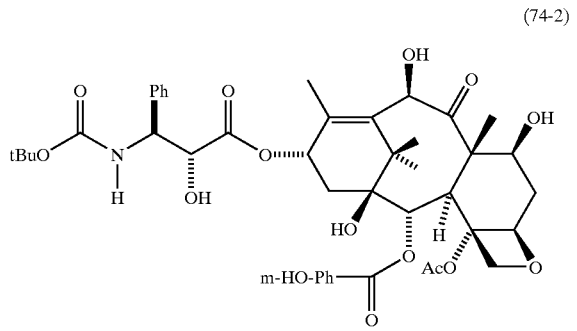

Preparation of N-Desbenzoyl-N-(t-butoxycarbonyl)-2-desbenzoyl-2-(3-hydroxybenzoyl)-10-desacetyl Taxol To a solution of 2-desbenzoyl-2-(3-triethylsilyloxybenzoyl)-7,10-(bis)-O-triethylsilyl-10-desacetyl baccatin III (54.1 mg, 0.060 mmol) in 0.5 mL of THF at −45° C. was added dropwise 0.066 mL of a 1.00 M solution of LiN(SiMe$_3$)$_2$ in hexane. After 0.5 h at −45C., a solution of cis-1-(t-butoxycarbonyl)-3-triethylsilyloxy-4-phenylazetidin-2-one (90 mg, 0.240 mmol) in 0.5 mL of THF was added dropwise to the mixture. The solution was warmed to 0° C. and kept at that temperature for 1 h before 0.5 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 76.7 mg of a mixture containing (2'R,3'S)-2',7,10-tris(triethylsilyl)-N-debenzoyl-N-(t-butoxycarbonyl)-2-desbenzoyl-2-(3-triethylsilyloxybenzoyl)-10-desacetyl taxol and a very small amount of the (2'S,3'R) isomer.

To a solution of 76.7 mg of the mixture obtained from the previous reaction in 4 mL of acetonitrile and 0.19 mL of pyridine at 0° C. was added 0.52 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 49.4 mg of material which was purified by recrystallization to give 43.4 mg (88%) of N-desbenzoyl-N-(t-butoxycarbonyl)-2-desbenzoyl-2-(3-hydroxybenzoyl)-10-desacetyl taxol.

m.p. 153–155° C.; $[\alpha]^{25}_{Na}$ −45.0° (c 0.560, CHCl$_3$). $^1$H NMR (CDCl$_3$, 300 MHz) δ 7.36 (m, 9H, aromatic), 7.10 (m, 1H, OH), 6.38 (m, 1H, H13), 5.60 (d, J=9.9 Hz, NH), 5.53 (d, J=7.5 Hz, 1H, H2β), 5.37 (m, 1H, H3'), 5.18 (d, J=1.2 Hz, 1H, H10), 4.90 (dd, J=9.9, 2.4 Hz, 1H, H5), 4.75 (m, 1H, H2'), 4.29 (d, J=8.4 Hz, 1H, H20α), 4.24 (m, 2H, H7, H20β), 3.93 (d, J=7.5 Hz, 1H, H3), 3.29 (m, 1H, 2'OH), 2.56 (m, 1H, H6α), 2.36 (s, 3H, 4Ac), 2.27 (m, 2H, H14), 1.91 (s, 3H, Me18), 1.85 (m, 1H, H6β), 1.76 (s, 3H, Me19), 1.33 (s, 9H, t-butyl), 1.24 (s, 3H, Me17), 1.08 (s, 3H, Me16).

EXAMPLE 13

Compounds 64-4, 65-1, 65-2, 65-3, 65-4, 66-1, 66-2, 68-1, 68-2, 73-4, 74-1 and 74-2 of Examples 1–12 were evaluated in in vitro cytotoxicity activity against human colon carcinoma cells HCT-116. Cytotoxicity was assessed in HCT116 cells by XTT (2,3-bis(2-methoxy-4-nitro-5-sulfophenyl)-5-[(phenylamino)carbonyl]-2H-tetrazolium hydroxide) assay (Scudiero et al, "Evaluation of a soluble tetrazolium/formazan assay for cell growth and drug sensitivity in culture using human and other tumor cell lines", Cancer Res. 48:4827–4833, 1988). Cells were plated at 4000 cells/well in 96 well microtiter plates and 24 hours later drugs were added and serial diluted. The cells were incubated at 37° C. for 72 hours at which time the tetrazolium dye, XTT, was added. A dehydrogenase enzyme in live cells reduces the XTT to a form that absorbs light at 450 nm which can be quantitated spectrophotometrically. The greater the absorbance the greater the number of live cells. The results are expressed as an IC$_{50}$ which is the drug concentration required to inhibit cell proliferation (i.e. absorbance at 450 nm) to 50% of that of untreated control cells.

All compounds had an IC$_{50}$ less than 0.5 and all except compound 65-4 (Example 5) had an IC$_{50}$ less than 0.1 indicating that they are cytotoxically active.

EXAMPLE 14

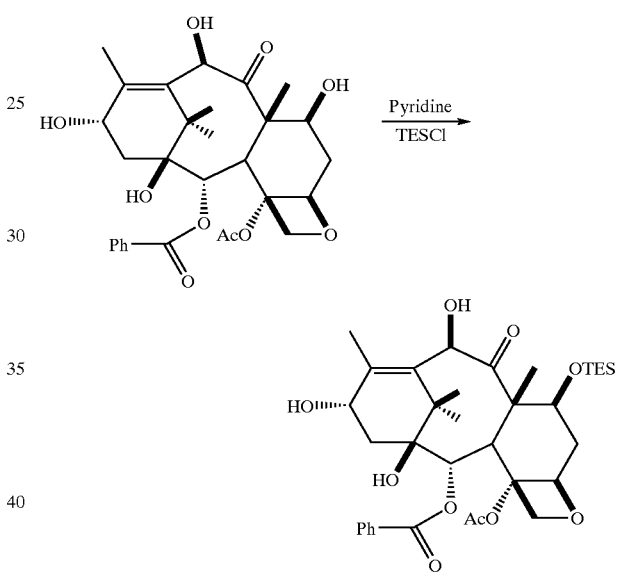

Protection of 10-Deacetyl Baccatin (III) at C7, C10, and C13

7-O-Triethylsilyl-I0-deacetyl baccatin (III). To a solution of 10-deacetyl baccatin (III) (1.5 g, 2.8 mmol) in 100 mL of pyridine was added 4.7 mL (10 eq) of triethylsilyl chloride (TESCl) and the mixture was stirred for 24 h at 25° C. The reaction mixture was diluted with EtOAc (800 mL) and washed with H$_2$O (2×200 mL) and 10% aqueous CuSO$_4$ until all pyridine was removed. The organic layer was washed with brine (50.0 mL), dried over anhydrous Na$_2$SO$_4$, filtered, and concentrated to give crude product (1.92 g). Plug filtration from 20% EtOAc in hexane to 50% EtOAC in hexane gave 7-O-triethylsilyl-10-deacetyl baccatin (III) (1.78 g, 97.7%). m.p. 257–258° C., $[\alpha]^{25}_{Na}$ −23.8° (c 0.5, CHCl$_3$), $^1$H NMR (CDCl$_3$, 300 MHz), δ 8.10 (d, J=7.1 Hz, 2H, benzoate ortho), 7.63–7.45 (m, 3H, aromatic), 5.60 (d, J=7.2 Hz, 1H, H2), 5.17 (d, J=1.7 Hz, 1H, H10), 4.95 (dd, J=1.7, 9.9 Hz, 1H, H5), 4.88 (m, 1H, H13), 4.41 (dd, J=6.6, 10.4 Hz, 1H, H7), 4.31 (d, J=8.2 Hz, 1H, H20α), 4.16 (d, J=8.2 Hz, 1H, H20β), 3.95 (d, J=7.1 Hz, 1H, H3), 2.49 (m, 1H, H6α), 2.28 (s, 3H, 4Ac), 2.10–2.09 (m, 2H, H14α, H14β), 2.08 (s, 3H, Me18), 1.90 (m, 1H, H6β), 1.73 (s, 3H, Me19), 1.19 (s, 3H, Me17), 1.08 (s, 3H, Me16), 1.02–0.93 ((m, 9H, SiCH$_2$CH$_3$), 0.59–0.51 (m, 6H, SiCH$_2$CH$_3$).

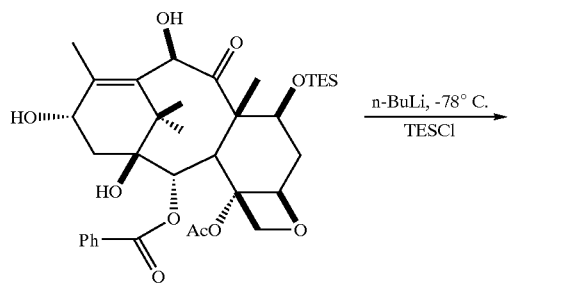

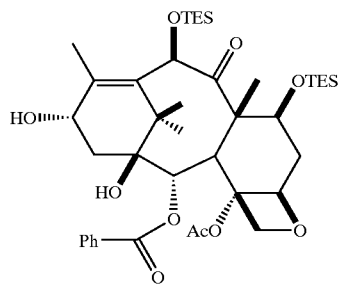

7,10-Bis-O-triethylsilyl-10-deacetyl baccatin (III). To a solution of 7-O-triethylsilyl-10-deacetyl baccatin (III) (1.0 g, 1.55 mmol) in 20 mL of THF at −78° C. under N$_2$ was added 1.04 mL of a 1.64 M solution of n-butyllithium (1.1 equiv) in hexane. The mixture was stirred for 30 min at −78° C. and 0.31 ml (1.2 equiv) of TESCl was added dropwise. The mixture was stirred for 1 h at −78° C. and 10 mL of saturated aqueous NaHCO$_3$ was added. The solution was diluted with EtOAc (80.0 mL). The organic phase was washed with brine (15.0 mL), dried over anhydrous Na$_2$SO$_4$, filtered and concentrated under reduced pressure to give a crude solid (1.45 g). Flash chromatography from 25% EtOAc in hexane to 50% EtOAc in hexane gave 7,10-bis-O-triethylsilyl-10-deacetyl baccatin (III) (0.63 g, 53.6%) and recovered 7-triethylsilyl-10-deacetyl baccatin (III) (0.35 g, 35.0%). m.p. 184–186° C., $[\alpha]^{25}_{Na}$ −46.0° (c 0.5, CHCl$_3$), $^1$H NMR (CDCl$_3$, 300 MHz) δ 8.10 (d, J=6.6 Hz, 2H, benzoate ortho), 7.6–7.4 (m, 3H, aromatic), 5.61 (d, J=7.1 Hz, 1H, H2), 5.21 (s, 1H, H10), 4.93 (dd, J=1.7, 9.3 Hz, 1H, H5), 4.82 (m, 1H, H13), 4.42 (dd, J=6.6, 10.4 Hz, 1H, H7), 4.27 (d, J=8.2 Hz, 1H, H20α), 4.14 (d, J=8.2 Hz, 1H, H20β), 3.91 (d, J=6.6 Hz, 1H, H3), 2.53 (m, 1H, H6α), 2.27 (s, 3H, 4Ac), 2.25 (m, 2H, H14α, H14β), 2.03 (s, 3H, Me18), 1.85 (m, 1H, H6β), 1.64 (s, 3H, Me19), 1.18 (s, 3H, Me17), 1.04 (s, 3H, Me16), 1.02–0.85 (m, 18H, SiCH$_2$CH$_3$), 0.69–0.58 (m, 12H, SiCH$_2$CH$_3$).

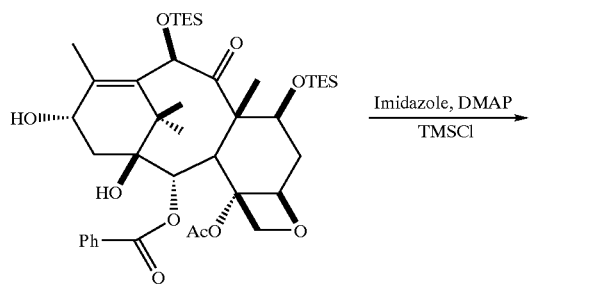

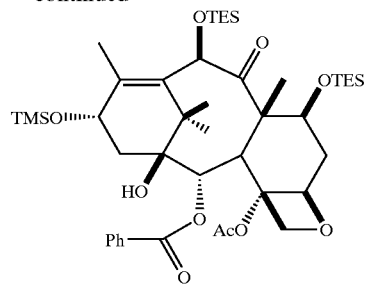

13-O-Trimethylsilyl-7,10-bis-O-triethylsilyl-10-deacetyl baccatin (III). To a solution of 0.5 g (0.66 mmol) of 7,10-bis-O-triethylsilyl-10-deacetyl baccatin (III), 90 mg (2 eq) of imidazole, 40 mg (0.5 eq) of p-dimethylaminopyridine (DMAP) in 15 mL of CH$_2$Cl$_2$ at 0° C. was added 0.17 mL (2 eq) of trimethylsilyl chloride (TMSCl). The solution was stirred at 0° C. for 30 min and 1.0 mL of methanol was added. The mixture was diluted with H$_2$O (10.0 mL and EtOAc (50.0 mL) and the organic layer was separated, washed with brine (10.0 mL), dried over anhydrous Na$_2$SO$_4$, filtered and concentrated under reduced pressure to afford a crude solid (0.58 g). Plug filtration with 10% EtOAc in hexane gave 13-O-trimethylsilyl-7,10-bis-O-triethylsilyl-10-deacetyl baccatin (III) (0.53 g, 96.5%). m.p. 213–215° C., $[\alpha]^{25}_{Na}$ −43.0° (c 0.5, CHCl$_3$), $^1$H NMR (CDCl$_3$, 300 MHz), δ 8.10 (d, J=7.1 Hz, 2H, benzoate ortho), 7.6–7.4 (m, 3H, aromatic), 5.62 (d, J=7.1 Hz, 1H, H2), 5.19 (s, 1H, H10), 4.94 (dd, J=1.8, 8.8 Hz, 1H, H5), 4.86 (m, 1H, H13), 4.41 (dd, J=6.6, 10.4 Hz, 1H, H7), 4.28 (d, J=8.2 Hz, 1H, H20α), 4.12 (d, J=8.2 Hz, 1H, H20β), 3.86 (d, J=7.14 Hz, 1H, H3), 2.51 (m, 1H, H6α), 2.26 (s, 3H, 4Ac), 2.22–2.03 (m, 2, H14α, H14β), 1.93 (s, 3H, Me18), 1.84 (m, 1H, H6β), 1.64 (s, 3H, Me19), 1.19 (s, 3H, Me17), 1.12 (s, 3H, Me16), 1.02–0.93 (m, 18H, SiCH$_2$CH$_3$), 0.69–0.56 (m, 12H, SiCH$_2$CH$_3$), 0.17 (s, 9H, SiCH$_3$).

EXAMPLE 15

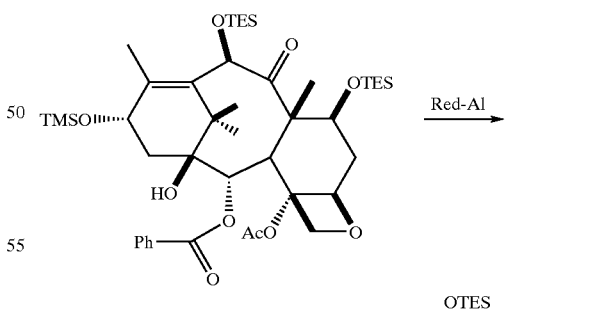

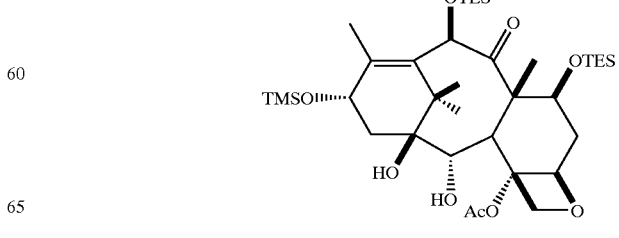

Preparation of Taxol Analogs With Various Substituents At C-2 a. 13-O-Trimethylsilyl-7,10-bis-O-triethylsilyl-2-debenzoyl-2-acetyl-10-deacetyl Baccatin (III).

13-O-Trimethylsilyl-7,10-bis-O-triethylsilyl-2-debenzoyl-10-deacetyl baccatin (III). To a solution of 13-O-trimethylsilyl-7,10-bis-O-triethylsilyl-10-deacetyl baccatin (III) (0.1 g, 0.12 mmol) in THF (6.0 mL) at 0° C. was added dropwise 60 μL of a 1.0 M solution of Red-Al in toluene. The resulting mixture was stirred at 0° C. for 1 h and 3.0 mL of saturated aqueous NaHCO$_3$ was added. The solution was filtered and the solid was rinsed with EtOAc. The filtrate was concentrated under reduced pressure and diluted with EtOAc (50.0 mL). The organic layer was separated and washed with brine (5.0 mL). The combined organic layer was dried over anhydrous Na$_2$SO$_4$, filtered, and concentrated under reduced pressure to give a crude solid (0.14 g). Flash chromatography with 30% EtOAc in hexane gave pure 13-O-trimethylsilyl-7,10-bis-O-triethylsilyl-2-debenzoyl-10-deacetylbaccatin (84.5 mg, 96.6%). m.p. 73–74° C., $[\alpha]^{25}_{Na}$ –24.0° (c 0.5, CHCl$_3$), $^1$H NMR (CDCl$_3$, 300 MHz), δ 5.11 (s, 1H, H10), 4.94 (dd, J=1.7, 9.3 Hz, 1H, H5), 4.87 (m, 1H, H13), 4.62 (d, J=9.3 Hz, 1H, H20α), 4.54 (d, J=8.8 Hz, 1H, H20β), 4.35 (dd, J=6.6, 10.4 Hz, 1H, H7), 3.86 (m, 1H, H2), 3.47 (d, J=6.6 Hz, 1H, H3), 2.51 (m, 1H, H6α), 2.14 (s, 3H, 4Ac), 2.02–1.83 (m, 3H, H14α, H14β, H6β), 1.60 (s, 3H, Me18), 1.60 (s, 3H, Me19), 1.14 (s, 3H, Me17), 1.07 (s, 3H, Me16), 0.99–0.92 (m, 18H, SiCH$_2$C$\underline{H}_3$), 0.66–0.55 (m, 12H, SiC$\underline{H}_2$CH$_3$), 0.13 (s, 9H, SiC$\underline{H}_3$).

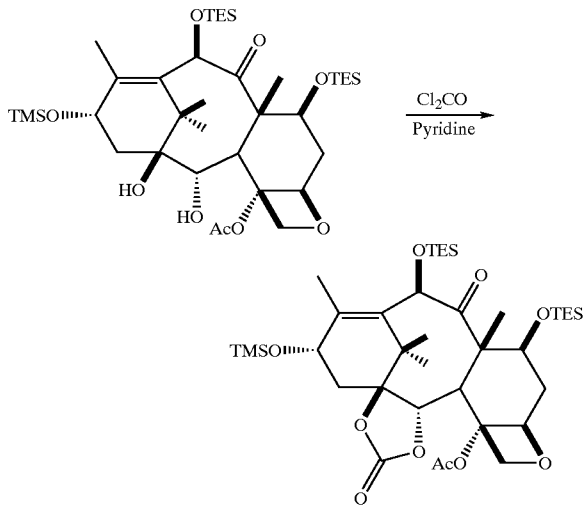

13-O-Trimethylsilyl-7,10-bis-O-triethylsilyl-2-debenzoyl-10-deacetyl baccatin (III) 1,2-carbonate. To a solution of 13-O-trimethylsilyl-7,10-bis-O-triethylsilyl-2-debenzoyl-10-deacetyl baccatin (III) (20.0 mg, 0.027 mmol) in CH$_2$Cl$_2$ (4.0 mL) and pyridine (0.8 mL) at –78° C. was added 80 μL of a 3.4 M solution of COCl$_2$ in benzene (10 eq). The mixture was warmed to –10° C. (ice-acetone) and kept for 30 min at –10° C. Saturated aqueous NaHCO$_3$ (5.0 mL) was added and the mixture were extracted with EtOAc (3×10 mL). The organic layer was washed with aqueous 10% CuSO$_4$ until all pyridine disappeared then brine (5.0 mL). The combined organic layer was dried over anhydrous Na$_2$SO$_4$, filtered and concentrated under reduced pressure to give a crude solid (22.5 mg). Plug filtration with 20% EtOAc in hexane gave pure 13-O-trimethylsilyl-7,10-bis-O-triethylsilyl-2-debenzoyl-10-deacetyl baccatin (III) 1,2-carbonate (20.5 mg, 99.0%). m.p. 144–146° C., $[\alpha]^{25}_{Na}$ –27.5° (c 0.5, CHCl$_3$), $^1$H NMR (CDCl$_3$, 300 MHz), δ 5.15 (s, 1H, H10), 4.90 (m, 2H, H5, H13), 4.58 (d, J=8.9 Hz, 1H, H20α), 4.44 (d, J=8.6 Hz, 1H, H20β), 4.43 (d, J=5.4 Hz, 1H, H2), 4.37 (dd, J=6.6, 10.4 Hz, 1H, H7), 3.43 (d, J=5.6 Hz, 1H, H3), 256 (m, 1H, H6α), 2.37 (m, 1H, 14α), 2.14 (s, 3H, 4Ac), 2.13 (m, 1H, H14β), 1.92 (s, 3H, Me18), 1.84 (m, 1H, H6β), 1.64 (s, 3H, Me19), 1.22 (s, 3H, Me17), 1.17 (s, 3H, Me16), 0.99–0.85 (m, 18H, SiCH$_2$C$\underline{H}_3$), 0.66–0.55 (m, 12H, SiC$\underline{H}_2$CH$_3$), 0.17 (s, 9H, SiC$\underline{H}_3$).

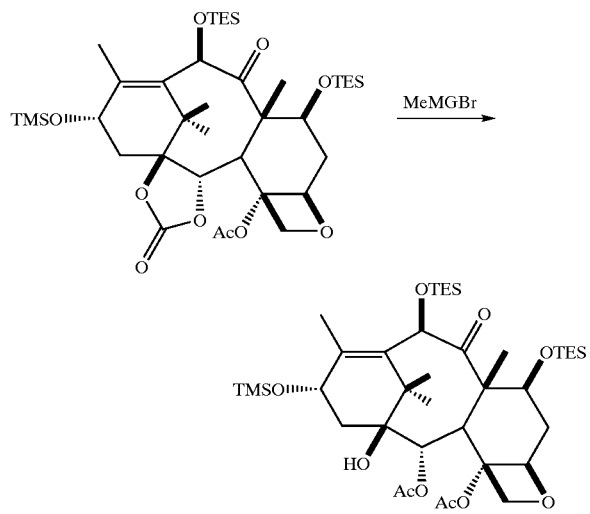

13-O-Trimethylsilyl-7,10-bis-O-triethylsilyl-2-debenzoyl-2-acetyl-10-deacetyl baccatin (III). To a solution of 13-O-trimethylsilyl-7,10-bis-O-triethylsilyl-2-debenzoyl-10-deacetyl baccatin (III) 1,2-carbonate (10.0 mg, 0.014 mmol) in THF (0.5 mL) at 0° C. was added 40 μL of a 3.4 M solution (10 eq) of MeMgBr in ether. The solution was stirred for 1 h at 0° C. under N$_2$ and saturated aqueous NaHCO$_3$ was added (1.0 mL). The mixture was extracted with EtOAc (3×5.0 mL) and the organic layer was washed with brine (5.0 mL), dried over anhydrous Na$_2$SO$_4$, filtered and concentrated under reduced pressure to give a crude solid (11.3 mg). Flash chromatography with 20% EtOAc in hexane gave pure 13-O-trimethylsilyl-7,10-bis-O-triethylsilyl-2-debenzoyl-2-acetyl-10-deacetyl baccatin (III) (9.8 mg, 95.9%). m.p. 201–203° C., $[\alpha]^{25}_{Na}$ –38.9° (c 0.5, CHCl$_3$), $^1$H NMR (CDCl$_3$, 300 MHz), δ 5.34 (d, J=7.2 Hz, 1H, H2), 5.15 (s, 1H, H10), 4.93 (dd, J=2.8, 9.3 H, 1H, H5), 4.83 (m, 1H, H13), 4.43 (d, J=7.7 Hz, 1H, H20α), 4.38 (d, J=7.1 Hz, 1H, H20β), 4.18 (dd, J=6.1, 11.6 Hz, 1H, H7), 3.73 (d, J=6.6 Hz, 1H, H3), 2.54 (m, 1H, H6α, 2.20–2.03 (m, 2H, H14α, H14β), 2.15 (s, 3H, 4Ac), 2.07 (s, 3H 2Ac), 1.96 (m, 1H, H6β), 1.89 (s, 3H, Me18), 1.58 (s, 3H, Me19), 1.12 (s, 3H, Me17), 1.00 (s, 3H, Me16), 0.99–0.91 (m, 18H, SiCH$_2$C$\underline{H}_3$), 0.67–0.56 (m, 12H, SiC$\underline{H}_2$CH$_3$), 0.16 (s, 9H, SiC$\underline{H}_3$).

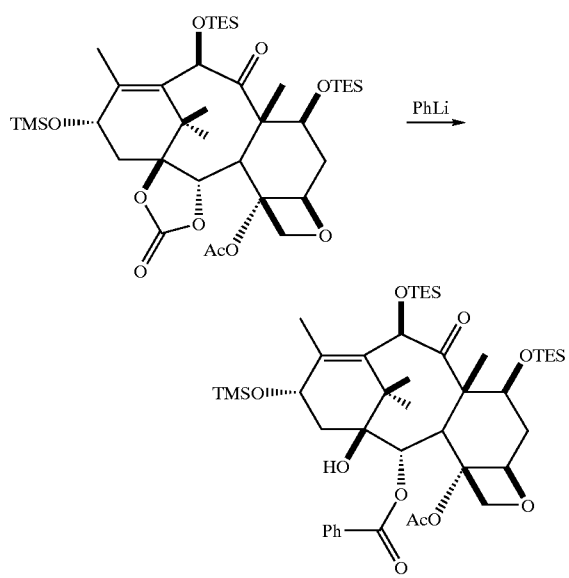

b. 13-O-Trimethysilyl-7,10-bis-O-triethylsilyl-2-debenzoyl-10-deacetyl Baccatin (III)

To a solution of 13-O-trimethylsilyl-7,10-bis-O-triethylsilyl-2-debenzoyl-10-deacetyl baccatin (III) 1,2 carbonate (10.0 mg, 0.014 mmol) in THF (0.5 mL) at −45° C. was added 78 μL of a 1.8 M solution of phenyllithium (10 eq) in 30% ether/70% cyclohexane. The solution was stirred for 1 h at −45° C. under $N_2$ and saturated aqueous NaHCO was added (1.0 mL). The mixture was extracted with EtOAc (3×5.0 mL). The organic layer was washed with brine (5.0 mL), dried over anhydrous $Na_2SO_4$, filtered and concentrated under reduced pressure to give a crude solid (12.5 mg). Flash chromatography with 10% EtOAc in hexane gave pure 13-O-trimethylsilyl-7,10-bis-O-triethylsilyl-2-debenzoyl-10-deacetyl baccatin (III) (10.8 mg, 94.5%).

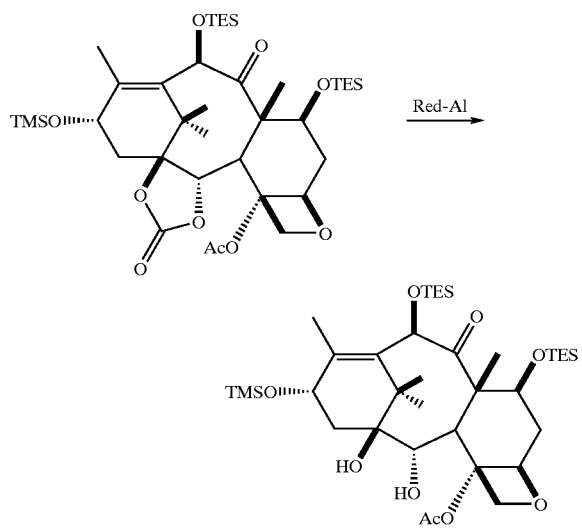

c. 13-O-Trimethylsilyl-7,10-bis-O-triethylsilyl-2-debenzoyl-10-deacetyl Baccatin (III)

To a stirred solution of 13-O-trimethylsilyl-7,10-bis-O-triethylsilyl-2-debenzoyl-10-deacetyl baccatin (III) 1,2-carbonate (6.0 mg, 0.0082 mmol) in THF (0.5 mL) at 0° C. was added 60 μL of a 0.068 M solution (5 eq) of Red-Al in toluene. The resulting solution was stirred for 1 h at 0° C. under $N_2$, 1.0 mL of saturated aqueous $NaHCO_3$ was added, and the mixture was extracted with EtOAc (2×10.0 ml). The organic layer was washed with brine (5.0 mL), dried over anhydrous $Na_2SO_4$, filtered and concentrated under reduced pressure to give a crude solid (6.75 mg). Flash chromatography with 30% EtOAc in hexane gave 13-O-trimethylsilyl-7,10-bis-O-triethylsilyl-2-debenzoyl-10-deacetyl baccatin (III) (4.3 mg, 71.5%) and 13-O-trimethylsilyl-7,10-bis-O-triethylsilyl-2-debenzoyl-2-formyl-10-deacetyl baccatin (III) (1.5 mg, 24.5%).

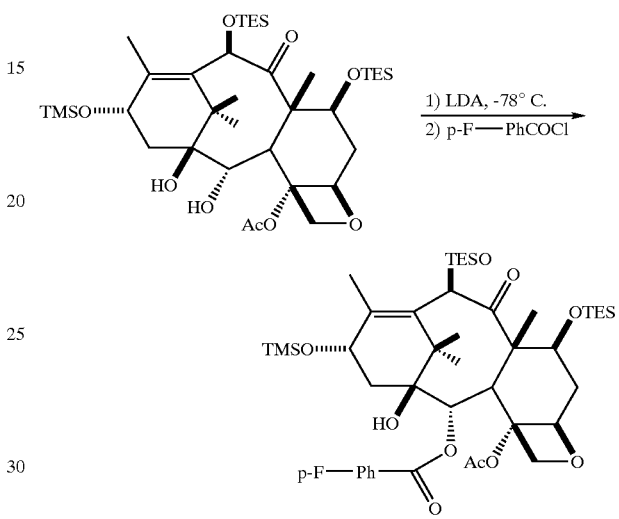

d. 13-O-Trimethylsilyl-7,10-bis-O-triethylsilyl-2-debenzoyl-2-p-fluorobenzoyl-10-deacetyl Baccatin (III)

To a solution of 13-O-trimethylsilyl-7,10-bis-O-triethylsilyl-2-debenzoyl-10-deacetyl baccatin (III) (40.0 mg, 0.054 mmol) in THF (1.0 mL) at −78° C. under $N_2$ was added dropwise 320 μL of a 0.328 M solution (2 eq) of LDA in THF. The mixture was stirred for 30 min at −78° C. and a solution of 26 μL (4 eq) of p-fluorobenzoyl chloride in 100 μL of THF was added. After 1 h diisopropylamine (100 μL) was added and the mixture was warmed to 25° C. After 10 min the mixture was diluted with aqueous $NaHCO_3$ (5.0 mL) and extracted with EtOAc (2×10.0 mL). The organic layer was washed with brine (5.0 mL), dried over anhydrous $Na_2SO_4$, filtered and concentrated under reduced pressure to give a crude solid (67.5 mg). Flash chromatography with 10% EtOAc in hexane gave 13-O-trimethylsilyl-7,10-bis-O-triethylsilyl-2-debenzoyl-2-p-fluorobenzoyl-10-deacetyl baccatin (III) (36.9 mg, 80.2%). m.p. 216–218° C., $[\alpha]^{25}_{Na}$ −45.6° (c 0.5, $CHCl_3$), $^1H$ NMR ($CDCl_3$, 300 MHz) δ 8.10 (m, 2H, aromatic), 7.18–7.12 (m, 2H, aromatic), 5.60 (d, J=7.2 Hz, 1H, H2), 5.19 (s, 1H, H10), 4.94 (dd, J=1.7, 9.9 Hz, 1H, H5), 4.86 (m, 1H, H13), 4.41 (dd, J=6.9, 10.4 Hz, 1H, H7), 4.26 (d, J=8.2 Hz, 1H, H20α), 4.11 (d, J=82 Hz, 1H, H20β), 3.86 (d, J=6.6 Hz, 1H, H3), 2.51 (m, 1H, H6α), 2.25 (s, 3H, 4Ac), 2.11 (m, 2H, H14α, H14β), 2.04 (s, 3H, Me18), 1.88 (m, 1H, H6β), 1.64 (s, 3H, Me19), 1.18 (s, 3H, Me17), 1.12 (s, 3H, Me16), 1.02–0.92 (m, 18H, $SiCH_2C\underline{H}_3$), 0.69–0.54 (m, 12H, $SiC\underline{H}_2CH_3$), 0.17 (s, 9H, $SiC\underline{H}_3$).

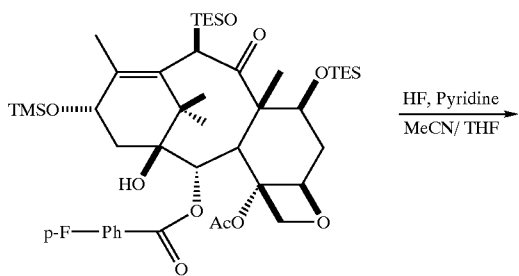

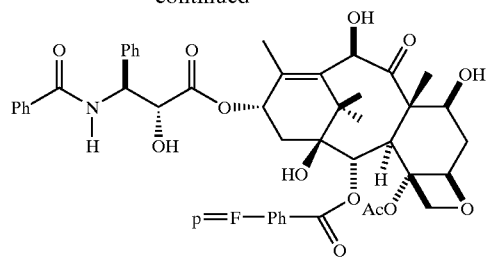

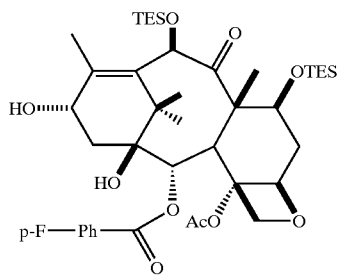

e. 7,10-Bis-O-triethylsilyl-2-debenzoyl-2-p-fluorobenzoyl-10-deacetyl Baccatin (III)

To a solution of 13-O-trimethylsilyl-7,10-bis-O-triethylsilyl-2-debenzoyl-2-p-fluorobenzoyl-10-deacetyl baccatin (III) (30.0 mg, 0.035 mmol) in 2.25 mL of acetonitrile and 2.25 mL of THF in a polyethylene vial was added dropwise 48 μL of pyridine and 75 μL of 48% aqueous HF. The reaction mixture was stirred at 25° C. for 12 h and then diluted with EtOAc (20.0 mL). Saturated aqueous NaHCO$_3$ was added until gas evolution ceased. The organic layer was separated, washed with brine (3.0 mL), dried over anhydrous Na$_2$SO$_4$, filtered and concentrated under reduced pressure to give a crude solid (36.2 mg). Flash chromatography with 25% EtOAc in hexane gave 7,10-bis-O-triethylsilyl-2-debenzoyl-2-p-fluorobenzoyl-10-deacetyl baccatin (III) (21.5 mg, 78.8%) and 10-O-triethylsilyl-2-debenzoyl-2-p-fluorobenzoyl-10-deacetyl baccatin (III) (3.8 mg, 15.9%). m.p. 186–188° C., $[\alpha]^{25}_{Na}$ −48.2° (c 0.5, CHCl$_3$), $^1$H NMR (CDCl$_3$, 300 MHz) δ 8.11 (m, 2H, aromatic), 7.26–7.11 (m, 2H, aromatic), 5.59 (d, J=6.6 Hz, 1H, H2), 5.21 (s, 1H, H10), 4.94 (dd, J=1.7, 9.34 Hz, 1H, H5), 4.84 (m, 1H, H13), 4.42 (dd, J=6.6, 10.4 Hz, 1H, H7), 4.26 (d, J=8.24 Hz, 1H, H20α), 4.14 (d, J=8.25 Hz, 1H, H20β), 3.90 (d, J=6.6 Hz, 1H, H3), 2.54 (m, 1H, H6α), 2.26 (s, 3H, 4Ac), 2.05 (m, 2H, H14α, H14β), 2.02 (s, 3H, Me18), 1.88 (m, 1H, H6β), 1.65 (s, 3H, Me19), 1.18 (s, 3H, Me17), 1.05 (s, 3H, Me16), 1.02–0.92 (m, 18H, SiCH$_2$CH$_3$), 0.69–0.53 (m, 12H, SiCH$_2$CH$_3$).

f. 2-Debenzoyl-2-p-fluorobenzoyl Taxol.

To a solution of 7,10-bis-O-triethylsilyl-2-debenzoyl-2-p-fluoro-benzoyl-10-deacetyl baccatin (III) (20.0 mg, 0.026 mmol) in 1.0 mL of THF at −45° C. was added dropwise 16 μL of a 1.64 M solution of n-butyllithium in hexane. After 0.5 h at ° 45° C., a solution of (±) cis-1-benzoyl-3-triethylsilyloxy-4-phenyl azetidin-2-one (50.0 mg, 0.13 mmol) in THF (0.5 mL) was added dropwise to the mixture. The solution was warmed to 0° C. and kept at that temperature for 1 h and 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel with 20% EtOAc in hexane to give a crude solid (32.5 mg). To a solution of this solid in 1.6 mL of acetonitrile and 79 μL of pyridine at 0° C. was added 240 μL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave a crude solid (24.4 mg) which was purified by flash chromatography with 70% EtOAc in hexane to give 2-debenzoyl-2-p-fluorobenzoyl taxol (15.2 mg, 70.4%). m.p. 180–183° C., $[\alpha]^{25}_{Na}$ −56.9° (c 0.5, CHCl$_3$), $^1$H NMR (CDCl$_3$, 300 MHz) δ 8.15 (m, 2H, aromatic), 7.73 (m, 2H, aromatic), 7.52–7.34 (m, 8H, aromatic), 7.20 (m, 2H, aromatic), 7.07 (d, J=9.3 Hz, 1H, NH), 6.22 (dd, J=8.8, 8.8 Hz, 1H, H13), 5.79 (dd, J=8.8, 2.7 Hz, 1H, H3'), 5.64 (d, J=7.1 Hz, 1H, H2β), 5.17 (s, 1H, H10), 4.94 (dd. J=9.3, 1.7 Hz, 1H, H5), 4.79 (m, 1H, H2'), 4.29–4.15 (m, 3H, H7, H20α, H20O), 3.90 (d, J=7.1 Hz, 1H H3), 3.56 (d, J=5.0 Hz, 1H, 2'OH), 2.58 (m, 1H, H6α), 2.38 (s, 3H, 4Ac), 2.28 (m, 2H, H14α, H14β). 1.82 (m, 1H, H6), 1.79 (s, 3H, Me18), 1.74 (s, 3H, Me19), 1.20 (s, 3H, Me17), 1.10 s, 3H, Me16).

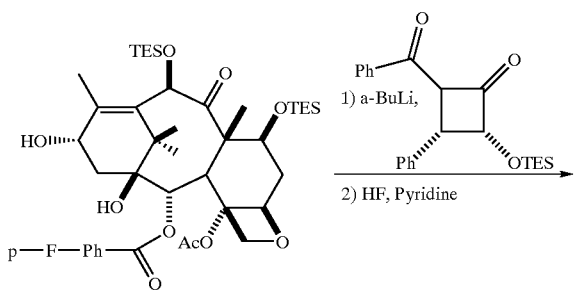

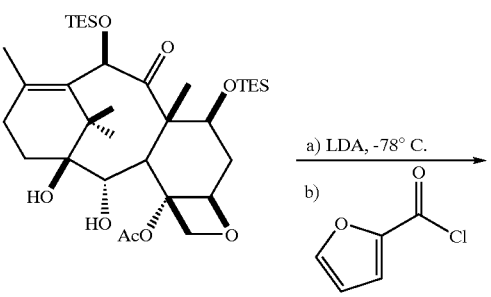

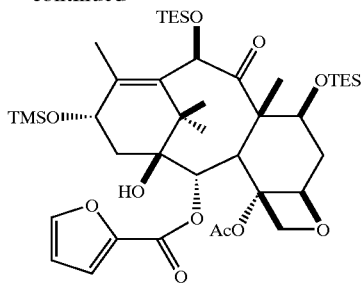

g. 13-O-Trimethylsilyl-7,10-bis-O-triethylsilyl-2-debenzoyl-2-(2-furoyl)-10-deacetyl Baccatin (III)

To a solution of 13-O-trimethylsilyl-7,10-bis-O-triethylsilyl-2-debenzoyl-10-deacetyl baccatin (III) (40.0 mg, 0.054 mmol) in THF (1.0 mL) at −78° C. under N$_2$ was added dropwise 320 μL of a 0.328 M solution (2 eq) of LDA in THF. The mixture was stirred for 30 min at −78° C. and a solution of 26 μL (4 eq) of p-fluorobenzoyl chloride in 100 μL of THF was added. After 1 h diisopropylamine (100 μL) was added and the mixture was warmed to 25° C. After 10 min the mixture was diluted with aqueous NaHCO$_3$ (5.0 mL) and extracted with EtOAc (2×10.0 mL). The organic layer was washed with brine (5.0 mL), dried over anhydrous Na$_2$SO$_4$, filtered and concentrated under reduced pressure to give a crude solid (64.2 mg). Flash chromatography with 15% EtOAc in hexane gave 13-O-trimethylsilyl-7,10-bis-O-triethylsilyl-2-debenzoyl-2-(2-furoyl)-10-deacetyl baccatin (III) (33.9 mg, 76.3%). m.p. 208–210° C., $[\alpha]^{25}_{Na}$ −49.6° (c 0.5, CHCl$_3$), $^1$H NMR (CDCl$_3$, 300 MHz) δ 7.62 (m, 1H, furoyl), 7.20 (m, 1H, furoyl), 6.50 (m, 1H, furoyl), 5.52 (d, J=7.1 Hz, 1H, H2), 5.18 (s, 1H, H10), 4.95 (dd, J=1.6, 9.4 Hz, 1H, H5), 4.85 (m, 1H, H13), 4.41 (dd, J=6.9, 10.4 Hz, 1H, H7), 4.38 (d, J=8.8 Hz, 1H, H20α), 4.15 (d, J=8.2 Hz, 1H, H20β), 3.82 (d, J=6.6 Hz, 1H, H3), 2.51 (m, 1H, H6α), 2.22 (s, 3H, 4Ac), 2.10 (m, 2H, H14α, H14β), 1.92 (s, 3H, Me18), 1.89 (m, 1H, H6β), 1.64 (s, 3H, Me19), 1.17 (s, 3H, Me17), 1.12 (s, 3H, Me16), 1.01–0.93 (m, 18H, SiCH$_2$C$\underline{H}_3$), 0.69–0.52 (m, 12H, SiC$\underline{H}_2$CH$_3$), 0.16 (s, 9H, SiC$\underline{H}_3$).

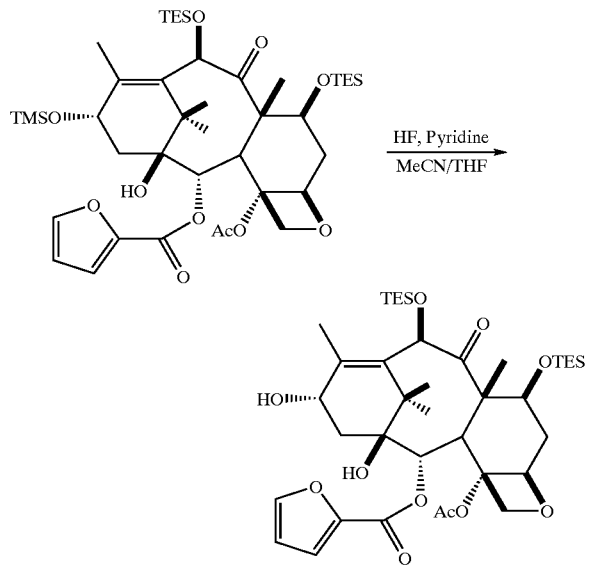

h. 7,10-bis-O-Triethylsilyl-2-debenzoyl-2-(2-furoyl)-10-deacetyl Baccatin (III)

To a solution of 13-O-trimethylsilyl-7,10-bis-O-triethylsilyl-2-debenzoyl-2-(2-furoyl)-10-deacetyl baccatin (III) (30.0 mg, 0.036 mmol) in 2.25 mL of acetonitrile and 2.25 mL of THF in a polyethylene vial was added dropwise 48 μL of pyridine and 75 μL of 48% aqueous HF. The reaction mixture was seed at 25° C. for 12 h and then diluted with EtOAc (20.0 mL). Saturated aqueous NaHCO$_3$ was added until gas evolution ceased. The organic layer was separated, washed with brine (3.0 mL), dried over anhydrous Na$_2$SO$_4$, filtered and concentrated under reduced pressure to give a crude solid (33.4 mg). Flash chromatography with 30% EtOAc in hexane gave 7,10-bis-O-triethylsilyl-2-debenzoyl-2-(2-furoyl)-10-deacetyl baccatin (III) (21.3 mg, 78.8%) and 10-O-triethylsilyl-2-debenzoyl-2-(2-furoyl)-10-deacetyl baccatin (III) (4.9 mg, 21.4%). m.p. 179–181° C., $[\alpha]^{25}_{Na}$ −45.6° (c 0.5, CHCl$_3$), $^1$H NMR (CDCl$_3$, 300 MHz) δ 7.62 (m, 1H, furoyl), 7.21 (m, 1H, furoyl), 6.53 (m, 1H, furoyl), 5.51 (d, J=7.1 Hz, 1H, H2), 5.20 (s, 1H, H10), 4.94 (dd, J=1.7, 9.3 Hz, 1H, H5), 4.82 (m, 1H, H13), 4.43–4.37 (m, 2H, H7, H20α), 4.18 (d, J=8.2 Hz, 1H, H20β), 3.87 (d, J=7.2 Hz, 1H, H3), 2.52 (m, 1H, H6α), 2.23 (s, 3H, 4Ac), 2.10 (m, 2H, H14α, H14β), 2.01 (s, 3H, Me18), 1.88 (m, 1H, H6β), 1.64 (s, 3H, Me19), 1.17 (s, 3H, Me17), 1.04 (s, 3H, Me16), 1.02–0.92 (m, 18H, SiCH$_2$C$\underline{H}_3$), 0.69–0.54 (m, 12H, SiC$\underline{H}_2$CH$_3$).

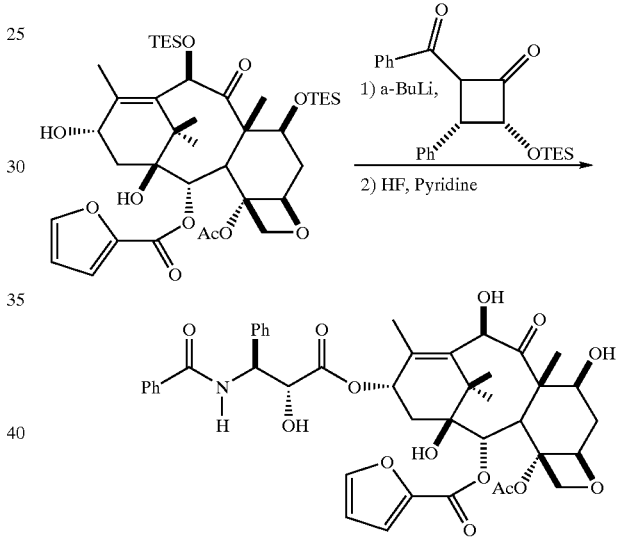

i. 2-Debenzoyl-2-(2-furoyl) Taxol.

To a solution of 7,10-bis-O-triethylsilyl-2-debenzoyl-2-(2-furoyl)-10-deacetyl baccatin (III) (20 mg, 0.027 mmol) in 1.0 mL of THF at −45° C. was added dropwise 16 μL of a 1.64 M solution of n-butyllithium in hexane. After 0.5 h at −45° C., a solution of (±) cis-1-benzoyl-3-triethylsilyloxy-4-phenyl azetidin-2-one (50.0 mg, 0.13 mmol) in THF (0.5 mL) was added dropwise to the mixture. The solution was warmed to 0° C. and kept at that temperature for 1 h and 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel with 20% EtOAc in hexane to give a crude solid (31.7 mg). To a solution of this solid in 1.6 mL of acetonitrile and 79 μL of pyridine at 0° C. was added 240 μL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave a crude solid (24.4 mg) which was purified by flash chromatography with 70% EtOAc in hexane to give 2-debenzoyl-2-(2-furoyl) taxol (14.9 mg, 68.8%). m.p. 176–179° C., $[\alpha]^{25}_{Na}$ –43.1° (c 0.5, CHCl$_3$), $^1$H NMR (CDCl$_3$, 300 MHz) δ 7.76–7.32 (m, 12H, aromatic) 7.08 (d, J=8.8 Hz, 1H, NH), 6.60 (m, 1H, furoyl), 6.20 (dd, J=8.8, 8.8 Hz, 1H, H13), 5.78 (dd, J=8.8, 2.8 Hz, 1H, H3'), 5.56 (d, J=7.1 Hz, 1H, H2β), 5.16 (s, 1H H10), 4.93 (dd, J=9.3, 1.7 Hz, 1H, H5), 4.78 (m, 1H, H2'), 4.40 (d, J=8.3 Hz, 1H, H20α), 4.24 (d, J=8.2 Hz, 1H, 20β), 4.19 (m, 1H, H7), 3.86 (d, J=7.1 Hz, 1H, H3), 3.57 (d, J=5.0 Hz, 1H, 2'OH), 2.56 (m, 1H, H6α), 2.35 (s, 3H, 4Ac), 2.24 (m, 2H, H14α, H14β), 1.83 (m, 1H, H6β), 1.76 (s, 3H, Me18), 1.73 (s, 3H, Me19), 1.19 (s, 3H, Me17), 1.08 (s, 3H, Me16).

EXAMPLE 16

Preparation of Taxol Analogs With Various Substituents At C-4

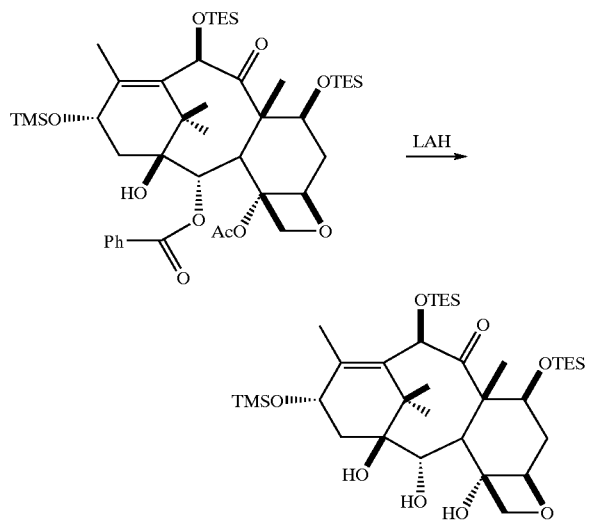

a. 13-O-Trimethylsilyl-7,10-bis-O-triethylsilyl-2-debenzoyl-4,10-bisdeacetyl baccatin (III).

To a solution of 13-O-trimethylsilyl-7,10-bis-O-triethylsilyl-10-deacetyl baccatin (III) (0.1 g, 0.012 mmol) in ether (4.0 mL) at –10° C. was added dropwise 320 μL of a 1.0 M solution of lithium aluminum hydride (LAH) in ether. The resulting mixture was slowly warmed from –10° C. to 0° C. over a 2 h period and 3.0 mL of saturated aqueous NaHCO$_3$ was added. The solution was filtered and the solid was rinsed with EtOAc. The filtrate was concentrated under reduced pressure and diluted with EtOAc (50.0 mL). The organic layer was separated and washed with brine (5.0 mL). The combed organic layer was dried over anhydrous Na$_2$SO$_4$, filtered, and concentrated under reduced pressure to give a crude oil (0.15 g). Flash chromatography with 30% EtOAc in hexane gave pure 13-O-trimethylsilyl-7,10-bis-O-triethylsilyl-2-debenzoyl-4,10-bisdeacetyl baccatin (III) (72.0 mg, 85.8%) as a colorless oil. $[\alpha]^{25}_{Na}$ –25.5° (c 0.5, CHCl$_3$), $^1$H NMR (CDCl$_3$, 300 MHz), δ 5.15 (s, 1H, H10), 4.73 (dd, J=1.8, 8.9 Hz, 1H, H5), 4.65 (m, 1H, H13), 4.53 (d, J=9.3 Hz, 1H, H20α), 4.39 (d, J=8.2 Hz, 1H, H20β), 4.00 (dd, J=6.0, 11.5 Hz, 1H, H7), 3.76 (m, 1H, 2H), 3.44 (d, J=11.0 Hz, 2OH), 3.27 (d, J=6.0 Hz, 1H, H3), 2.45 (m, 2H, H6α, H14α), 2.08–1.93 (m, 2H, H6β, H14β), 1.84 (s, 3H, Me18), 1.53 (s, 3H, Me19), 1.09 (s, 3H, Me17), 1.05 (s, 3H, Me16), 1.01–0.91 (m, 18H, SiCH$_2$CH$_3$), 0.66–0.53 (m, 12H, SiCH$_2$CH$_3$), 0.23 (s, 9H, SiCH$_3$).

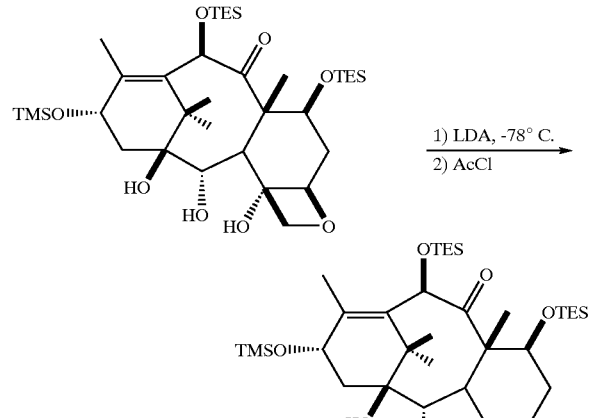

b. 13-O-Trimethylsilyl-7,10-bis-O-triethylsilyl-2-debenzoyl-10-deacetyl Baccatin (III)

To a solution of 13-O-trimethylsilyl-7,10-bis-O-triethylsilyl-2-debenzoyl-4,10-bisdeacetyl baccatin (III) (10.0 mg, 0.0143 mmol) in THF (1.0 mL) at –78° C. was added 440 μL of a 0.328 M solution (10 eq) of lithium diisopropyl amide (LDA) in THF under N$_2$. The solution was stirred for 30 min at –78° C. and 200 μL of a 1.4 M solution of acetyl cholide in THF (20 eq) was added. The mixture were stirred for 1 h at –78° C., saturated aqueous NaHCO$_3$ (2.0 mL) was added, and the mixture was extracted with EtOAc (2×10 mL). The organic layer was washed with brine (5.0 mL), dried over anhydrous Na$_2$SO$_4$, filtered and concentrated to give a crude oil (12.7 mg). Flash chromatography from 25% EtOAc to 50% EtOAc in hexane gave 13-O-trimethylsilyl-7,10-bistriethylsilyl-2-debenzoyl-10-deacetylbaccatin (6.1 mg, 57.6%), 13-O-trimethylsilyl-7,10-bis-O-tri-ethylsilyl-2-debenzoyl-2-acetyl-4,10-bisdeacetyl baccatin (III) (1.89 mg, 17.9%), recovered 13-O-trimethylsilyl-7,10-bis-O-triethylsilyl-2-debenzoyl-4,10-bisdeacetyl baccatin (III) (1.2 mg, 12.0%) and 13-O-trimethylsilyl-7,10-bis-O-triethylsilyl-2-debenzoyl-2-acetyl-4,10-bisdeacetyl baccatin (III) (<1.0 mg).

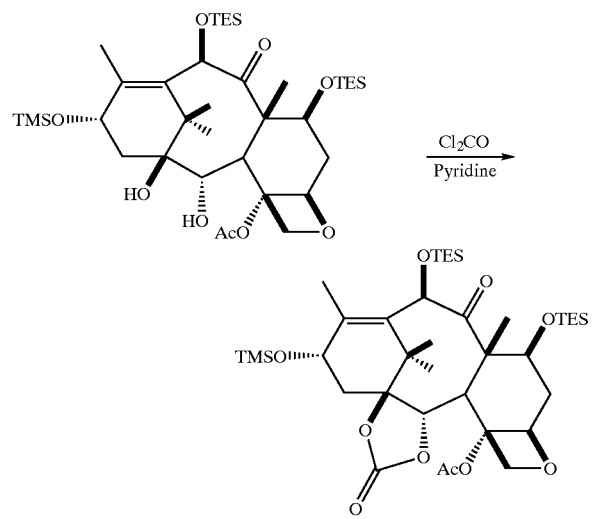

c. 13-O-Trimethysilyl-7,10-bis-O-triethylsilyl-2-debenzoyl-4,10-bisdeacetyl Baccatin (III) 1,2-Carbonate To a solution of 13-O-trimethylsilyl-7,10-bis-O-triethylsilyl-2-debenzoyl-4,10-bisdeacetyl baccatin (III)

(20.0 mg, 0.029 mmol) in CH₂Cl₂ (4.0 mL) and pyridine (0.8 mL) at −78° C. was added 80 μL of a 3.4 M solution of COCl₂ in benzene (10 eq). The mixture was warned to −10° C. (ice-acetone) and kept for 30 min at −10° C. Saturated aqueous NaHCO₃ (5.0 mL) was added and the mixture were extracted with EtOAc (3×10 mL). The organic layer was washed with aqueous 10% CuSO₄ then brine (5.0 mL), dried over anhydrous Na₂SO₄, filtered and concentrated under reduced pressure to give a crude solid (21.9 mg). Plug filtration with 20% EtOAc in hexane gave pure 13-O-trimethylsilyl-7,10-bis-O-triethylsilyl-2-debenzoyl-4,10-bisdeacetyl baccatin (III) 1,2-carbonate (20.8 mg, 98.9%). m.p. 147–148° C., [α]²⁵_Na −28.8° (c 0.5, CHCl₃), ¹H NMR (CDCl₃, 300 MHz), δ 5.21 (s, 1H, H10), 4.76 (dd, J=2.8, 9.9 Hz, 1H, H5), 4.65 (m, 1H, H13), 4.54 (d, J=8.8 Hz, 1H, H20α), 4.52 (d, J=8.3 Hz, 1H, H20β), 4.32 (d, J=5.0 Hz, 1H, H2), 4.10 (dd, J=6.6, 11.0 Hz, 1H, H7), 3.10 (d, J=5.3 Hz, 1H, H3), 2.54 (m, 3H, H6α, H14α, H14β, 1.99 (m, 1H, H6β), 1.92 (s, 3H, Me18), 1.61 (s, 3H, Me19), 1.17 (s, 3H, Me17), 1.12 (s, 3H, Me16), 1.01–0.91 (m, 18H, SiCH₂CH₃), 0.67–0.56 (m, 12H, SiCH₂CH₃), 0.23 (s, 9H, SiCH₃).

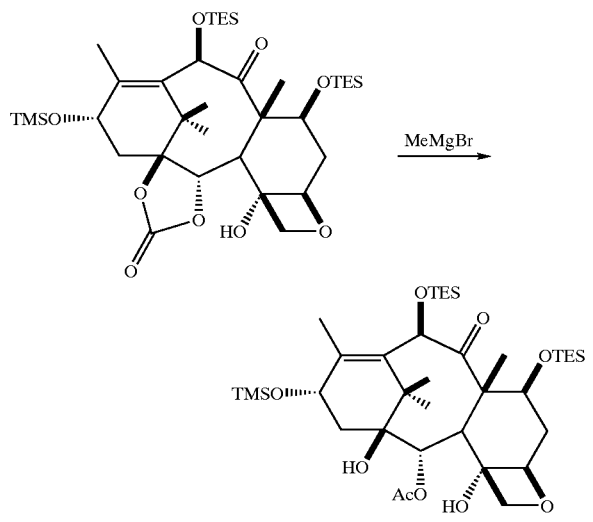

d. 13-O-Trimethylsilyl-7,10-bis-O-triethylsilyl-2-debenzoyl-2-acetyl-4,10-bisdeacetyl Baccatin (III)

To a solution of 13-O-trimethylsilyl-7,10-bis-O-triethylsilyl-2-debenzoyl-4,10-bisdeacetyl baccatin (III) (10.0 mg, 0.014 mmol) in THF (0.5 mL) at 0° C. was added 40 μL of a 3.4 M solution (10 eq) of MeMgBr in ether. The solution was stirred for 1 h at 0° C. under N₂ and saturated aqueous NaHCO, was added (1.0 mL). The mixture was extracted with EtOAc (3×5.0 mL) and the organic layer was washed with brine (5.0 mL), dried over anhydrous Na₂SO₄, filtered and concentrated under reduced pressure to give a crude solid (11.9 mg). Flash chromatography with 20% EtOAc in hexane gave pure 13-O-methylsilyl-7,10-bis-O-triethylsilyl-2-debenzoyl-2-acetyl-4,10-bisdeacetyl baccatin (III) (9.9 mg, 97.0%). m.p. 198–201_C, [α]²⁵_Na −39.9° (c 0.5, CHCl₃), ¹H NMR (CDCl₃, 300 MHz), δ 5.27 (d, J=5.5 Hz, 1H, H2), 5.22 (s, 1H, H10), 4.71 (m, 1H, H13), 4.58 (dd, J=2.8, 9.3 Hz, 1H, H5), 4.41 (d, J=7.7 Hz, 1H, H20α), 4.35 (d, J=7.1 Hz, 1H, H20β), 4.01 (dd, J=6.1, 11.6 Hz, 1H, H7), 3.74 (s, 1H, 4OH), 3.47 (d, J=5.5 Hz, 1H, H3), 2.45 (m, 1H, H6α, 2.24–2.04 (m, 2H, H14α H14β), 2.06 (s, 3H, 2Ac), 1.96 (m, 1H, H6β), 1.88 (s, 3H, Me18), 1.46 (s, 3H, Me19), 1.14 (s, 3H, Me17), 1.02 (s, 3H, Me16), 0.99–0.91 (m, 18H, SiCH₂CH₃), 0.67–0.56 (m, 12H, SiCH₂CH₃), 0.24 (s, 9H, SiCH₃).

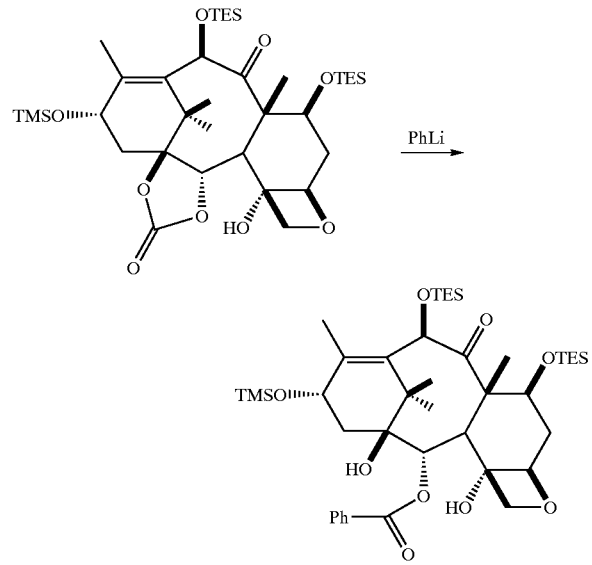

e. 13-O-Trimethylsilyl-7,10-bis-O-triethylsilyl-4,10-bisdeacetyl Baccatin (III)

To a solution of 13-O-trimethylsilyl-7,10-bis-O-triethylsilyl-2-debenzoyl-4,10-bisdeacetyl baccatin (III) 1,2-carbonate (10.0 mg, 0.014 mmol) in THF (0.5 mL) at −45° C. was added 78 μL of a 1.8 M solution of phenyllithium (10 eq) in 30% ether/70% cyclohexane. The solution was sired for 1 h at 45° C. under N₂ and saturated aqueous NaHCO was added (1.0 mL). The mixture was extracted with EtOAc (3×5.0 mL). The organic layer was washed with brine (5.0 mL), dried over anhydrous Na₂SO₄, filtered and concentrated under reduced pressure to give a crude solid (12.8 mg). Flash chromatography with 50% EtOAc in hexane gave pure 13-O-trimethylsilyl-7,10-bis-O-triethylsilyl-4,10-bisdeacetyl baccatin (III) (9.9 mg, 98.5%). m.p. 177–179° C., [α]²⁵_Na −44.5° (c 0.3, CHCl₃), ¹H NMR (CDCl₃, 300 MHz) δ 8.05 (d, J=7.2 Hz, 2H, benzoate ortho), 7.60–7.37 (m, 3H, aromatic), 5.61 (d, J=6.1 Hz, 1H, H2), 5.25 (s, 1H, H10), 4.74 (m, 1H, H13), 4.57 (dd, J=1.7, 9.3 Hz, 1H, H5), 4.38 (d, J=8,2 Hz, 1H, H20α), 4.12 (d, J=8.2 Hz, 1H, H20β), 4.05 (dd, J=6.1, 12.1 Hz, 1H, H7), 3.69 (d, J=6.0 Hz, 1H, H3), 2.55 (m, 1H, H6β), 2.42 (m, 2H, H14α, H14β), 2.04 (s, 3H, Me18), 1.99 (m, 1H, H6β), 1.64 (s, 3H, Me19), 1.20 (s, 3H, Me17), 1.04 (s, 3H, Me16), 1.01–0.90 (m, 18H, SiCH₂CH₃), 0.70–0.56 (m, 12H, SiCH₂CH₃).

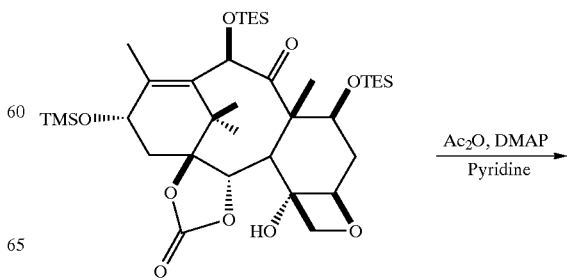

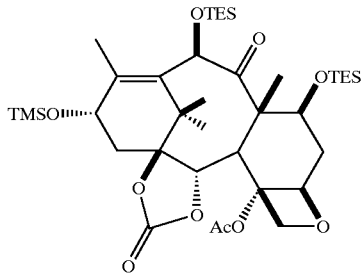

f. 13-O-Trimethylsilyl-7,10-bis-O-triethylsilyl-2-debenzoyl-10-deacetyl Baccatin (III) 1,2-Carbonate To a stirred solution of 13-O-trimethylsilyl-7,10-bis-O-triethylsilyl-2-debenzoyl-4,10-bisdeacetyl baccatin (III) 1,2-carbonate (8.0 mg, 0.011 mmol) in pyridine (0.5 mL) was added Ac$_2$O (100 μL) and DMAP (50 mg). The solution was heated at reflux under N$_2$ for 12 h, cooled to room temperature, and 15.0 mL of EtOAc was added. The organic layer was washed with 10% aqueous CuSO$_4$ and brine (5.0 mL), dried over anhydrous Na$_2$SO$_4$, filtered and concentrated under reduced pressure to give a crude solid (22.0 mg). Flash chromatography with 20% EtOAc in hexane gave 13-O-trimethylsilyl-7,10-bis-O-triethylsilyl-2-debenzoyl-10-deacetyl baccatin (III) 1,2-carbonate (4.4 mg, 53.0%) and 13-O-acetyl-7,10-bis-O-triethylsilyl-2-debenzoyl-10-deacetyl baccatin (III) 1,2-carbonate (2.3 mg, 27.8%).

EXAMPLE 17

10-Desacetoxybaccatin III

To a solution of baccatin III (20 mg: 0.034 mmol) in THF (0.09 mL) at 0° C. under nitrogen was added a solution of SmI$_2$ (0.1 M; 0.9 mL; 0.09 mmol) in THF. After stirring 45 minutes at 0° C. the flask was opened to the air, and the reaction mixture diluted with ethyl acetate (10 mL). The mixture was poured into aqueous HCl (0.2N; 25 mL), extracted with ethyl acetate, and the extract was washed successively with saturated aqueous NaHCO$_3$ and brine, dried over Na$_2$SO$_4$ and evaporated. The product was isolated by flash chromatography (SiO$_2$; 80% ethyl acetate-hexanes) affording 16.6 mg (92%) of 10-desacetoxybaccatin III which was recrystallized from CHCl$_3$-hexanes. m.p. 230–232° C. [α]$^{25}_D$=−103.6 (c=0.00195, CHCl$_3$). IR (cm$^{-1}$): 3100, 2970, 2950, 2900, 1750, 1710, 1460, 1370, 1320, 1270, 1255, 1110, 980, 890, 760, 700. $^1$H-nmr (500 MHz, CDCl$_3$) δ 8.11 (dd; 2H; J=8.4, 1.2 Hz; o-Bz); 7.61 (dt; 1H; J=7.5, 1.2 Hz; Bz); 7.48 (br t; 2H; J=7.8 Hz; m-Bz); 5.66 (br d; 1H; J=6.9 Hz; H-2β); 4.98 (br dd; 1H; J=9.4, 2; H-5α); 4.83 (br; 1H; w1/2 19 Hz; H-13β); 4.34 (dt; 1H; J=11.2, 7.8 Hz; H-7α); 4.31 (br d; 1H; J=8.4 Hz; H-20α); 4.17 (br d; 1H; J=6.9 Hz; H-3α); 4.15 (dd; 1H; J=8.4, 1Hz; H-20β); 3.84 (d; 1H; J=15.6 Hz; H-10α); 3.46 (ddd; 1H; J=15.6, 3.7, 1.6 Hz; H-10β); 2.64 (ddd; 1H; J=14.4, 9.4, 6.9 Hz; H-6α); 2.29 (s; 3H; 4-OAc); 2.28 (m; 2H; H-14α and H-14β); 1.95 (t; 3H; J=1.6 Hz; 18-Me); 1.94 (d, 1H; J=6.8 Hz; 13-OH); 1.79 (ddd; 1H; J=14.4, 11.2, 2.1 Hz; H-6β); 1.64 (s; 3H; 19-Me); 1.58 (s; 1H; 1-OH); 1.38 (d; 1H; J=7.8 Hz; 7-OH); 1.13 (s, 3H; 16-Me); 1.06 (s, 3H; 17-Me).

EXAMPLE 17

7-Triethylsilyl-10-desacetoxybaccatin III

To a stirred solution of 10-desacetoxybaccatin III (10.0 mg; 0.019 mmol) In anhydrous pyridine (0.05 mL) at room temperature and under nitrogen, triethylchlorosilane (15 L; 0.09 mmol) was added and the resulting mixture was stirred at room temperature for 48 h. After diluting with ethyl acetate (5 mL) the mixture was poured into saturated aqueous NaHCO$_3$ (25 mL) and extracted with ethyl acetate. The extract was washed successively with water, 10% aqueous CuSO$_4$ and brine, dried over Na$_2$SO$_4$ and evaporated. The product was purified by flash chromatography (SiO$_2$; 40% EA-hexanes) affording 11.1 mg (91%) of 7-triethylsilyl-10-desacetoxybaccatin III.

EXAMPLE 18

10-Desacetoxytaxol

To a stirred solution of taxol (35 mg; 0.041 mmol) in THF (0.1 mL) at 0° C. under nitrogen was added a solution of SmI$_2$ (0.1 M; 1.0 mL; 0.10 mmol) in THF. After stirring 45 minutes at 0° C. the flask was opened to the air and the reaction mixture diluted with ethyl acetate (10 mL). The mixture was poured into aqueous HCl (0.2N; 25 mL), extracted with ethyl acetate, and the extract was washed successively with saturated aqueous NaHCO$_3$ and brine, dried over Na$_2$SO$_4$ and evaporated. The product was isolated by flash chromatography (SiO$_2$; 80% ethyl acetate-hexanes) affording 29.4 mg (90%) of 10-desacetoxytaxol.

What we claim is:

1. A process for the preparation of a derivative or analog of baccatin III or 10-desacetyl baccatin III having the formula:

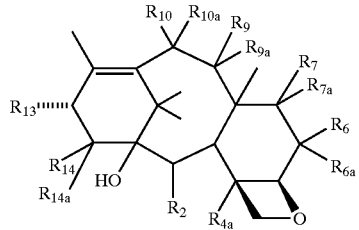

wherein
  $R_2$ is hydroxy or —OCOR$_{31}$;
  $R_{4a}$ is hydroxy or —OCOR$_{30}$, provided, however, that when $R_2$ is benzoyloxy, $R_{4a}$ is other than acetoxy;
  $R_6$ is hydrogen, alkyl, alkenyl, alkynyl, aryl, or heteroaryl, hydroxy, protected hydroxy or together with $R_{6a}$ forms an oxo;
  $R_{6a}$ is hydrogen, alkyl, alkenyl, alkynyl, aryl, or heteroaryl, hydroxy, protected hydroxy or together with $R_6$ forms an oxo;
  $R_7$ is hydrogen or together with $R_{7a}$ forms an oxo;
  $R_{7a}$ is hydrogen, halogen, protected hydroxy, —OCOR$_{29}$, hydroxy, or together with $R_7$ forms an oxo;
  $R_9$ is hydrogen;
  $R_{9a}$ is hydrogen, hydroxy, protected hydroxy, or —OCOR$_{29}$;
  $R_{10}$ is hydrogen or together with $R_{10a}$ forms an oxo;
  $R_{10a}$ is hydrogen, hydroxy, protected hydroxy, —OCOR$_{29}$, or together with $R_{10}$ forms an oxo;
  $R_{13}$ is hydroxy or protected hydroxy;
  $R_{14}$ is hydrogen, alkyl, alkenyl, alkynyl, aryl, or heteroaryl;
  $R_{14a}$ is hydrogen, alkyl, alkenyl, alkynyl, aryl, or heteroaryl, hydroxy, protected hydroxy or together with $R_1$ forms a carbonate; and
  $R_{29}$, $R_{30}$ and $R_{31}$ are independently hydrogen, alkyl, alkenyl, alkynyl, monocyclic aryl or monocyclic heteroaryl;

the process comprising selectively reducing a C2 benzoate substituent and/or a C4 acetate substituent of a derivative or analog of baccatin III or 10-desacetyl baccatin III with an aluminum hydride, a borohydride or a tetraalkylammonium salt to a corresponding C2 hydroxy substituent and/or C4 hydroxy substituent, and acylating the C2 hydroxy substituent and/or the C4 hydroxy substituent to convert the C2 hydroxy substituent to $R_{31}COO$— and/or convert the C4 hydroxy substituent to $R_{30}COO$— wherein $R_{31}$ and $R_{30}$ are as defined above.

2. The process of claim 1 wherein the derivative or analog of baccatin III or 10-desacetyl baccatin III has the formula:

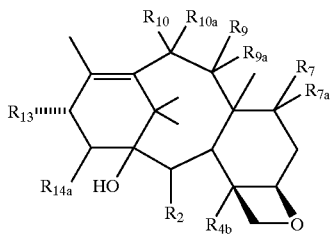

wherein $R_2$, $R_{4a}$, $R_7$, $R_{7a}$, $R_9$, $R_{9a}$, $R_{10}$, $R_{10a}$, $R_{13}$ and $R_{14a}$ are as defined in claim 1.

3. The process of claim 2 wherein $R_7$ is hydrogen; $R_{7a}$ is hydrogen, halogen, protected hydroxy, —$OCOR_{29}$, or hydroxy; and $R_{14a}$ is hydrogen.

4. The process of claim 1 wherein the C2 benzoate substituent and/or the C4 acetate substituent of the derivative of baccatin III or 10-desacetyl baccatin III are selectively reduced with an aluminum or boron hydride or a tetraalkyl ammonium salt.

5. The process of claim 4 wherein the C2 benzoate substituent and/or the C4 acetate substituent of the derivative of baccatin III or 10-desacetyl baccatin III are selectively reduced with lithium aluminum hydride, sodium bis(2-methoxyethoxy) aluminum hydride, lithium triethylborohydride, or tetrabutyl ammonium hydroxide.

6. The process of claim 1 wherein $R_{31}$ is p-fluoro-phenyl.

7. The process of claim 1 wherein $R_{31}$ is monocyclic aryl.

8. The process of claim 1 wherein $R_{31}$ is $C_1$–$C_6$ alkyl, $C_1$–$C_6$ alkanoxy or halogen substituted monocyclic aryl.

9. The process of claim 1 wherein the derivative or analog of baccatin III or 10-desacetyl baccatin III is prepared from a C1 hydroxy C2 benzoate derivative of baccatin III or 10-desacetyl baccatin III, the C1 hydroxy C2 benzoate derivative is reduced with sodium bis(2-methoxyethoxy) aluminum hydride to form a 1,2-diol derivative, the 1,2-diol is reacted with $Cl_2CO$ to form a 1,2-carbonate, and the 1,2-carbonate is reacted with a nucleophilic reagent to convert the C2 substituent to $R_{31}COO$—.

10. A process for the preparation of a 9-desoxo derivative or analog of baccatin III or 10-desacetyl baccatin, the process comprising selectively reducing a C2 benzoate substituent and/or a C4 acetate substituent of a derivative or analog of baccatin III or 10-desacetyl baccatin III with a reducing agent selected from the group consisting of an aluminum hydride, a borohydride or a tetraalkylammonium salt, to a corresponding C2 hydroxy substituent and/or C4 hydroxy substituent, and acylating the C2 hydroxy substituent and/or the C4 hydroxy substituent to convert the C2 hydroxy substituent to $R_{31}COO$— and/or convert the C4 hydroxy substituent to $R_{31}COO$— wherein $R_{31}$ and $R_{30}$ are independently hydrogen, alkyl, alkenyl, alkynyl, monocyclic aryl or monocyclic heteroaryl.

11. The process of claim 10 wherein the reducing agent is selected from the group consisting of lithium aluminum hydride, sodium bis(2-methoxyethoxy) aluminum hydride, lithium triethylborohydride, or tetrabutyl ammonium hydroxide.

12. The process of claim 10 wherein the C2 hydroxy substituent and/or the C4 hydroxy substituent is acylated with an anhydride or an acid chloride.

13. A process for the preparation of a derivative or analog of baccatin III or 10-desacetyl baccatin III from a 1,2-carbonate derivative of baccatin III or 10-desacetyl baccatin III, the process comprising reacting the 1,2-carbonate with a nucleophilic reagent to convert the C2 substituent to $R_{31}COO$— wherein $R_{31}$ is H, $C_1$–$C_6$ alkyl, $C_2$–$C_6$ alkenyl, $C_2$–$C_6$ alkynyl, monocyclic aryl, or monocyclic heteroaryl, and the 1,2-carbonate has the formula:

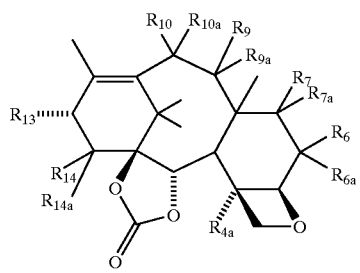

wherein:
$R_{4a}$ is hydroxy or —$OCOR_{30}$;
$R_6$ is hydrogen, alkyl, alkenyl, alkynyl, aryl, or heteroaryl, hydroxy, protected hydroxy or together with $R_{6a}$ forms an oxo;
$R_{6a}$ is hydrogen, alkyl, alkenyl, alkynyl, aryl, or heteroaryl, hydroxy, protected hydroxy or together with $R_6$ forms an oxo;
$R_7$ is hydrogen or together with $R_{7a}$ forms an oxo;
$R_{7a}$ is hydrogen, halogen, protected hydroxy, —$OCOR_{29}$, hydroxy, or together with $R_7$ forms an oxo;
$R_9$ is hydrogen;
$R_{9a}$ is hydrogen, hydroxy, protected hydroxy, or —$OCOR_{29}$;
$R_{10}$ is hydrogen or together with $R_{10a}$ forms an oxo;
$R_{10a}$ is hydrogen, hydroxy, protected hydroxy, —$OCOR_{29}$, or together with $R_{10}$ forms an oxo;
$R_{13}$ is hydroxy or protected hydroxy;
$R_{14}$ is hydrogen, alkyl, alkenyl, alkynyl, aryl, or heteroaryl;
$R_{14a}$ is hydrogen, alkyl, alkenyl, alkynyl, aryl, or heteroaryl, hydroxy, protected hydroxy or together with $R_1$ forms a carbonate; and
$R_{29}$ and $R_{30}$ are independently hydrogen, alkyl, alkenyl, alkynyl, monocyclic aryl or monocyclic heteroaryl.

14. The process of claim 13 wherein the 1,2-carbonate has the formula:

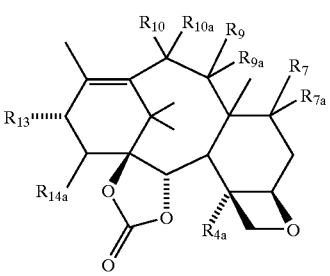

wherein $R_{4a}$, $R_7$, $R_{7a}$, $R_9$, $R_{9a}$, $R_{10}$, $R_{10a}$, $R_{13}$ and $R_{14a}$ are as defined in claim 13.

15. The process of claim 14 wherein $R_7$ is hydrogen; $R_{7a}$ is hydrogen, halogen, protected hydroxy, —$OCOR_{29}$, or hydroxy; and $R_{14a}$ is hydrogen.

16. The process of claim 13 wherein the nucleophilic reagent is a Grignard reagent or an alkyllithium reagent.

17. A compound having the formula:

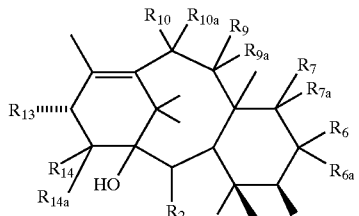

wherein:
- $R_2$ is hydroxy or —$OCOR_{31}$;
- $R_{4a}$ is hydroxy or —$OCOR_{31}$, provided, however, that when $R_2$ is benzoyloxy, $R_{4a}$ is other than acetoxy;
- $R_6$ is hydrogen, alkyl, alkenyl, alkynyl, aryl, or heteroaryl, hydroxy, protected hydroxy or together with $R_{6a}$ forms an oxo;
- $R_{6a}$ is hydrogen, alkyl, alkenyl, alkynyl, aryl, or heteroaryl, hydroxy, protected hydroxy or together with $R_6$ forms an oxo;
- $R_7$ is hydrogen or together with $R_{7a}$ forms an oxo;
- $R_{7a}$ is hydrogen, halogen, —$OCOR_{29}$, or together with $R_7$ forms an oxo;
- $R_9$ is hydrogen;
- $R_{9a}$ is hydrogen, hydroxy, protected hydroxy, or —$OCOR_{30}$;
- $R_{10}$ is hydrogen or together with $R_{10a}$ forms an oxo;
- $R_{10a}$ is hydrogen, hydroxy, protected hydroxy, —$OCOR_{30}$, or together with $R_{10}$ forms an oxo;
- $R_{13}$ is hydroxy or protected hydroxy;
- $R_{14}$ is hydrogen, alkyl, alkenyl, alkynyl, aryl, or heteroaryl;
- $R_{14a}$ is hydrogen, alkyl, alkenyl, alkynyl, aryl, or heteroaryl, hydroxy, protected hydroxy or together with $R_1$ forms a carbonate;
- $R_{29}$ is hydrogen, alkenyl, alkynyl, or monocyclic heteroaryl; and
- $R_{30}$ and $R_{31}$ are independently hydrogen, alkyl, alkenyl, alkynyl, monocyclic aryl or monocyclic heteroaryl.

18. The compound of claim 17 having the formula:

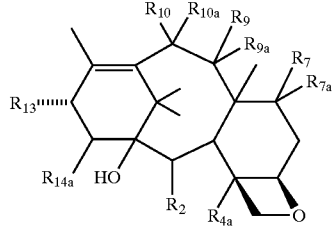

wherein $R_2$, $R_{4a}$, $R_7$, $R_{7a}$, $R_9$, $R_{9a}$, $R_{10}$, $R_{10a}$, $R_{13}$ and $R_{14a}$ are as defined in claim 17.

19. A compound having the formula:

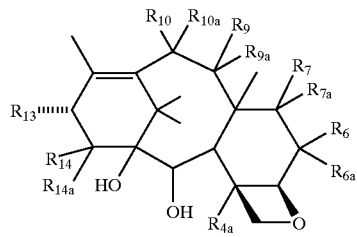

wherein:
- $R_{4a}$ is hydroxy or —$OCOR_{30}$;
- $R_6$ is hydrogen, alkyl, alkenyl, alkynyl, aryl, or heteroaryl, hydroxy, protected hydroxy or together with $R_{6a}$ forms an oxo;
- $R_{6a}$ is hydrogen, alkyl, alkenyl, alkynyl, aryl, or heteroaryl, hydroxy, protected hydroxy or together with $R_6$ forms an oxo;
- $R_7$ is hydrogen or together with $R_{7a}$ forms an oxo;
- $R_{7a}$ is hydrogen, halogen, protected hydroxy, —$OCOR_{29}$, hydroxy, or together with $R_7$ forms an oxo;
- $R_9$ is hydrogen;
- $R_{9a}$ is hydrogen, hydroxy, protected hydroxy, or —$OCOR_{29}$;
- $R_{10}$ is hydrogen or together with $R_{10a}$ forms an oxo;
- $R_{10a}$ is hydrogen, hydroxy, protected hydroxy, —$OCOR_{29}$, or together with $R_{10}$ forms an oxo;
- $R_{13}$ is hydroxy or protected hydroxy;
- $R_{14}$ is hydrogen, alkyl, alkenyl, alkynyl, aryl, or heteroaryl;
- $R_{14a}$ is hydrogen, alkyl, alkenyl, alkynyl, aryl, or heteroaryl, hydroxy, protected hydroxy or together with $R_1$ forms a carbonate; and
- $R_{29}$ and $R_{30}$ are independently hydrogen, alkyl, alkenyl, alkynyl, monocyclic aryl or monocyclic heteroaryl.

20. The compound of claim 19 having the formula:

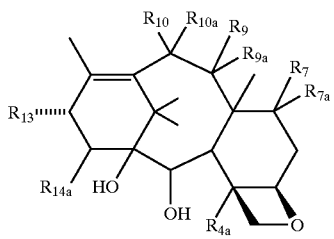

wherein $R_{4a}$, $R_7$, $R_{7a}$, $R_9$, $R_{9a}$, $R_{10}$, $R_{10a}$, $R_{13}$ and $R_{14a}$ are as defined in claim 19.

21. A compound having the formula:

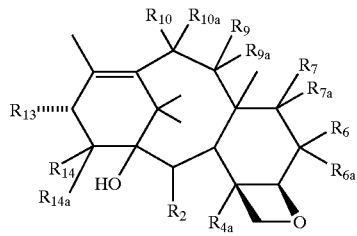

wherein:
- $R_2$ is hydroxy or —$OCOR_{31}$;
- $R_{4a}$ is hydroxy or —$OCOR_{30}$, provided, however, that when $R_2$ is benzoyloxy, $R_{4a}$ is other than acetoxy;
- $R_6$ is hydrogen, alkyl, alkenyl, alkynyl, aryl, or heteroaryl, hydroxy, protected hydroxy or together with $R_{6a}$ forms an oxo;
- $R_{6a}$ is hydrogen, alkyl, alkenyl, alkynyl, aryl, or heteroaryl, hydroxy, protected hydroxy or together with $R_6$ forms an oxo;
- $R_7$ is hydrogen or together with $R_{7a}$ forms an oxo;
- $R_{7a}$ is hydrogen, halogen, protected hydroxy, —$OCOR_{29}$, hydroxy, or together with $R_7$ forms an oxo;
- $R_9$ is hydrogen;
- $R_{9a}$ is hydrogen, hydroxy, protected hydroxy, or —$OCOR_{29}$;
- $R_{10}$ is hydrogen or together with $R_{10a}$ forms an oxo;
- $R_{10a}$ is hydrogen, hydroxy, protected hydroxy, —$OCOR_{29}$, or together with $R_{10}$ forms an oxo;
- $R_{13}$ is hydroxy or protected hydroxy;
- $R_{14}$ is hydrogen, alkyl, alkenyl, alkynyl, aryl, or heteroaryl;
- $R_{14a}$ is hydrogen, alkyl, alkenyl, alkynyl, aryl, or heteroaryl, hydroxy, protected hydroxy or together with $R_1$ forms a carbonate; and
- $R_{29}$, $R_{30}$ and $R_{31}$ are independently hydrogen, alkyl, alkenyl, alkynyl, monocyclic aryl or monocyclic heteroaryl.

22. The compound of claim 21 having the formula:

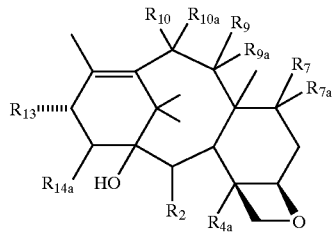

wherein $R_2$, $R_{4a}$, $R_7$, $R_{7a}$, $R_9$, $R_{9a}$, $R_{10}$, $R_{10a}$, $R_{13}$ and $R_{14a}$ are as defined in claim 21.

23. A compound having the formula:

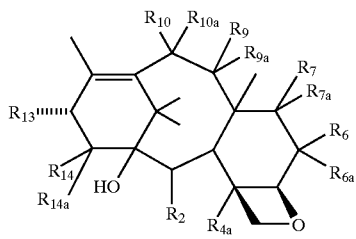

wherein:
- $R_2$ is hydroxy or —$OCOR_{31}$;
- $R_{4a}$ is hydroxy or —$OCOR_{31}$, provided, however, that when $R_2$ is benzoyloxy, $R_{4a}$ is other than acetoxy;
- $R_6$ is hydrogen, alkyl, alkenyl, alkynyl, aryl, or heteroaryl, hydroxy, protected hydroxy or together with $R_{6a}$ forms an oxo;
- $R_{6a}$ is hydrogen, alkyl, alkenyl, alkynyl, aryl, or heteroaryl, hydroxy, protected hydroxy or together with $R_6$ forms an oxo;
- $R_7$ is hydrogen or together with $R_{7a}$ forms an oxo;
- $R_{7a}$ is hydrogen, halogen, —$OCOR_{30}$, or together with $R_7$ forms an oxo;
- $R_9$ is hydrogen;
- $R_{9a}$ is hydrogen, hydroxy, protected hydroxy, or —$OCOR_{29}$;
- $R_{10}$ is hydrogen or together with $R_{10a}$ forms an oxo;
- $R_{10a}$ is hydrogen, hydroxy, protected hydroxy, —$OCOR_{30}$, or together with $R_{10}$ forms an oxo;
- $R_{13}$ is hydroxy or protected hydroxy;
- $R_{14}$ is hydrogen, alkyl, alkenyl, alkynyl, aryl, or heteroaryl;
- $R_{14a}$ is hydrogen, alkyl, alkenyl, alkynyl, aryl, or heteroaryl, hydroxy, protected hydroxy or together with $R_1$ forms a carbonate;
- $R_{29}$ is hydrogen, alkenyl, alkynyl, or monocyclic heteroaryl; and
- $R_{30}$ and $R_{31}$ are independently hydrogen, alkyl, alkenyl, alkynyl, monocyclic aryl or monocyclic heteroaryl.

24. The compound of claim 23 having the formula:

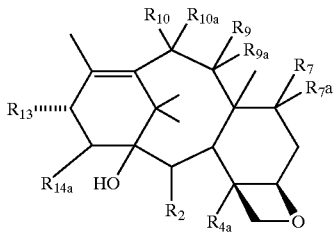

wherein $R_2$, $R_{4a}$, $R_7$, $R_{7a}$, $R_9$, $R_{9a}$, $R_{10}$, $R_{10a}$, $R_{13}$ and $R_{14a}$ are as defined in claim 23.

25. A compound having the formula:

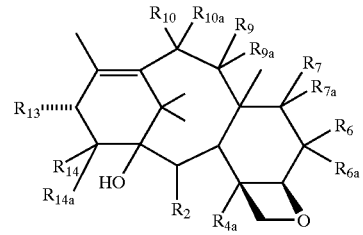

wherein:
- $R_2$ is hydroxy or —$OCOR_{31}$;
- $R_{4a}$ is hydroxy or —$OCOR_{31}$, provided, however, that when $R_2$ is benzoyloxy, $R_{4a}$ is other than acetoxy;
- $R_6$ is hydrogen, alkyl, alkenyl, alkynyl, aryl, or heteroaryl, hydroxy, protected hydroxy or together with $R_{6a}$ forms an oxo;
- $R_{6a}$ is hydrogen, alkyl, alkenyl, alkynyl, aryl, or heteroaryl, hydroxy, protected hydroxy or together with $R_6$ forms an oxo;
- $R_7$ is hydrogen or together with $R_{7a}$ forms an oxo;
- $R_{7a}$ is hydrogen, halogen, protected hydroxy, —$OCOR_{30}$, hydroxy, or together with $R_7$ forms an oxo;
- $R_9$ is hydrogen;
- $R_{9a}$ is hydrogen, hydroxy, protected hydroxy, or —$OCOR_{30}$;
- $R_{10}$ is hydrogen or together with $R_{10a}$ forms an oxo;
- $R_{10a}$ is hydrogen, hydroxy, protected hydroxy, or —$OCOR_{29}$;
- $R_{13}$ is hydroxy or protected hydroxy;

$R_{14}$ is hydrogen, alkyl, alkenyl, alkynyl, aryl, or heteroaryl;

$R_{14a}$ is hydrogen, alkyl, alkenyl, alkynyl, aryl, or heteroaryl, hydroxy, protected hydroxy or together with $R_1$ forms a carbonate;

$R_{29}$ is hydrogen, alkenyl, alkynyl, or monocyclic heteroaryl; and $R_{30}$ and $R_{31}$ are independently hydrogen, alkyl, alkenyl, alkynyl, monocyclic aryl or monocyclic heteroaryl.

26. The compound of claim 25 having the formula:

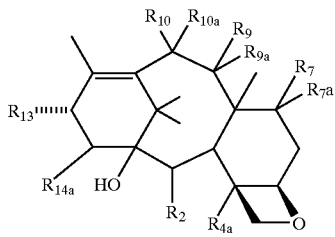

wherein $R_2$, $R_{4a}$, $R_7$, $R_{7a}$, $R_9$, $R_{9a}$, $R_{10}$, $R_{10a}$, $R_{13}$ and $R_{14a}$ are as defined in claim 25.

27. A compound having the formula:

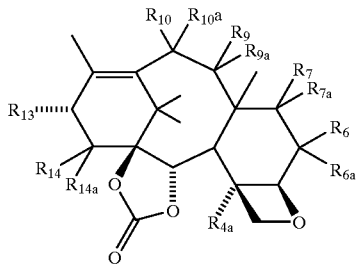

wherein:

$R_{4a}$ is hydroxy or —$OCOR_{30}$;

$R_6$ is hydrogen, alkyl, alkenyl, alkynyl, aryl, or heteroaryl, hydroxy, protected hydroxy or together with $R_{6a}$ forms an oxo;

$R_{6a}$ is hydrogen, alkyl, alkenyl, alkynyl, aryl, or heteroaryl, hydroxy, protected hydroxy or together with $R_6$ forms an oxo;

$R_7$ is hydrogen or together with $R_{7a}$ forms an oxo;

$R_{7a}$ is hydrogen, halogen, protected hydroxy, —$OCOR_{29}$, hydroxy, or together with $R_7$ forms an oxo;

$R_9$ is hydrogen;

$R_{9a}$ is hydrogen, hydroxy, protected hydroxy, or —$OCOR_{29}$;

$R_{10}$ is hydrogen or together with $R_{10a}$ forms an oxo;

$R_{10a}$ is hydrogen, hydroxy, protected hydroxy, —$OCOR_{29}$, or together with $R_{10}$ forms an oxo;

$R_{13}$ is hydroxy or protected hydroxy;

$R_{14}$ is hydrogen, alkyl, alkenyl, alkynyl, aryl, or heteroaryl;

$R_{14a}$ is hydrogen, alkyl, alkenyl, alkynyl, aryl, or heteroaryl, hydroxy, protected hydroxy or together with $R_1$ forms a carbonate; and $R_{29}$ and $R_{30}$ are independently hydrogen, alkyl, alkenyl, alkynyl, monocyclic aryl or monocyclic heteroaryl.

28. The compound of claim 27 having the formula:

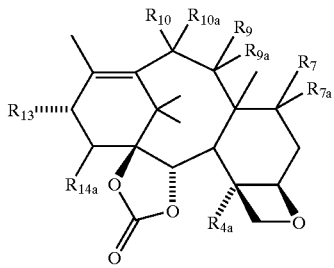

wherein $R_{4a}$, $R_7$, $R_{7a}$, $R_9$, $R_{9a}$, $R_{10}$, $R_{10a}$, $R_{13}$ and $R_{14a}$ are as defined in claim 27.

29. A process for the preparation of a derivative or analog of baccatin III or 10-desacetyl baccatin III having the formula:

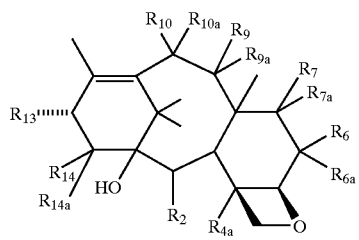

wherein $R_2$ is hydroxy or —$OCOR_{31}$;

$R_{4a}$ is hydroxy or —$OCOR_{30}$, provided, however, that when $R_2$ is benzoyloxy, $R_{4a}$ is other than acetoxy;

$R_6$ is hydrogen, alkyl, alkenyl, alkynyl, aryl, or heteroaryl, hydroxy, protected hydroxy or together with $R_{6a}$ forms an oxo;

$R_{6a}$ is hydrogen, alkyl, alkenyl, alkynyl, aryl, or heteroaryl, hydroxy, protected hydroxy or together with $R_6$ forms an oxo;

$R_7$ is hydrogen or together with $R_{7a}$ forms an oxo;

$R_{7a}$ is hydrogen, halogen, protected hydroxy, —$OCOR_{29}$, hydroxy, or together with $R_7$ forms an oxo;

$R_9$ is hydrogen or together with $R_{9a}$ forms an oxo;

$R_{9a}$ is hydrogen, hydroxy, protected hydroxy, —$OCOR_{29}$, or together with $R_9$ forms an oxo;

$R_{10}$ is hydrogen or together with $R_{10a}$ forms an oxo;

$R_{10a}$ is hydrogen, hydroxy, protected hydroxy, —$OCOR_{29}$, or together with $R_{10}$ forms an oxo;

$R_{13}$ is hydroxy or protected hydroxy;

$R_{14}$ is hydrogen;

$R_{14a}$ is hydroxy, protected hydroxy or together with $R_1$ forms a carbonate; and $R_{29}$, $R_{30}$ and $R_{31}$ are independently hydrogen, alkyl, alkenyl, alkynyl, monocyclic aryl or monocyclic heteroaryl;

the process comprising selectively reducing a C2 benzoate substituent and/or a C4 acetate substituent of a derivative or analog of baccatin III or 10-desacetyl baccatin III with an aluminum hydride, a borohydride or a tetraalkylammonium salt to a corresponding C2 hydroxy substituent and/or C4 hydroxy substituent, and acylating the C2 hydroxy substituent and/or the C4 hydroxy substituent to convert the C2 hydroxy substituent to $R_{31}COO$— and/or convert the C4 hydroxy substituent to $R_{30}COO$— wherein $R_{31}$ and $R_{30}$ are as defined above.

30. The process of claim 29 wherein the derivative or analog of baccatin III or 10-desacetyl baccatin III has the formula:

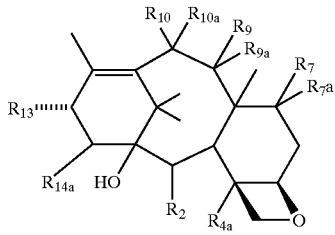

wherein $R_2$, $R_{4a}$, $R_7$, $R_{7a}$, $R_9$, $R_{9a}$, $R_{10}$, $R_{10a}$, $R_{13}$ and $R_{14a}$ are as defined in claim 29.

31. The process of claim 30 wherein $R_7$ is hydrogen and $R_{7a}$ is hydrogen, halogen, protected hydroxy, —$OCOR_{29}$, or hydroxy.

32. The process of claim 29 wherein the C2 benzoate substituent and/or the C4 acetate substituent of the derivative of baccatin III or 10-desacetyl baccatin III are selectively reduced with an aluminum or boron hydride or a tetraalkyl ammonium salt.

33. The process of claim 32 wherein the C2 benzoate substituent and/or the C4 acetate substituent of the derivative of baccatin III or 10-desacetyl baccatin III are selectively reduced with lithium aluminum hydride, sodium bis(2-methoxyethoxy) aluminum hydride, lithium triethylborohydride, or tetrabutyl ammonium hydroxide.

34. The process of claim 29 wherein $R_{31}$ is p-fluorophenyl.

35. The process of claim 29 wherein $R_{31}$ is monocyclic aryl.

36. The process of claim 29 wherein $R_{31}$ is $C_1$–$C_6$ alkyl, $C_1$–$C_6$ alkanoxy or halogen substituted monocyclic aryl.

37. The process of claim 29 wherein the derivative or analog of baccatin III or 10-desacetyl baccatin III is prepared from a C1 hydroxy C2 benzoate derivative of baccatin III or 10-desacetyl baccatin III, the C1 hydroxy C2 benzoate derivative is reduced with sodium bis(2-methoxyethoxy) aluminum hydride to form a 1,2-diol derivative, the 1,2-diol is reacted with $Cl_2CO$ to form a 1,2-carbonate, and the 1,2-carbonate is reacted with a nucleophilic reagent to convert the C2 substituent to $R_{31}COO$—.

38. A process for the preparation of a 14-hydroxy derivative or analog of baccatin III or 10-desacetyl baccatin, the process comprising selectively reducing a C2 benzoate substituent and/or a C4 acetate substituent of a derivative or analog of baccatin III or 10-desacetyl baccatin III with a reducing agent selected from the group consisting of an aluminum hydride, a borohydride or a tetraalkylammonium salt, to a corresponding C2 hydroxy substituent and/or C4 hydroxy substituent, and acylating the C2 hydroxy substituent and/or the C4 hydroxy substituent to convert the C2 hydroxy substituent to $R_{31}COO$— and/or convert the C4 hydroxy substituent to $R_{31}COO$— wherein $R_{31}$ and $R_{30}$ are independently hydrogen, alkyl, alkenyl, alkynyl, monocyclic aryl or monocyclic heteroaryl.

39. The process of claim 38 wherein the reducing agent is selected from the group consisting of lithium aluminum hydride, sodium bis(2-methoxyethoxy) aluminum hydride, lithium triethylborohydride, or tetrabutyl ammonium hydroxide.

40. The process of claim 38 wherein the C2 hydroxy substituent and/or the C4 hydroxy substituent is acylated with an anhydride or an acid chloride.

41. A process for the preparation of a derivative or analog of baccatin III or 10-desacetyl baccatin III from a 1,2-carbonate derivative of baccatin III or 10-desacetyl baccatin III, the process comprising reacting the 1,2-carbonate with a nucleophilic reagent to convert the C2 substituent to $R_{31}COO$— wherein $R_{31}$ is H, $C_1$–$C_6$ alkyl, $C_2$–$C_6$ alkenyl, $C_2$–$C_6$ alkynyl, monocyclic aryl, or monocyclic heteroaryl, and the 1,2-carbonate has the formula:

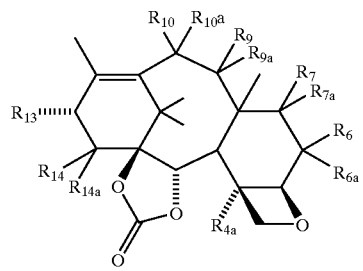

wherein:
$R_{4a}$ is hydroxy or —$OCOR_{30}$;
$R_6$ is hydrogen, alkyl, alkenyl, alkynyl, aryl, or heteroaryl, hydroxy, protected hydroxy or together with $R_{6a}$ forms an oxo;
$R_{6a}$ is hydrogen, alkyl, alkenyl, alkynyl, aryl, or heteroaryl, hydroxy, protected hydroxy or together with $R_6$ forms an oxo;
$R_7$ is hydrogen or together with $R_{7a}$ forms an oxo;
$R_{7a}$ is hydrogen, halogen, protected hydroxy, —$OCOR_{29}$, hydroxy, or together with $R_7$ forms an oxo;
$R_9$ is hydrogen or together with $R_{9a}$ forms an oxo;
$R_{9a}$ is hydrogen, hydroxy, protected hydroxy, or —$OCOR_{29}$ or together with $R_9$ forms an oxo;
$R_{10}$ is hydrogen or together with $R_{10a}$ forms an oxo;
$R_{10a}$ is hydrogen, hydroxy, protected hydroxy, —$OCOR_{29}$, or together with $R_{10}$ forms an oxo;
$R_{13}$ is hydroxy or protected hydroxy;
$R_{14}$ is hydrogen;
$R_{14a}$ is hydroxy, protected hydroxy or together with $R_1$ forms a carbonate; and
$R_{29}$, $R_{30}$ and $R_{31}$ are independently hydrogen, alkyl, alkenyl, alkynyl, monocyclic aryl or monocyclic heteroaryl.

42. The process of claim 41 wherein the 1,2-carbonate has the formula:

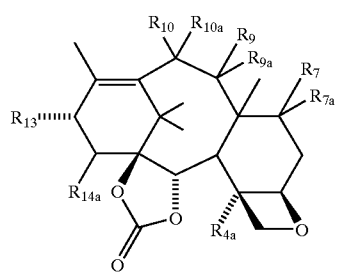

wherein $R_{4a}$, $R_7$, $R_{7a}$, $R_9$, $R_{9a}$, $R_{10}$, $R_{10a}$, $R_{13}$ and $R_{14a}$ are as defined in claim 41.

43. The process of claim 42 wherein $R_7$ is hydrogen; $R_7a$ is hydrogen, halogen, protected hydroxy, —$OCOR_{29}$, or hydroxy; and $R_{14a}$ is hydrogen.

44. The process of claim 41 wherein the nucleophilic reagent is a Grignard reagent or an alkyllithium reagent.

45. A compound having the formula:

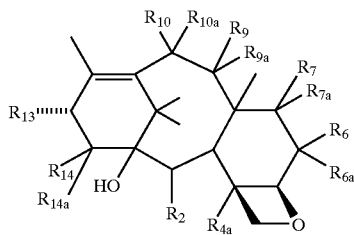

wherein:
- $R_2$ is hydroxy or —$OCOR_{31}$;
- $R_{4a}$ is hydroxy or —$OCOR_{31}$, provided, however, that when $R_2$ is benzoyloxy, $R_{4a}$ is other than acetoxy;
- $R_6$ is hydrogen, alkyl, alkenyl, alkynyl, aryl, or heteroaryl, hydroxy, protected hydroxy or together with $R_{6a}$ forms an oxo;
- $R_{6a}$ is hydrogen, alkyl, alkenyl, alkynyl, aryl, or heteroaryl, hydroxy, protected hydroxy or together with $R_6$ forms an oxo;
- $R_7$ is hydrogen or together with $R_{7a}$ forms an oxo;
- $R_{7a}$ is hydrogen, halogen, —$OCOR_{29}$, or together with $R_7$ forms an oxo;
- $R_9$ is hydrogen or together with $R_{9a}$ forms an oxo;
- $R_{9a}$ is hydrogen, hydroxy, protected hydroxy, or —$OCOR_{30}$, or together with $R_9$ forms an oxo;
- $R_{10}$ is hydrogen or together with $R_{10a}$ forms an oxo;
- $R_{10a}$ is hydrogen, hydroxy, protected hydroxy, or —$OCOR_{30}$, or together with $R_{10}$ forms an oxo;
- $R_{13}$ is protected hydroxy;
- $R_{14}$ is hydrogen;
- $R_{14a}$ is hydroxy, protected hydroxy or together with $R_1$ forms a carbonate;
- $R_{29}$ is hydrogen, alkenyl, alkynyl, or monocyclic heteroaryl; and
- $R_{30}$ and $R_{31}$ are independently hydrogen, alkyl, alkenyl, alkynyl, monocyclic aryl or monocyclic heteroaryl.

46. The compound of claim 45 having the formula:

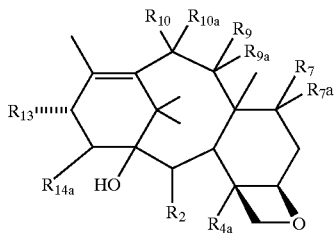

wherein $R_2$, $R_{4a}$, $R_7$, $R_{7a}$, $R_9$, $R_{9a}$, $R_{10}$, $R_{10a}$, $R_{13}$ and $R_{14a}$ are as defined in claim 45.

47. A compound having the formula:

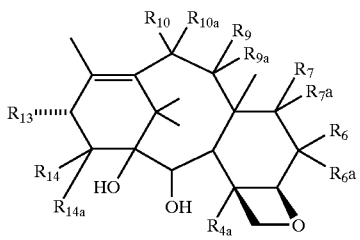

wherein:
- $R_{4a}$ is hydroxy or —$OCOR_{30}$;
- $R_6$ is hydrogen, alkyl, alkenyl, alkynyl, aryl, or heteroaryl, hydroxy, protected hydroxy or together with $R_{6a}$ forms an oxo;
- $R_{6a}$ is hydrogen, alkyl, alkenyl, alkynyl, aryl, or heteroaryl, hydroxy, protected hydroxy or together with $R_6$ forms an oxo;
- $R_7$ is hydrogen or together with $R_{7a}$ forms an oxo;
- $R_{7a}$ is hydrogen, halogen, protected hydroxy, —$OCOR_{29}$, hydroxy, or together with $R_7$ forms an oxo;
- $R_9$ is hydrogen;
- $R_{9a}$ is hydrogen, hydroxy, protected hydroxy, or —$OCOR_{29}$;
- $R_{10}$ is hydrogen or together with $R_{10a}$ forms an oxo;
- $R_{10a}$ is hydrogen, hydroxy, protected hydroxy, —$OCOR_{29}$, or together with $R_{10}$ forms an oxo;
- $R_{13}$ is hydroxy or protected hydroxy;
- $R_{14}$ is hydrogen;
- $R_{14a}$ is hydroxy, protected hydroxy or together with $R_1$ forms a carbonate; and
- $R_{29}$, $R_{30}$ and $R_{31}$ are independently hydrogen, alkyl, alkenyl, alkynyl, monocyclic aryl or monocyclic heteroaryl.

48. The compound of claim 47 having the formula:

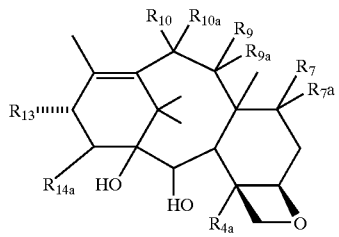

wherein $R_{4a}$, $R_7$, $R_{7a}$, $R_9$, $R_{9a}$, $R_{10}$, $R_{10a}$, $R_{13}$ and $R_{14a}$ are as defined in claim 47.

49. A compound having the formula:

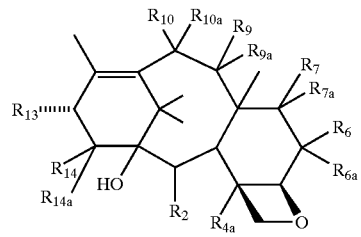

wherein:
- $R_2$ is hydroxy or —$OCOR_{31}$;
- $R_{4a}$ is hydroxy or —$OCOR_{30}$, provided, however, that when $R_2$ is benzoyloxy, $R_{4a}$ is other than acetoxy;
- $R_6$ is hydrogen, alkyl, alkenyl, alkynyl, aryl, or heteroaryl, hydroxy, protected hydroxy or together with $R_{6a}$ forms an oxo;
- $R_{6a}$ is hydrogen, alkyl, alkenyl, alkynyl, aryl, or heteroaryl, hydroxy, protected hydroxy or together with $R_6$ forms an oxo;
- $R_7$ is hydrogen or together with $R_{7a}$ forms an oxo;
- $R_{7a}$ is hydrogen, halogen, protected hydroxy, —$OCOR_{29}$, hydroxy, or together with $R_7$ forms an oxo;
- $R_9$ is hydrogen or together with $R_{9a}$ forms an oxo;
- $R_{9a}$ is hydrogen, hydroxy, protected hydroxy, or —$OCOR_{29}$, or together with $R_9$ forms an oxo;

$R_{10}$ is hydrogen or together with $R_{10a}$ forms an oxo;

$R_{10a}$ is hydrogen, hydroxy, protected hydroxy, —OCOR$_{29}$, or together with $R_{10}$ forms an oxo;

$R_{13}$ is protected hydroxy;

$R_{14}$ is hydrogen, alkyl, alkenyl, alkynyl, aryl, or heteroaryl;

$R_{14a}$ is hydrogen, alkyl, alkenyl, alkynyl, aryl, or heteroaryl, hydroxy, protected hydroxy or together with $R_1$ forms a carbonate; and $R_{29}$, $R_{30}$ and $R_{31}$ are independently hydrogen, alkyl, alkenyl, alkynyl, monocyclic aryl or monocyclic heteroaryl.

50. The compound of claim 49 having the formula:

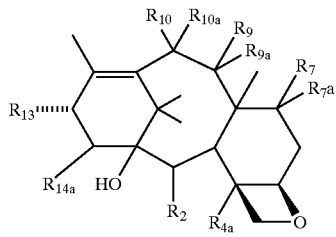

wherein $R_2$, $R_{4a}$, $R_7$, $R_{7a}$, $R_9$, $R_{9a}$, $R_{10}$, $R_{10a}$, $R_{13}$ and $R_{14a}$ are as defined in claim 49.

51. A compound having the formula:

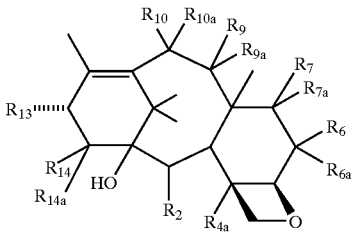

wherein:

$R_2$ is hydroxy or —OCOR$_{31}$;

$R_{4a}$ is hydroxy or —OCOR$_{31}$, provided, however, that when $R_2$ is benzoyloxy, $R_{4a}$ is other than acetoxy;

$R_6$ is hydrogen, alkyl, alkenyl, alkynyl, aryl, or heteroaryl, hydroxy, protected hydroxy or together with $R_{6a}$ forms an oxo;

$R_{6a}$ is hydrogen, alkyl, alkenyl, alkynyl, aryl, or heteroaryl, hydroxy, protected hydroxy or together with $R_6$ forms an oxo;

$R_7$ is hydrogen or together with $R_{7a}$ forms an oxo;

$R_{7a}$ is hydrogen, halogen, protected hydroxy, —OCOR$_{30}$, hydroxy, or together with $R_7$ forms an oxo;

$R_9$ is hydrogen;

$R_{9a}$ is hydrogen, hydroxy, protected hydroxy, or —OCOR$_{29}$;

$R_{10}$ is hydrogen or together with $R_{10a}$ forms an oxo;

$R_{10a}$ is hydrogen, hydroxy, protected hydroxy, —OCOR$_{30}$, or together with $R_{10}$ forms an oxo;

$R_{13}$ is hydroxy or protected hydroxy;

$R_{14}$ is hydrogen;

$R_{14a}$ is hydroxy, protected hydroxy or together with $R_1$ forms a carbonate;

$R_{29}$ is hydrogen, alkenyl, alkynyl, or monocyclic heteroaryl; and $R_{30}$ and $R_{31}$ are independently hydrogen, alkyl, alkenyl, alkynyl, monocyclic aryl or monocyclic heteroaryl.

52. The compound of claim 51 having the formula:

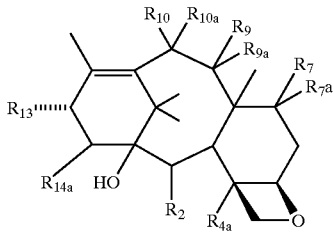

wherein $R_2$, $R_{4a}$, $R_7$, $R_{7a}$, $R_9$, $R_{9a}$, $R_{10}$, $R_{10a}$, $R_{13}$ and $R_{14a}$ are as defined in claim 51.

53. A compound having the formula:

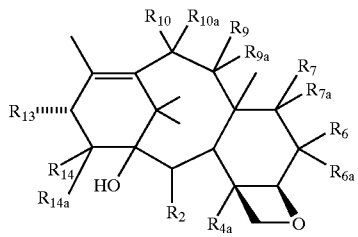

wherein:

$R_2$ is hydroxy or —OCOR$_{31}$;

$R_{4a}$ is hydroxy or —OCOR$_{31}$, provided, however, that when $R_2$ is benzoyloxy, $R_{4a}$ is other than acetoxy;

$R_6$ is hydrogen, alkyl, alkenyl, alkynyl, aryl, or heteroaryl, hydroxy, protected hydroxy or together with $R_{6a}$ forms an oxo;

$R_{6a}$ is hydrogen, alkyl, alkenyl, alkynyl, aryl, or heteroaryl, hydroxy, protected hydroxy or together with $R_6$ forms an oxo;

$R_7$ is hydrogen or together with $R_{7a}$ forms an oxo;

$R_{7a}$ is hydrogen, halogen, protected hydroxy, —OCOR$_{30}$, hydroxy, or together with $R_7$ forms an oxo;

$R_9$ is hydrogen or together with $R_{9a}$ forms an oxo;

$R_{9a}$ is hydrogen, hydroxy, protected hydroxy, —OCOR$_{30}$, or together with $R_9$ forms an oxo;

$R_{10}$ is hydrogen;

$R_{10a}$ is hydrogen, protected hydroxy, or —OCOR$_{29}$;

$R_{13}$ is protected hydroxy;

$R_{14}$ is hydrogen;

$R_{14a}$ is hydroxy, protected hydroxy or together with $R_1$ forms a carbonate;

$R_{29}$ is hydrogen, alkenyl, alkynyl, or monocyclic heteroaryl; and $R_{30}$ and $R_{31}$ are independently hydrogen, alkyl, alkenyl, alkynyl, monocyclic aryl or monocyclic heteroaryl.

54. The compound of claim 53 having the formula:

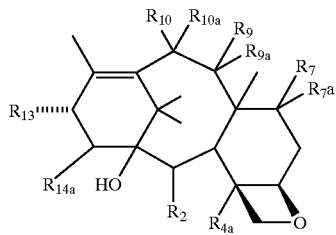

wherein $R_2$, $R_{4a}$, $R_7$, $R_{7a}$, $R_9$, $R_{9a}$, $R_{10}$, $R_{10a}$, $R_{13}$ and $R_{14a}$ are as defined in claim 53.

55. A compound having the formula:

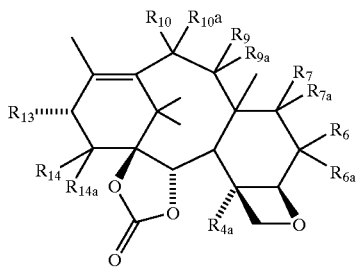

wherein:
$R_{4a}$ is hydroxy or —$OCOR_{30}$;
$R_6$ is hydrogen, alkyl, alkenyl, alkynyl, aryl, or heteroaryl, hydroxy, protected hydroxy or together with $R_{6a}$ forms an oxo;
$R_{6a}$ is hydrogen, alkyl, alkenyl, alkynyl, aryl, or heteroaryl, hydroxy, protected hydroxy or together with $R_6$ forms an oxo;
$R_7$ is hydrogen or together with $R_{7a}$ forms an oxo;
$R_{7a}$ is hydrogen, halogen, protected hydroxy, —$OCOR_{29}$, hydroxy, or together with $R_7$ forms an oxo;
$R_9$ is hydrogen or together with $R_{9a}$ forms an oxo;
$R_{9a}$ is hydrogen, hydroxy, protected hydroxy, or —$OCOR_{29}$ or together with $R_9$ forms an oxo;
$R_{10}$ is hydrogen or together with $R_{10a}$ forms an oxo;
$R_{10a}$ is hydrogen, hydroxy, protected hydroxy, —$OCOR_{29}$, or together with $R_{10}$ forms an oxo;
$R_{13}$ is hydroxy or protected hydroxy;
$R_{14}$ is hydrogen;
$R_{14a}$ is hydroxy, or protected hydroxy; and
$R_{29}$, $R_{30}$ and $R_{31}$ are independently hydrogen, alkyl, alkenyl, alkynyl, monocyclic aryl or monocyclic heteroaryl.

56. The compound of claim 55 having the formula:

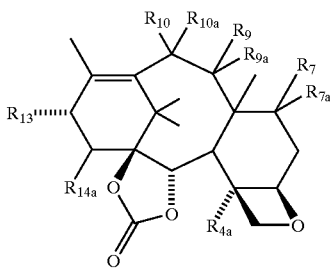

wherein $R_{4a}$, $R_7$, $R_{7a}$, $R_9$, $R_{9a}$, $R_{10}$, $R_{10a}$, $R_{13}$ and $R_{14a}$ are as defined in claim 55.

* * * * *

UNITED STATES PATENT AND TRADEMARK OFFICE
CERTIFICATE OF CORRECTION

PATENT NO. : 6,727,369 B1
DATED : April 27, 2004
INVENTOR(S) : Robert A. Holton et al.

It is certified that error appears in the above-identified patent and that said Letters Patent is hereby corrected as shown below:

Title page,
Item [54], Title, "PROCESS FOR THE PREPARATION OF BACCATIN III ANALOGS BEARING NEW C2 AND C4 FUNCTIONAL GROUPS" should read -- BACCATIN III ANALOGS BEARING NEW C2 AND C4 FUNCTIONAL GROUPS --.
Item [*] Notice, "by 1,826 days" should read -- by 0 days --.
Item [57], ABSTRACT,
Line 9, "$C_2$-$C_8$" should read -- $C_2$-$C_6$ --.

Column 1,
Lines 33-42, the chemical structure should read:

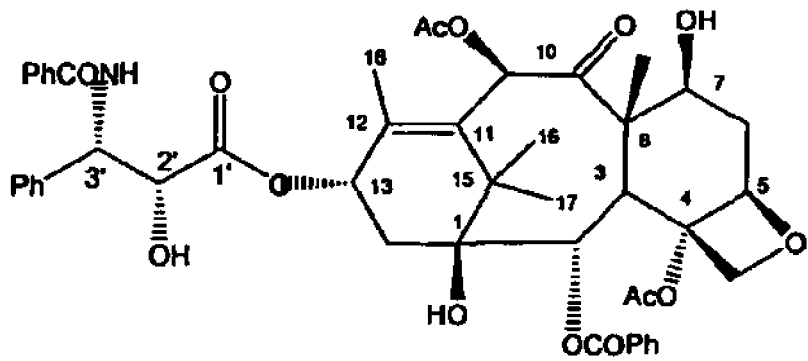

Column 12,
Approximately lines 55-65, chemical structure 10 should read:

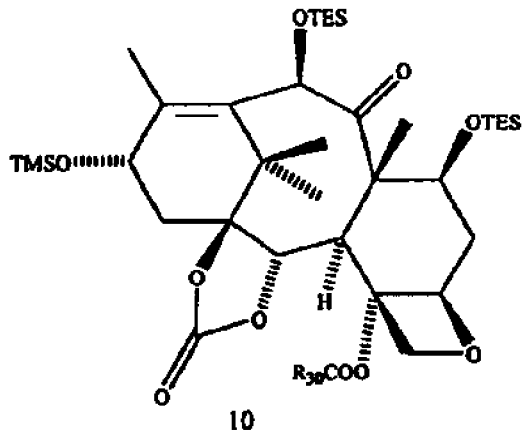

UNITED STATES PATENT AND TRADEMARK OFFICE
CERTIFICATE OF CORRECTION

PATENT NO.   : 6,727,369 B1
DATED        : April 27, 2004
INVENTOR(S)  : Robert A. Holton et al.

It is certified that error appears in the above-identified patent and that said Letters Patent is hereby corrected as shown below:

Column 21,
Approximately line 23, that portion reading "$CS_1$" should read -- $CS_2$ --.

Column 23,
Approximately lines 5-15, chemical structure 11 should read:

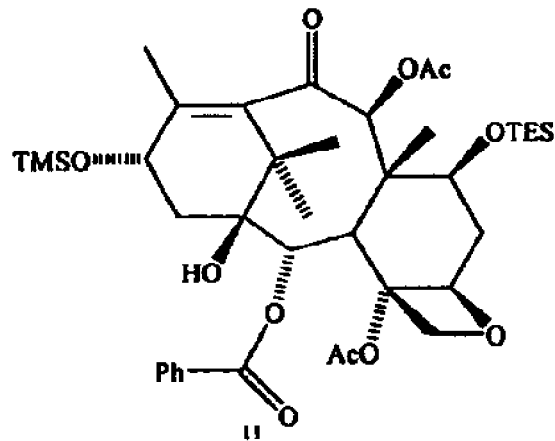

Approximately lines 15-20, underneath the first two structures, that portion reading "LHMOS" should read -- LHMDS --.
The last chemical structure, approximately lines 40-50, should read:

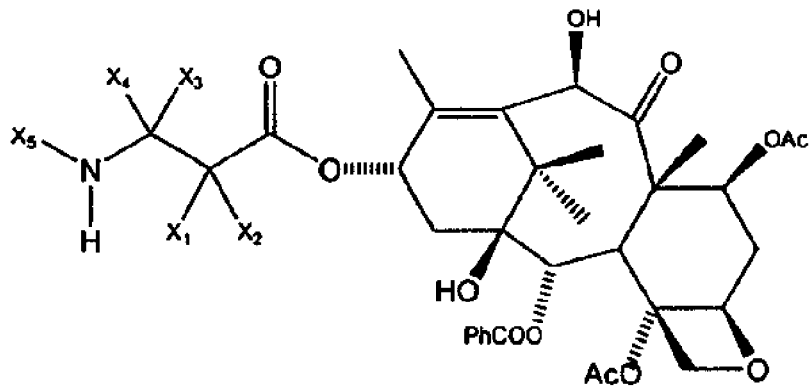

UNITED STATES PATENT AND TRADEMARK OFFICE
CERTIFICATE OF CORRECTION

PATENT NO.     : 6,727,369 B1
DATED          : April 27, 2004
INVENTOR(S)    : Robert A. Holton et al.

It is certified that error appears in the above-identified patent and that said Letters Patent is hereby corrected as shown below:

Column 25,
Lines 3-13, the first recited structure should read:

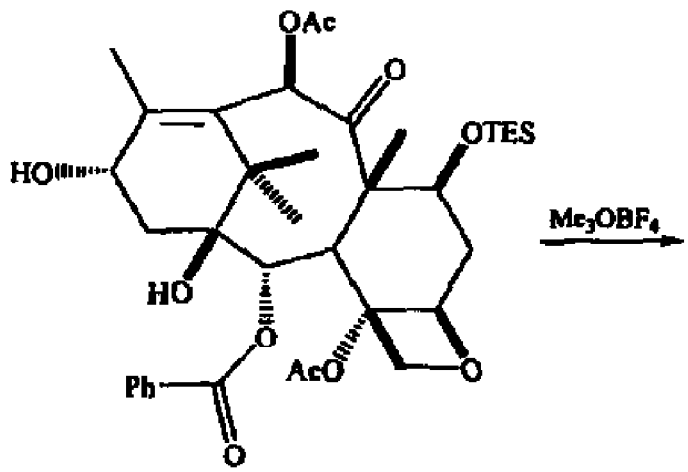

Line 25, delete "13" from the structure.
Line 39, delete "14" from the structure.

Column 26,
Lines 25-35, the chemical formula should read:

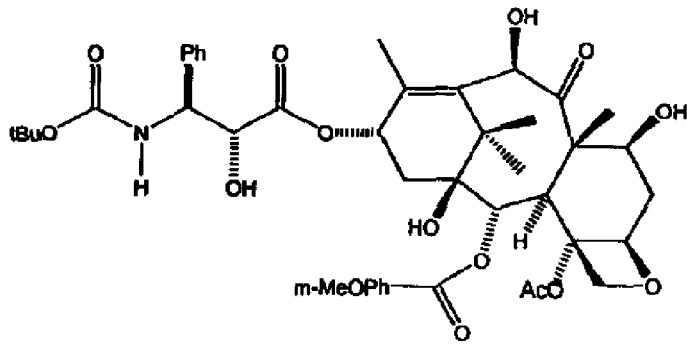

Column 38,
Line 48, "7-O-Triethylsilyl-I0-deacetyl" should read -- 7-O-Triethylsilyl-10-deacetyl --.

UNITED STATES PATENT AND TRADEMARK OFFICE
CERTIFICATE OF CORRECTION

PATENT NO.    : 6,727,369 B1
DATED         : April 27, 2004
INVENTOR(S)   : Robert A. Holton et al.

It is certified that error appears in the above-identified patent and that said Letters Patent is hereby corrected as shown below:

Column 45,
Lines 57-65, that portion of the structure reading "1) a-BuLi," should read -- 1) n-BuLi, --.

Column 48,
Lines 25-35, that portion of the structure reading "1) a-BuLi," should read -- 1) n-BuLi, --.
Lines 37-43, the chemical structure should read:

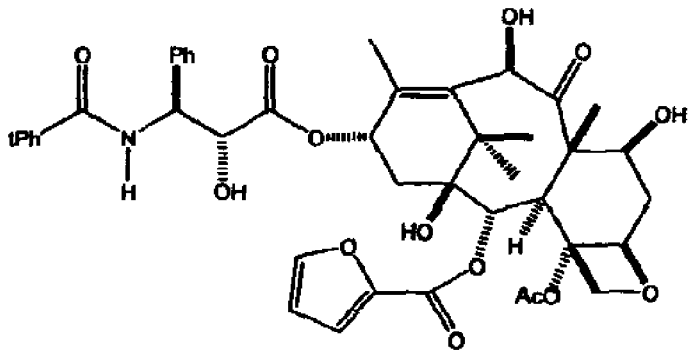

Column 55,
Lines 15-22, the chemical structure should read:

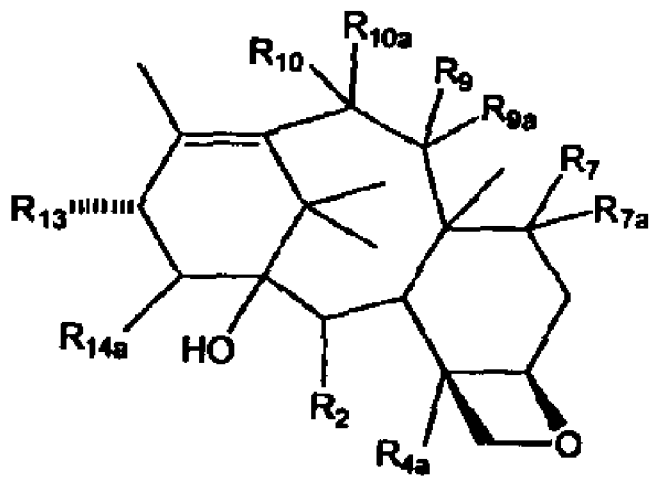

Column 59,
Line 24, "is hydrogen, alkyl," should read -- is alkyl, --.

UNITED STATES PATENT AND TRADEMARK OFFICE
CERTIFICATE OF CORRECTION

PATENT NO.     : 6,727,369 B1
DATED          : April 27, 2004
INVENTOR(S)    : Robert A. Holton et al.

It is certified that error appears in the above-identified patent and that said Letters Patent is hereby corrected as shown below:

Column 60,
Line 1, "halogen, -OCOR$_{30}$, or together" should read -- halogen, protected hydroxy, -OCOR$_{30}$, hydroxy, or together --.
Line 15, "alkynyl, or monocyclic" should read -- alkynyl, monocyclic aryl, or monocyclic --.
Lines 23-30, the chemical structure should read:

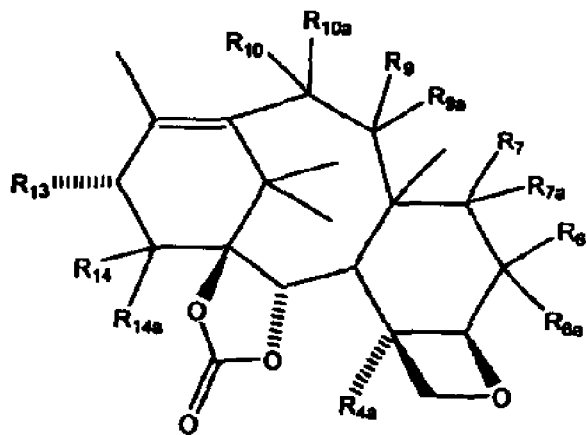

Line 64, "is hydrogen or together with R$_{10a}$ forms an oxo;" should read -- is hydrogen; --.
Line 65, "hydrogen, hydroxy, protected hydroxy," should read -- hydrogen, protected hydroxy, --.

Column 61,
Line 6, "alkynyl, or" should read -- alkynyl, monocyclic aryl, or --.
Lines 13-22, the chemical structure should read:

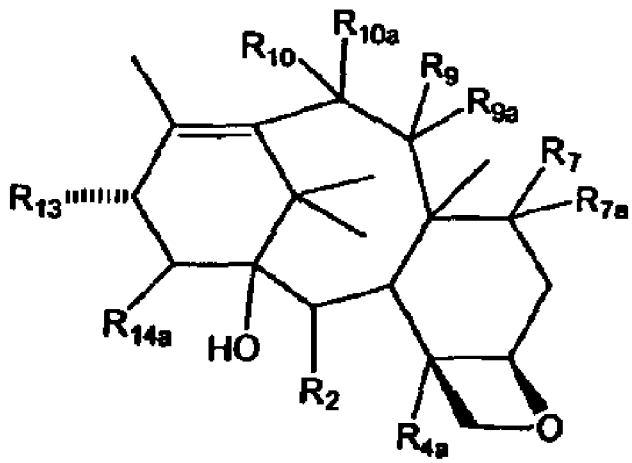

UNITED STATES PATENT AND TRADEMARK OFFICE
CERTIFICATE OF CORRECTION

PATENT NO. : 6,727,369 B1
DATED : April 27, 2004
INVENTOR(S) : Robert A. Holton et al.

It is certified that error appears in the above-identified patent and that said Letters Patent is hereby corrected as shown below:

Column 61 (cont'd),
Lines 29-37, the chemical structure should read:

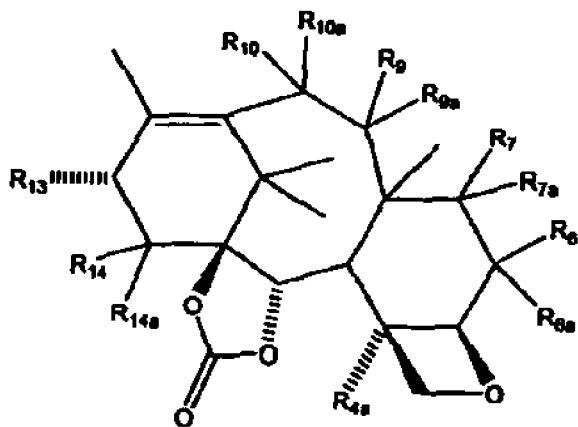

Column 63,
Lines 5-13, the chemical structure should read:

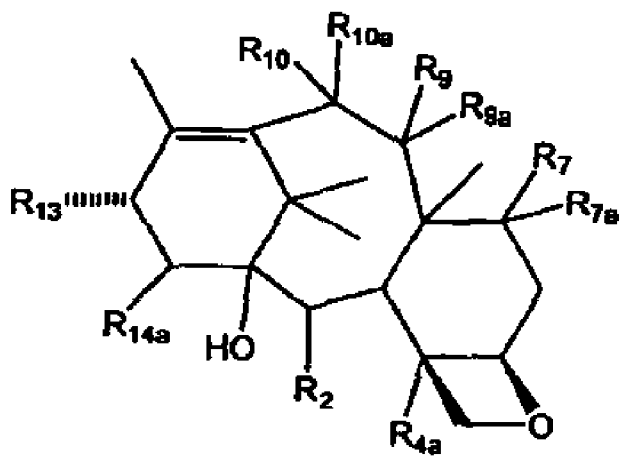

UNITED STATES PATENT AND TRADEMARK OFFICE
CERTIFICATE OF CORRECTION

PATENT NO. : 6,727,369 B1
DATED : April 27, 2004
INVENTOR(S) : Robert A. Holton et al.

It is certified that error appears in the above-identified patent and that said Letters Patent is hereby corrected as shown below:

Column 64.
Lines 11-27, the chemical structure should read:

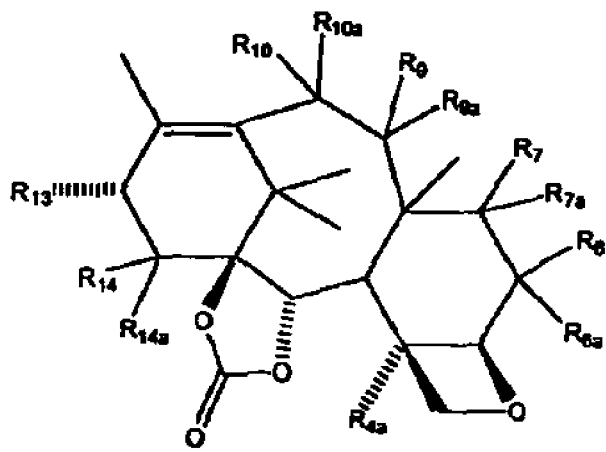

Line 35 "protected hydroxy, or" should read -- protected hydroxy, --.
Line 63 "R$_7$a" should read -- $R_{7a}$ --.

Column 65,
Line 30 "protected hydroxy, or" should read -- protected hydroxy, --.
Lines 43-52, the chemical structure should read:

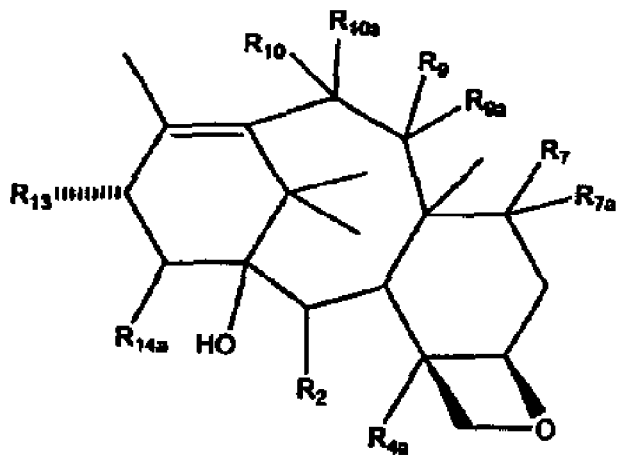

UNITED STATES PATENT AND TRADEMARK OFFICE
CERTIFICATE OF CORRECTION

PATENT NO.   : 6,727,369 B1                                  Page 8 of 11
DATED        : April 27, 2004
INVENTOR(S)  : Robert A. Holton et al.

It is certified that error appears in the above-identified patent and that said Letters Patent is hereby corrected as shown below:

Column 65 (cont'd),
Lines 58-66, the chemical structure should read:

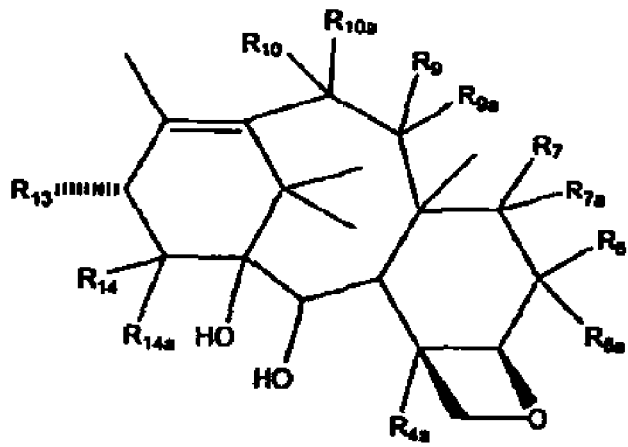

Column 66,
Lines 28-34, the chemical structure should read:

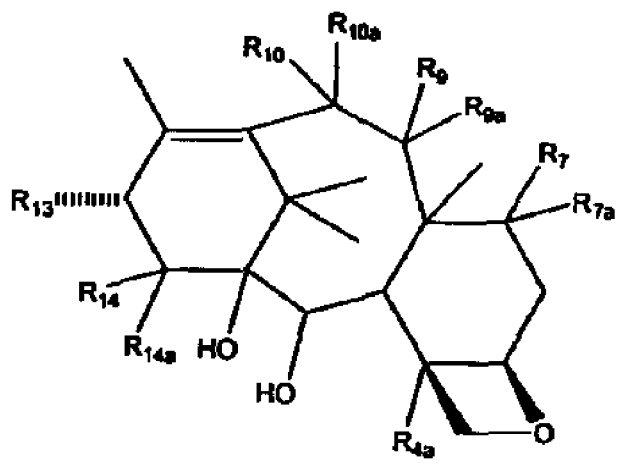

Line 66, "hydroxy, or" should read -- hydroxy --.

UNITED STATES PATENT AND TRADEMARK OFFICE
CERTIFICATE OF CORRECTION

PATENT NO. : 6,727,369 B1
DATED : April 27, 2004
INVENTOR(S) : Robert A. Holton et al.

It is certified that error appears in the above-identified patent and that said Letters Patent is hereby corrected as shown below:

Column 67,
Line 7, "is hydrogen, alkyl," should read -- is alkyl, --.
Lines 15-23, the chemical structure should read:

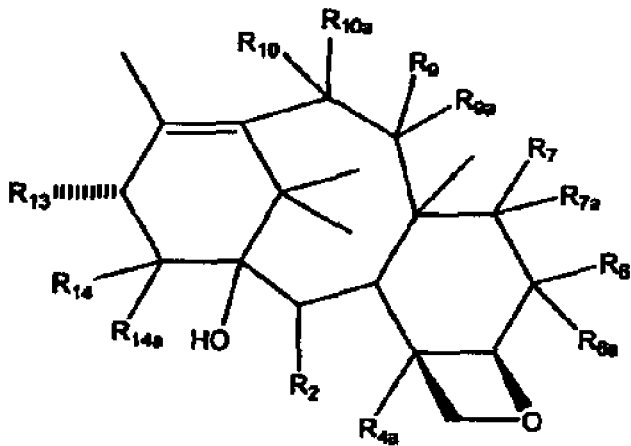

Line 66 "alkynyl, or" should read -- alkynyl, monocyclic aryl, or --.

Column 68,
Lines 7-14, the chemical structure should read:

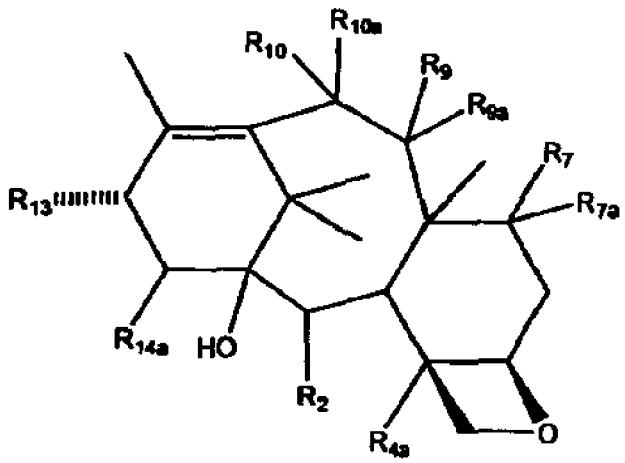

Line 62, "alkynyl, or" should read -- alkynyl, monocyclic aryl, or --.

UNITED STATES PATENT AND TRADEMARK OFFICE
CERTIFICATE OF CORRECTION

PATENT NO. : 6,727,369 B1
DATED : April 27, 2004
INVENTOR(S) : Robert A. Holton et al.

It is certified that error appears in the above-identified patent and that said Letters Patent is hereby corrected as shown below:

Column 69,
Lines 3-12, the chemical structure should read:

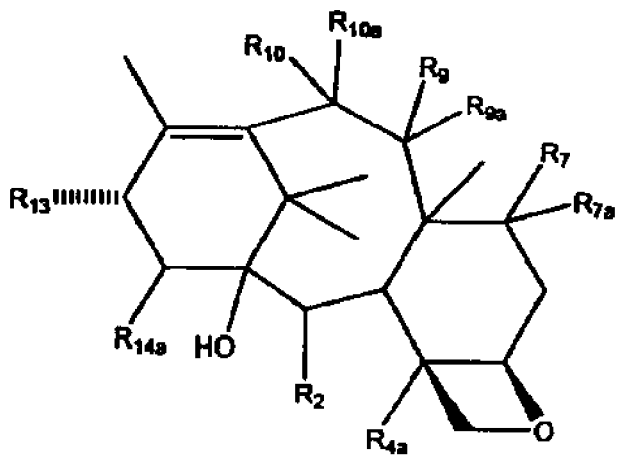

Lines 18-27, the chemical structure should read:

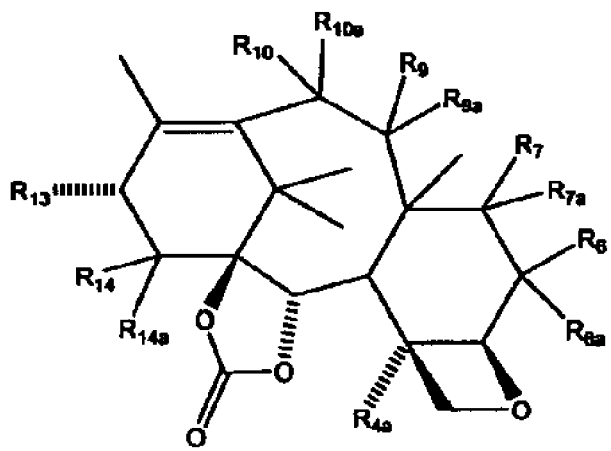

UNITED STATES PATENT AND TRADEMARK OFFICE
CERTIFICATE OF CORRECTION

PATENT NO. : 6,727,369 B1
DATED : April 27, 2004
INVENTOR(S) : Robert A. Holton et al.

It is certified that error appears in the above-identified patent and that said Letters Patent is hereby corrected as shown below:

Column 70,
Line 6, "hydroxy, or" should read -- hydroxy, --.

Signed and Sealed this

Fifteenth Day of February, 2005

JON W. DUDAS
*Director of the United States Patent and Trademark Office*